United States Patent
Juhász et al.

(10) Patent No.: US 11,098,001 B2
(45) Date of Patent: Aug. 24, 2021

(54) PROCESS FOR THE PREPARATION OF TREPROSTINIL

(71) Applicant: CHINOIN GYÓGYSZER ÉS VEGYÉSZETI TERMÉKEK GYÁRA ZRT., Budapest (HU)

(72) Inventors: Imre Juhász, Budapest (HU); Irén Hortobágyi, Budapest (HU); Tamás Altsach, Budapest (HU); István Lászlófi, Budapest (HU); Ágnes Nagyné Borkó, Budapest (HU); Imre Rozsumberszki, Budapest (HU); Gábor Havasi, Budapest (HU); Zsuzsanna Kardos, Budapest (HU); Péter Buzder-Lantos, Budapest (HU)

(73) Assignee: CHINOIN GYÓGYSZER ÉS VEGYÉSZETI TERMÉKEK GYÁRA ZRT., Budapest (HU)

( * ) Notice: Subject to any disclaimer, the term of this patent is extended or adjusted under 35 U.S.C. 154(b) by 11 days.

(21) Appl. No.: 16/397,139

(22) Filed: Apr. 29, 2019

(65) Prior Publication Data
US 2019/0248725 A1    Aug. 15, 2019

Related U.S. Application Data

(62) Division of application No. 15/518,096, filed as application No. PCT/HU2015/000065 on Sep. 28, 2015, now Pat. No. 10,322,990.

(30) Foreign Application Priority Data

Oct. 8, 2014 (HU) .................. P 14 00475

(51) Int. Cl.
| C07C 51/347 | (2006.01) |
| C07C 41/26 | (2006.01) |
| C07C 45/30 | (2006.01) |
| C07C 45/65 | (2006.01) |
| C07C 51/09 | (2006.01) |

(Continued)

(52) U.S. Cl.
CPC .......... *C07C 51/347* (2013.01); *C07C 13/547* (2013.01); *C07C 35/37* (2013.01); *C07C 41/26* (2013.01); *C07C 41/30* (2013.01); *C07C 41/48* (2013.01); *C07C 43/315* (2013.01); *C07C 45/30* (2013.01); *C07C 45/305* (2013.01); *C07C 45/65* (2013.01); *C07C 51/09* (2013.01); *C07C 51/412* (2013.01); *C07C 59/72* (2013.01); *C07C 67/14* (2013.01); *C07C 67/29* (2013.01);

(Continued)

(58) Field of Classification Search
CPC ......... C07C 41/48; C07C 69/76; C07C 49/84; C07C 51/412; C07C 59/70; C07C 43/315; C07C 67/14; C07C 67/29; C07C 67/293; C07C 45/30; C07C 45/305; C07C 45/65; C07C 51/09; C07C 59/72; C07C 49/755; C07C 41/26; C07C 51/347; C07C 13/547; C07C 2603/14; C07C 35/37; C07C 41/30; C07C 43/23; C07C 51/41; C07C 51/50; C07B 2200/13; C07F 7/18

See application file for complete search history.

(56) References Cited

U.S. PATENT DOCUMENTS

| 6,441,245 B1 | 8/2002 | Moriarty et al. |
| 2009/0163738 A1 | 6/2009 | Batra et al. |

(Continued)

FOREIGN PATENT DOCUMENTS

| CA | 1313670 C | 2/1993 |
| CN | 102040618 A | 5/2011 |

(Continued)

OTHER PUBLICATIONS

Author Unknown, "Science of Synthesis Name Reactions," Omarlic Chemistry Portal, retrieved Nov. 25, 2019, 1 page.

(Continued)

*Primary Examiner* — Jafar F Parsa
*Assistant Examiner* — Blaine G Doletski
(74) *Attorney, Agent, or Firm* — Birch, Stewart, Kolasch & Birch, LLP

(57) ABSTRACT

Treprostinil is a synthetic prostacyclin derivative with thrombocyte aggregation inhibitory and vasodilatory activity. Treprostinil can be administered in subcutaneous, intravenous, inhalable, or oral forms. Disclosed is a method for the preparation of treprostinil of formula I and its amorphous form, anhydrate form, monohydrate form, and polyhydrate form salts with bases. In the disclosed method, the chiral center in the 3-hydroxyoctyl substituent is formed at the end of the synthesis, so that the method is robust and well scalable. Also disclosed are treprostinil intermediates and the preparation of the intermediates.

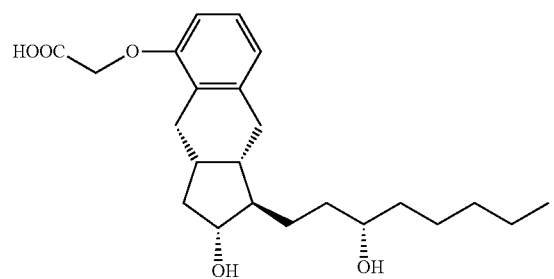

I

2 Claims, 9 Drawing Sheets

(51) Int. Cl.

| | | |
|---|---|---|
| *C07C 51/41* | (2006.01) | |
| *C07C 67/14* | (2006.01) | |
| *C07C 67/29* | (2006.01) | |
| *C07C 67/293* | (2006.01) | |
| *C07C 69/76* | (2006.01) | |
| *C07C 41/30* | (2006.01) | |
| *C07C 41/48* | (2006.01) | |
| *C07C 43/315* | (2006.01) | |
| *C07C 13/547* | (2006.01) | |
| *C07C 35/37* | (2006.01) | |
| *C07C 59/72* | (2006.01) | |

(52) U.S. Cl.
CPC ............ *C07C 67/293* (2013.01); *C07C 69/76* (2013.01); *C07C 2603/14* (2017.05)

(56) References Cited

U.S. PATENT DOCUMENTS

| | | |
|---|---|---|
| 2013/0053581 A1 | 2/2013 | Wei et al. |
| 2013/0331593 A1 | 12/2013 | McGowan et al. |
| 2014/0256730 A1 | 9/2014 | Becker et al. |
| 2014/0275616 A1* | 9/2014 | Batra ................ C07C 59/72 562/466 |
| 2015/0126761 A1 | 5/2015 | Jain et al. |

FOREIGN PATENT DOCUMENTS

| | | |
|---|---|---|
| CN | 103193627 A | 7/2013 |
| EA | 201401293 A1 | 7/2015 |
| EP | 1 628 654 A2 | 3/2006 |
| EP | 2674413 A1 | 12/2013 |
| JP | 56-138130 A | 10/1981 |
| JP | 2007-501281 A | 1/2007 |
| JP | 2013-528621 A | 7/2013 |
| JP | 2017-522304 A | 8/2017 |
| WO | WO 99/21830 A1 | 5/1999 |
| WO | WO 99/25357 A1 | 5/1999 |
| WO | WO 2005/007081 A2 | 1/2005 |
| WO | WO 2009/137066 A1 | 11/2009 |
| WO | WO 2011/153363 A1 | 12/2011 |
| WO | WO 2012/009816 A1 | 1/2012 |
| WO | WO 2012/066607 A1 | 7/2012 |
| WO | WO-2012088607 A1 * | 7/2012 ............ C07C 51/43 |
| WO | WO 2013/174848 A2 | 11/2013 |
| WO | WO 2014/089385 A2 | 6/2014 |
| WO | WO 2014/150203 A1 | 9/2014 |

OTHER PUBLICATIONS

Ferenc, "Gyógyszerkémiai Alapfolyamatok," 2011, pp. 1-238.
Greene, Protective Groups in Organic Synthesis, 1981, John Wiley & Sons, Inc., New York, p. 4 (Year: 1981).
Moriarty et al., Journal of Organic Chemistry, The Intramolecular Asymmetric Pauson-Khand Cyclization as a Novel and General Stereoselective Route to Benzindene Prostacyclins: Synthesis of UT-15 (Treprostinil), 2004, 69, pp. 1890-1902 (Year: 2004).
Non Final Office Action dated Mar. 28, 2018 in copending U.S. Appl. No. 15/518,096.
Non Final Office Action dated Sep. 21, 2018 in copending U.S. Appl. No. 15/518,096.
Notice of Allowance dated Jan. 28, 2019 in copending U.S. Appl. No. 15/518,096.
Skoro-Sajer, N., "Optimal Use of Treprostinil in Pulmonary Arterial Hypertension," Drugs, 2012, vol. 72, No. 18, pp. 2351-2363.
Sorbera, L.A., et al, "Treatment of Pulmonary Hypertension Treatment of Peripheral Vascular Disease," Drugs of the Future, 2001, vol. 26, No. 4, pp. 364-374.
Wuts, P.G.M., et al, "Greene's Protective Groups in Organic Synthesis," 4th edition, John Wiley & Sons, Inc., 2007, Contents pages.
Zaragoza Dorwald, Side Reactions in Organic Synthesis, 2005, Wiley-VCH Verlag GmbH & Co. KGaA, Weinheim, Preface. p. IX (Year 2005).

* cited by examiner

Figure 1 Treprostinil Na white solid (amorphous form). Mp: 65-90 °C DSC:
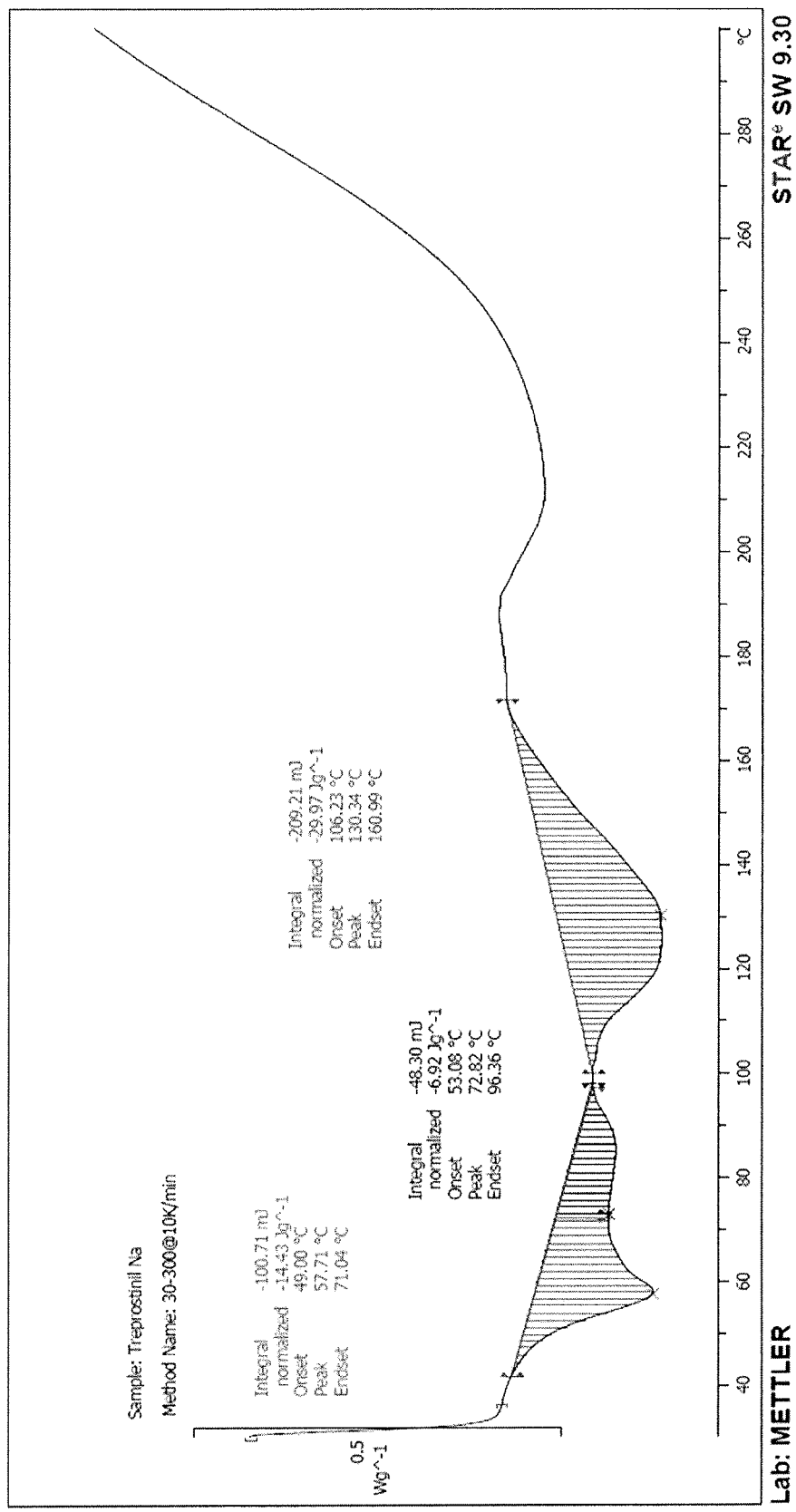

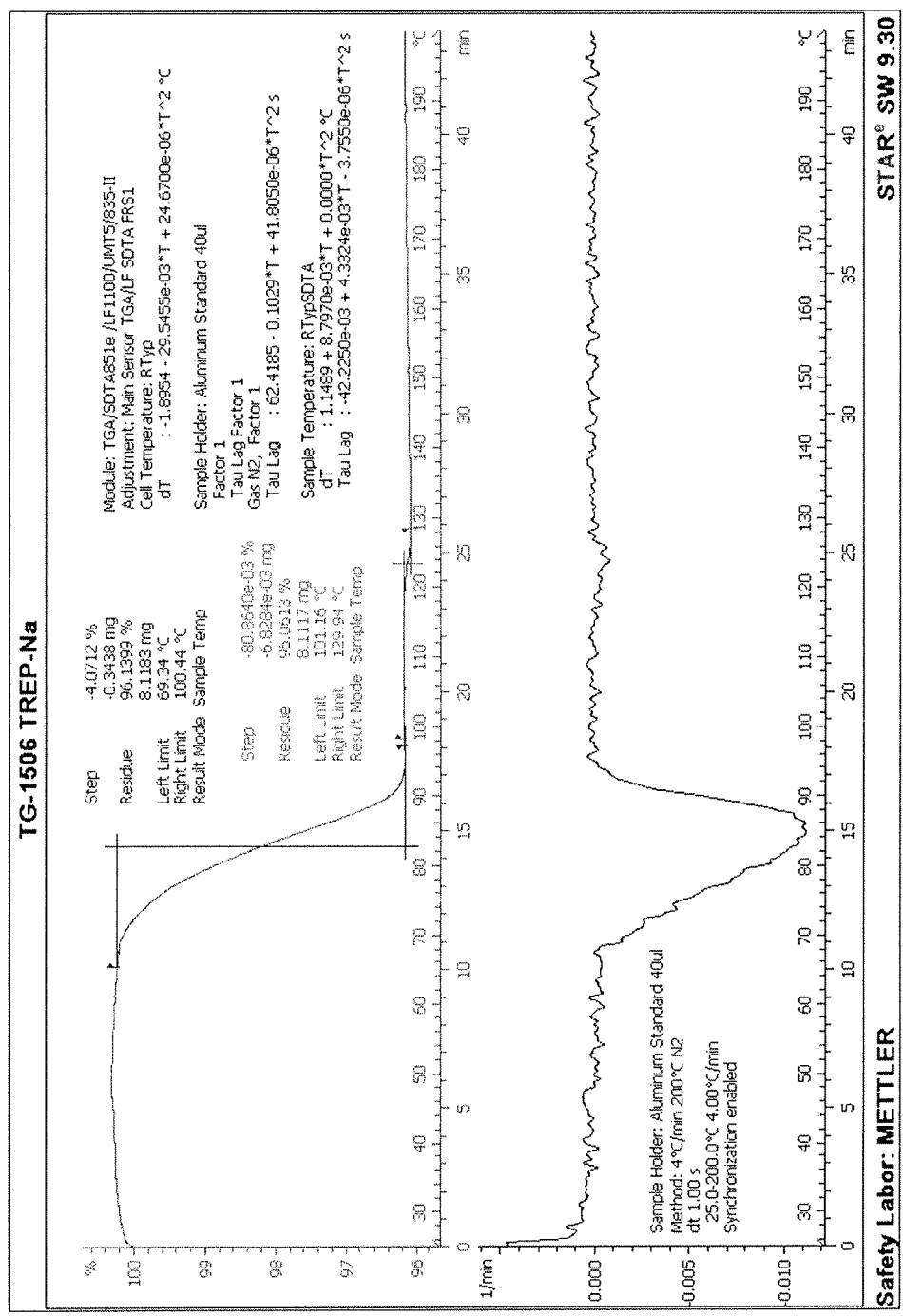
Figure 2    Treprostinil Na monohydrate (Form *A*) *TG spectrum*:

Figure 3 Treprostinil Na monohydrate (Form A) DSC spectrum:
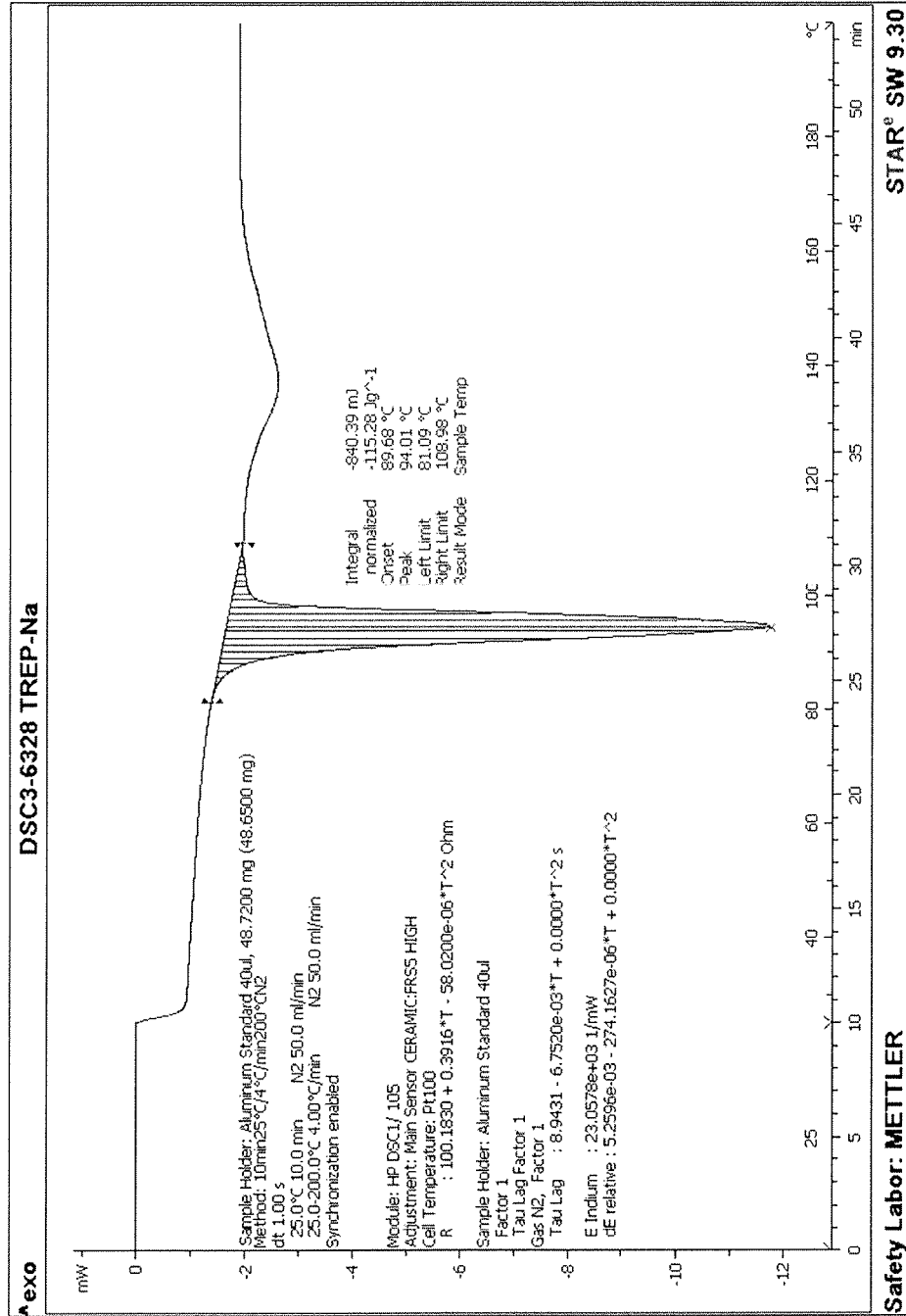

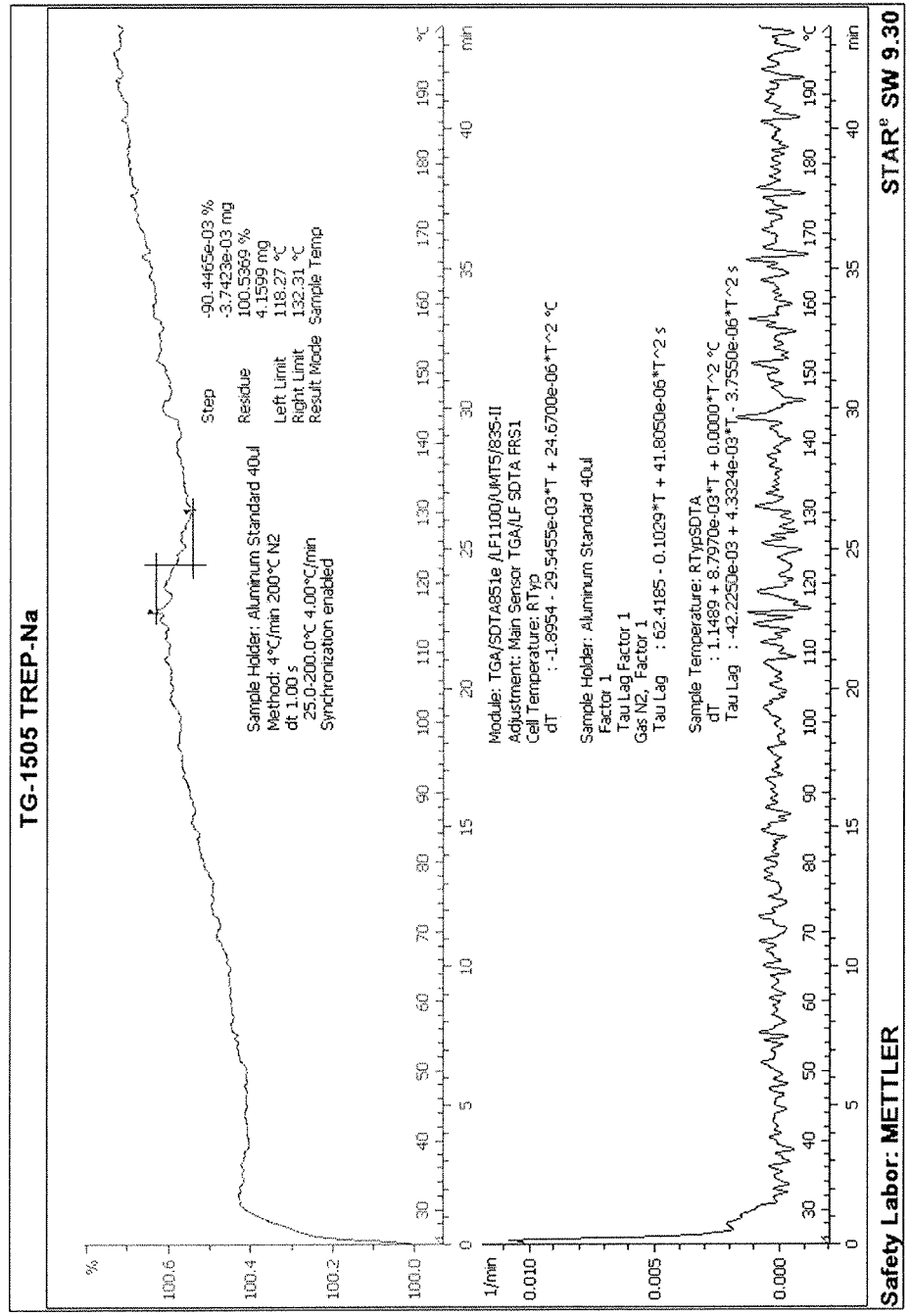
Figure 4 Treprostinil Na anhydrate (Form B) TG spectrum:

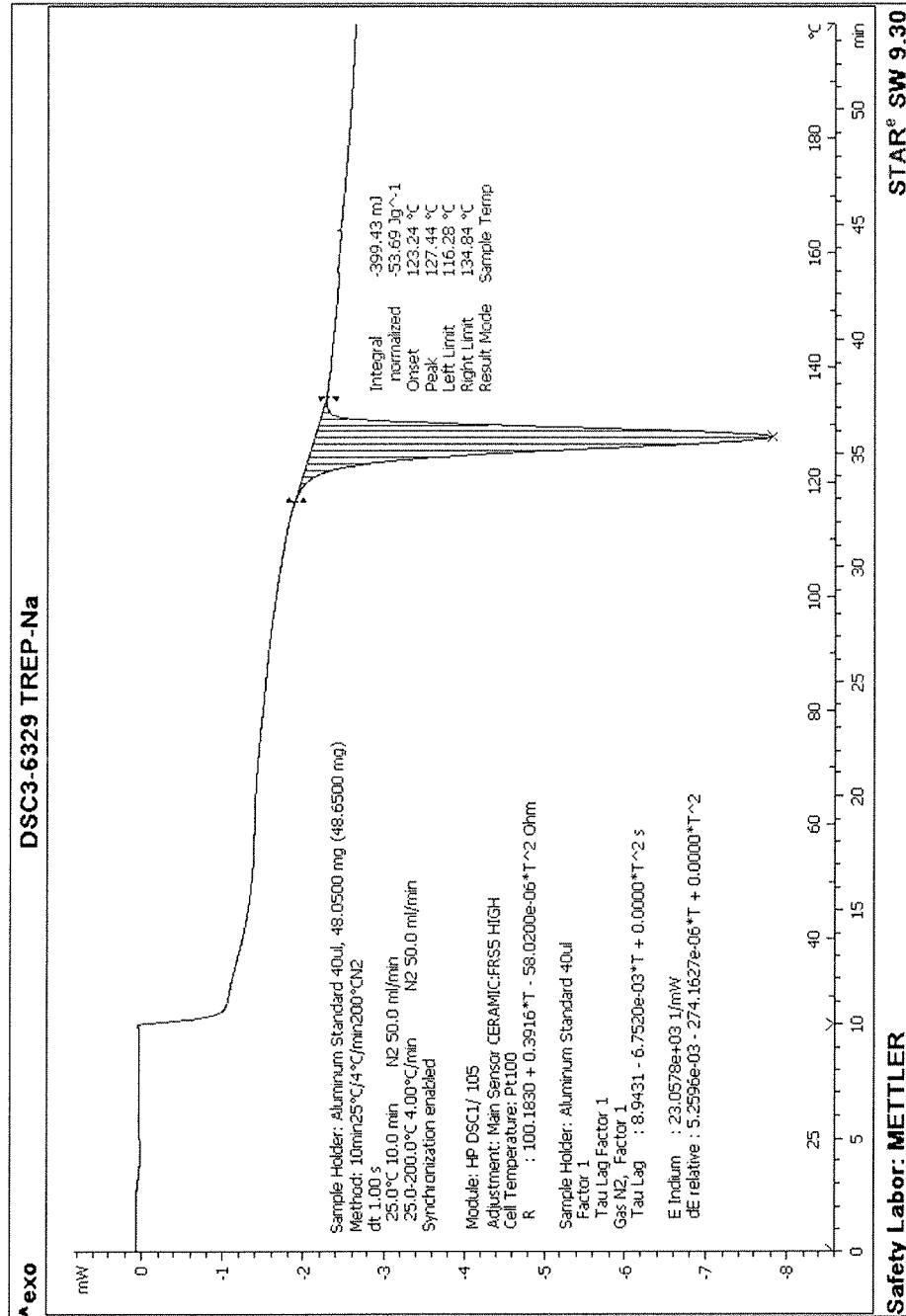
Figure 5  Treprostinil Na anhydrate (Form *B*) *DSC spectrum*:

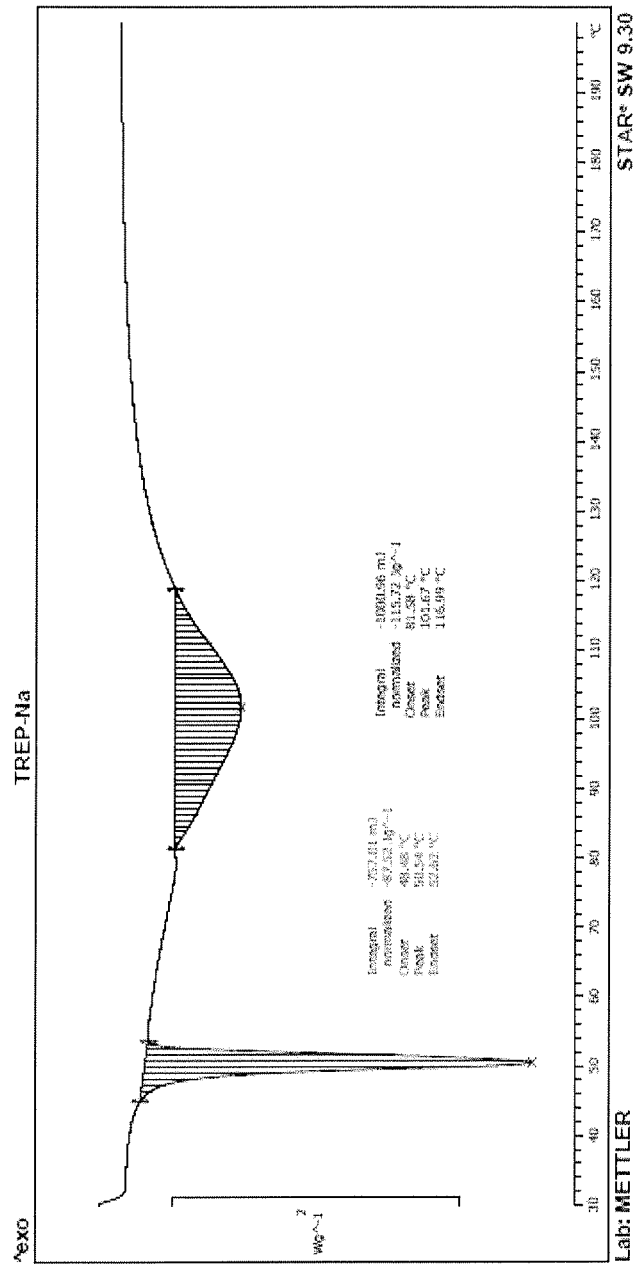
Figure 6  DSC diagram of Treprostinil sodium salt polyhydrate (Form C)

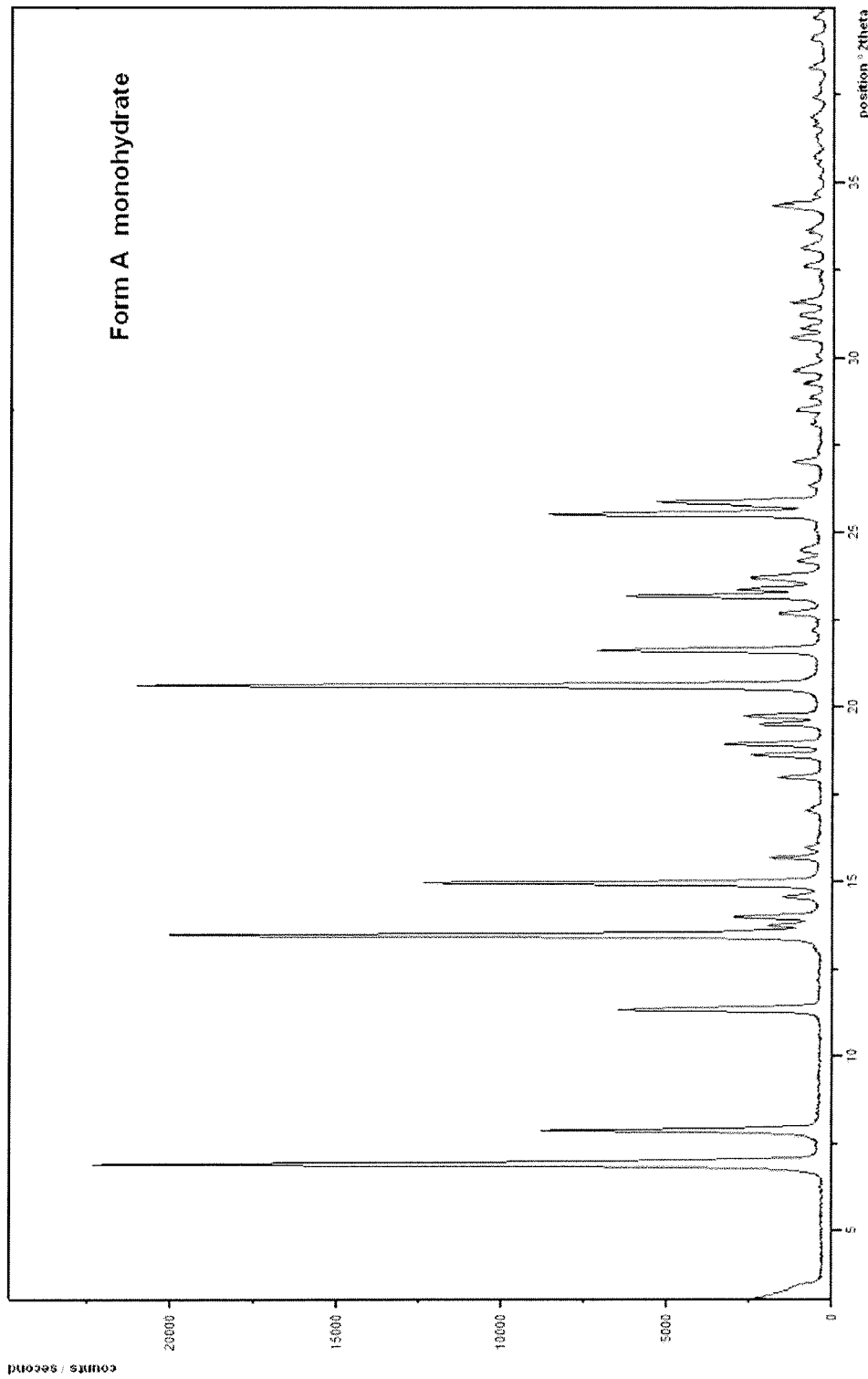
Figure 7 Powered X-ray diffraction spectrum of Treprostinil Na – Form A monohydrate

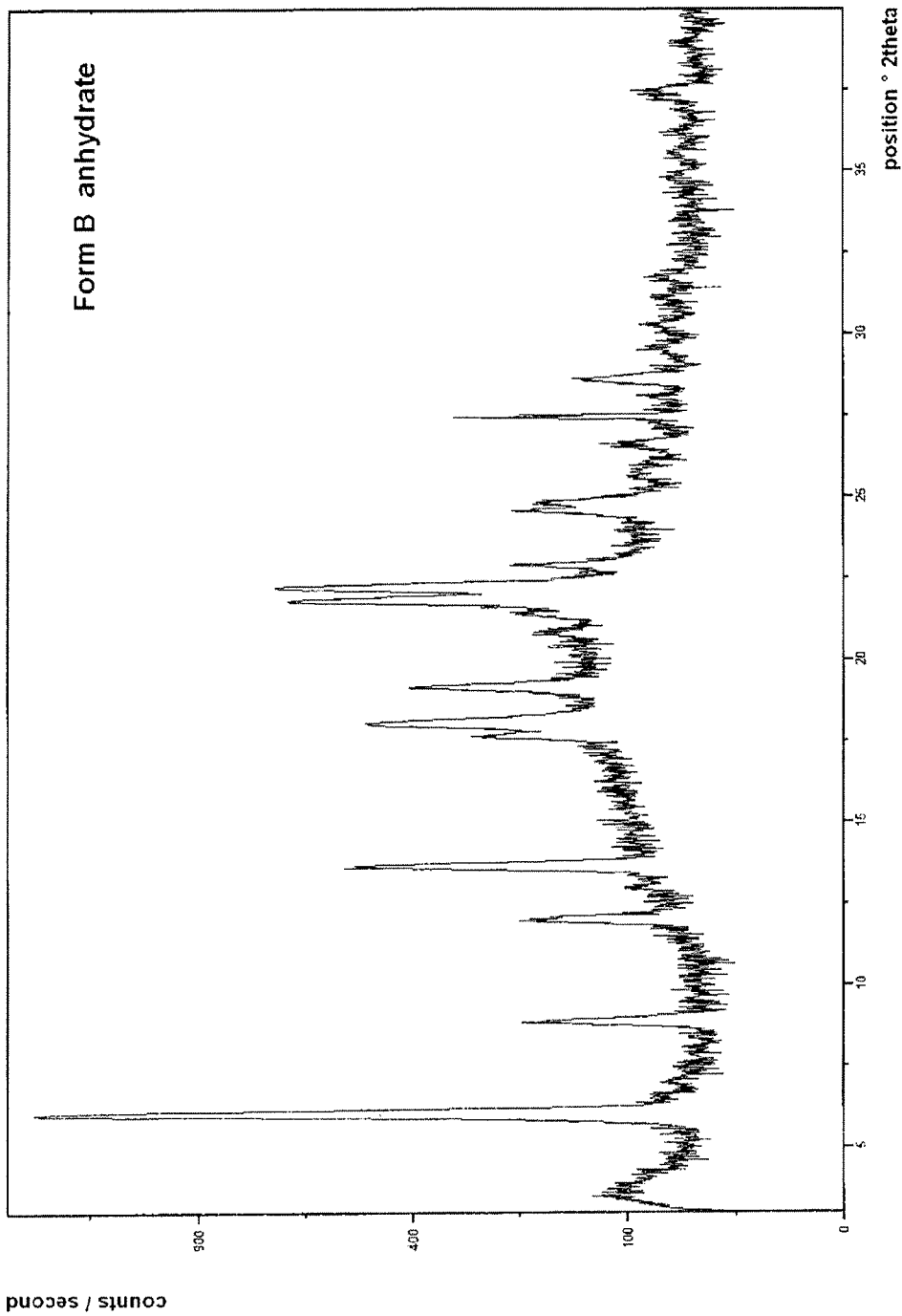
Figure 8 Powered X-ray diffraction spectrum of Treprostinil Na — Form B anhydrate

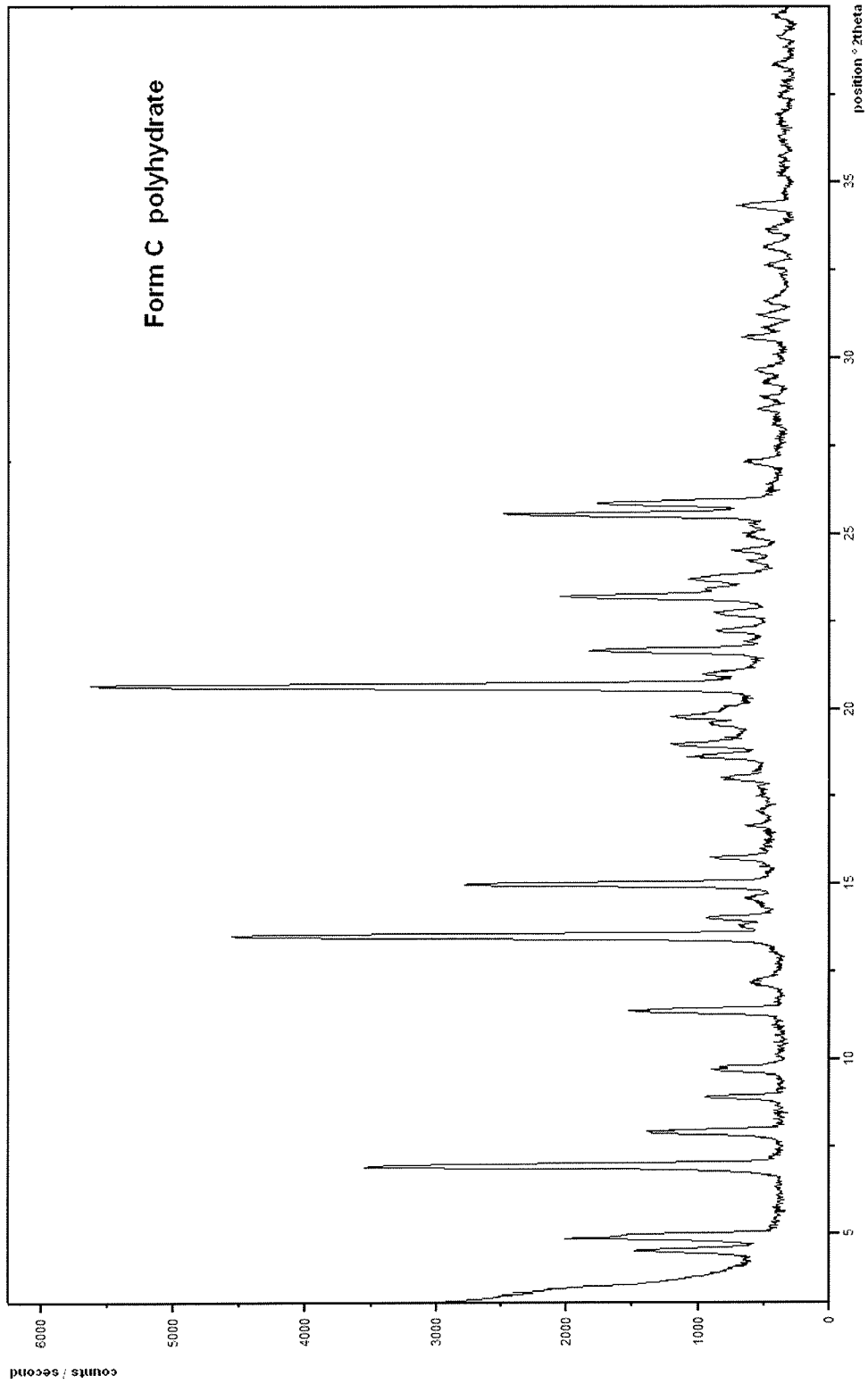
Figure 9 Powered X-ray diffraction spectrum of Treprostinil Na – Form C polyhydrate

PROCESS FOR THE PREPARATION OF TREPROSTINIL

This application is a Divisional of application Ser. No. 15/518,096 filed on Apr. 10, 2017, now U.S. Pat. No. 10,322,990 issued Jun. 18, 2019, which is the U.S. National Phase of PCT/HU2015/000065, filed Sep. 28, 2015, and which claims priority under 35 U.S.C. § 119(a) to Application No. 1400475 filed in Hungary, on Oct. 8, 2014, the entire contents of which are expressly incorporated by reference into the present application.

The invention relates to the preparation of treprostinil of formula I and its amorph, anhydrate, monohydrate and polyhydrate salts given with bases, to treprostinil intermediates of general formulae III, IV, V, VI, VII, VIII, IX, X, XI, XII, XIII, XIV and XV and to their preparation.

I

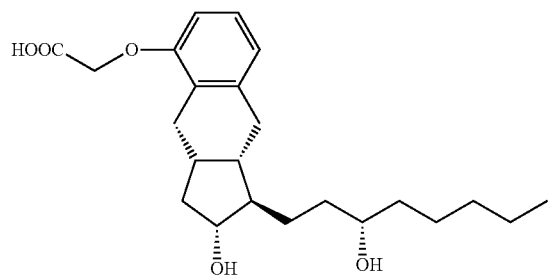

Treprostinil is a synthetic prostacyclin derivative with thrombocyte aggregation inhibitory and vasodilatory activity, it can be administered in subcutaneous, intravenous, inhalatory or oral forms.

Its therapeutic field is the treatment of pulmonary arterial hypertension (Pulmonary Arterial Hypertension, PAH). (*Drugs*, 2012, 72 (18) 2351-2363).

For the construction of the benzindene structural part of treprostinil several methods are known. A summary of the hitherto described synthetic routes has been published in *Drugs of the Future*, 2001, 26 (4) 364-374.

Comparing the synthetic routes, the Pauson-Khand cyclisation—described in patent specification WO99/21830 A1—seems to be the most effective method for the construction of the ring system.

According to the example disclosed in patent specification WO 99/21830 A1 (U.S. Pat. No. 6,441,245 B1), the benzindene key intermediate is synthesized by the reaction route outlined in Scheme 10.

Scheme 10 is shown at the end of the description part, prior to the Examples.

The key intermediate is then transformed into treprostinil by known chemical reactions as demonstrated in Scheme 11, shown at the end of the description part, prior to the Examples.

In patent specification WO 2009/158010 A1 the preparation of deuterated treprostinil derivatives is disclosed.

The ring closure is performed by Pauson-Khand cyclisation. In that case, too, the chain with the triple bond consists of at least seven carbon atoms. The molecule resulting from the Pauson-Khand cyclisation already contains the treprostinil side-chain (Scheme 1).

Scheme 1

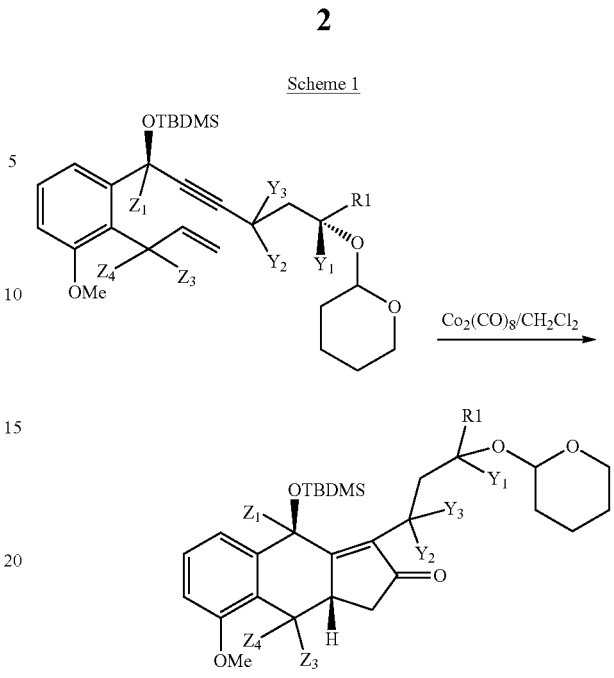

where Z$_{(1,3,4)}$' and Y$_{(1,2,3)}$' stand for hydrogen or deuterium where R1' is pentyl group optionally containing one or more deuterium.

The differences between the methods described in patent specifications WO 2011/153363 A1 and WO 99/21830 A1 are as follows:

The coupling of the side chain containing the triple bond to the aldehyde is carried out in the presence of chiral catalyst ((+)-N-methylephedrine), in that way the chiral alcohol is obtained in one step, without the formation of the racemic alcohol. In this way, one oxidation step and the stereoselective reduction are eliminated.

The amount of the dicobalt octacarbonyl has been decreased (instead of equimolar ratio only 2-15 mol % are used) and the ring closure is carried out under carbon monoxide pressure. The full synthesis scheme is presented in FIG. 4, at the end of the description part, prior to the Examples.

The synthesis described in patent specification WO 2012/009816 A1 also utilises the Pauson-Khand cyclisation for the formation of the benzindene ring. Novelty in the synthesis is that the phenolic hydroxyl group is protected with p-methoxybenzyl (PMB) protective group. The side chain with the triple bond contains, in that case too, at least seven carbon atoms.

The molecule resulting from the Pauson-Khand cyclisation will already contain the treprostinil side-chain.

The full synthesis scheme is presented in Scheme 13, at the end of the description part, before the Examples.

Synthesis of a treprostinil salt is given in detail in patent specification WO 2009/078965 (PCT/US2008/013686) (United Therapeutics). It describes the preparation of the crystalline diethanolamine salt.

According to the method the benzindenenitrile is obtained via alkylation of the aromatic hydroxyl group of the benzindene structure. (Scheme 2)

Scheme 2
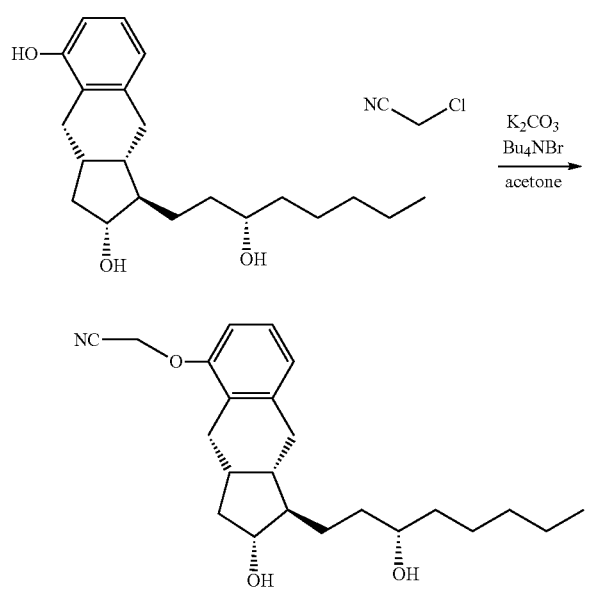
The benzindenenitrile is hydrolyzed to treprostinil and transformed, without isolation, into the crystalline diethanolamine salt. (Scheme 3)
From the treprostinil diethanolamine salt the treprostinil is liberated by treatment with acid. (Scheme 4)
Scheme 4
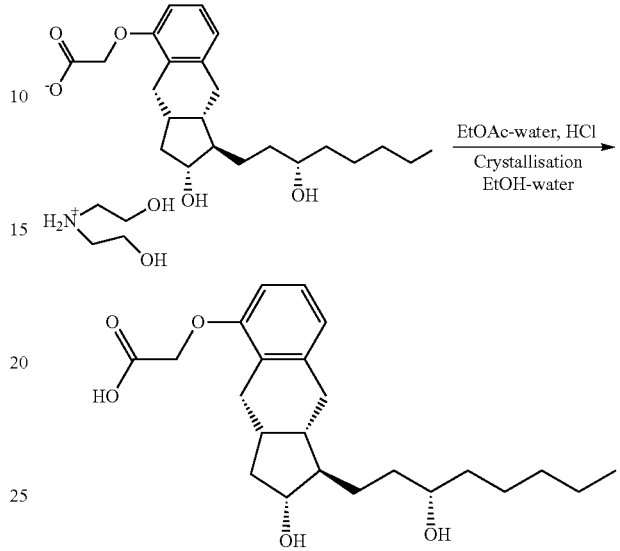
Scheme 3
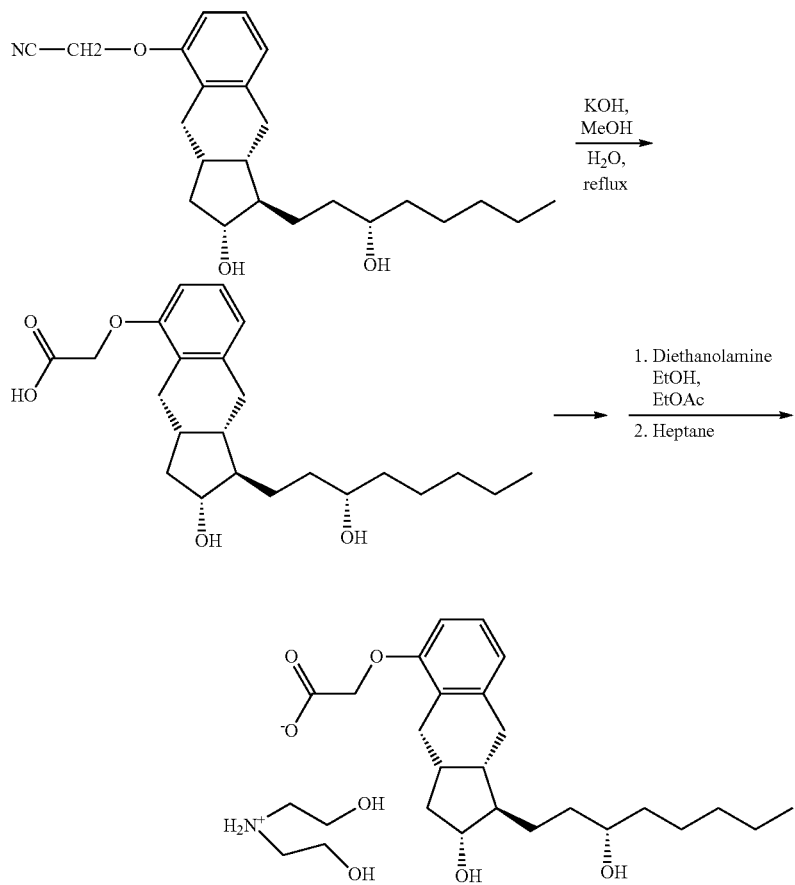

After separation of the phases the ethyl acetate phase is evaporated, the residue is crystallized with aqueous ethanol, collected by filtration and dried.

Purification through the diethanolamine salt is so effective that purification of the benzindenenitrile derivative by chromatography is not needed.

The high purity treprostinil can be transformed with various bases into the desired high purity salts.

Detailed description of the sodium salt formation is described in patent specification WO 2012/088607.

According to the description the benzindene derivative is alkylated with bromoacetic acid methyl ester and the resulting treprostinil methyl ester is hydrolyzed without purification into treprostinil by use of potassium hydroxide in methanol-water solvent mixture.

The reaction mixture is then acidified with hydrochloric acid, the precipitated white solid is filtered off, washed with methanol-water mixture, dried in vacuum and transformed into the sodium salt. (Scheme 5)

Scheme 5

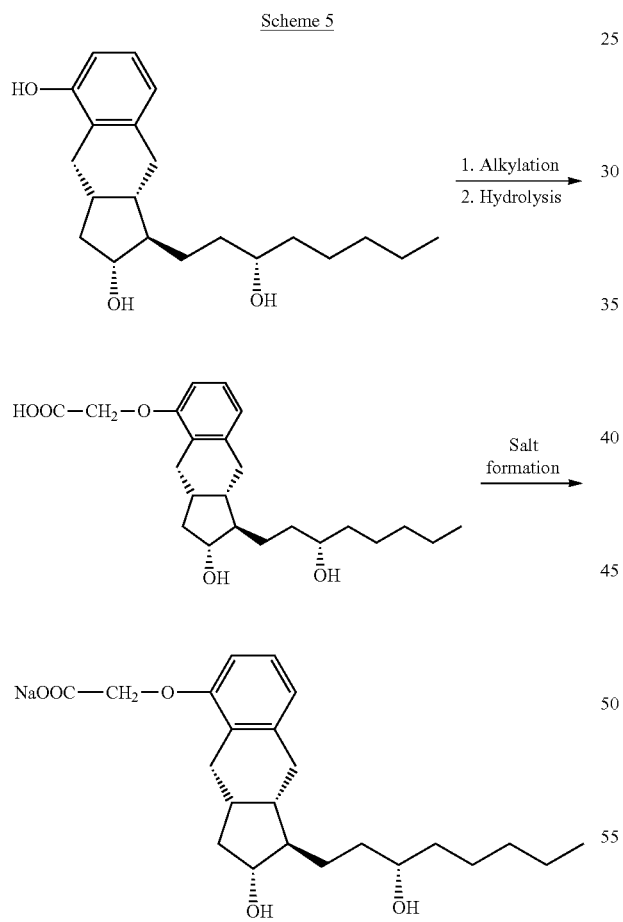

We aimed to elaborate a method where the chiral center in the lower chain is built out only at the end of the synthesis and the method is robust and well scalable.

The subject of the invention is a method for the preparation of treprostinil of formula I and its amorph, anhydrate salts given with bases, as well as the monohydrates and polyhydrates thereof

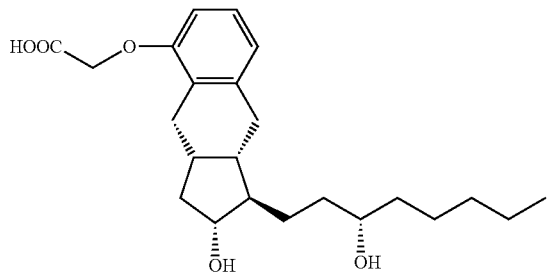

characterized in that, a.) a compound of the general formula XVII

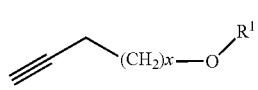

where in the formula $R^1$ represents a protective group containing silicium atom, tetrahydropyranyl-, trityl-, methoxymethyl-, ethoxymethyl-, methoxyethoxymethyl-, methylthiomethyl-, benzyloxymethyl- group-, with the proviso that the $R^1$ protective group must be selectively removable from $R^2$ and $R^4$, and x represents 0 or 2—, and a compound of the general formula XVI

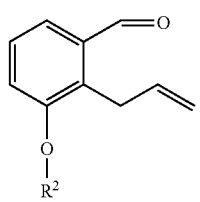

where in the formula $R^2$ represents —$(CH_2)_n$Y, where

Y stands for hydrogen atom, halogen atom, phenyl-, nitrile-, —$OR^5$ or —$COOR^5$ group, wherein $R^5$ means $C_{1-4}$ alkyl-, tetrahydropyranyl-, tri($C_{1-4}$)alkyl-silyl- or ($C_{1-4}$)alkyl-di($C_{6-10}$)arylsilyl- group and n stands for 1, 2, 3, 4—, a1.) is reacted in the presence of Grignard reagent, and the resulting compound of the general formula XV

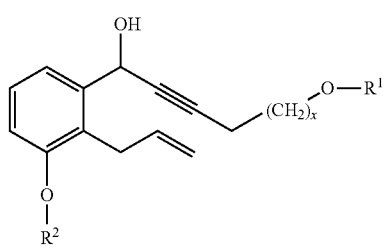

where in the formula the meanings of x, $R^1$ and $R^2$ are as defined above—is oxidized, and the resulting compound of the general formula XIV

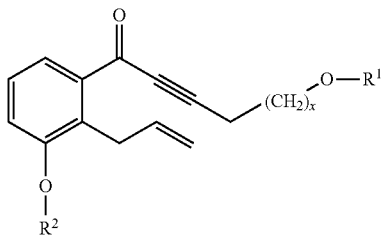

XIV where in the formula the meanings of x, $R^1$ and $R^2$ are as defined above—is selectively reduced, or a2.) are reacted in the presence of chiral base and zinc salt, and the compound of the general formula XII obtained in step a1.) or a2.)

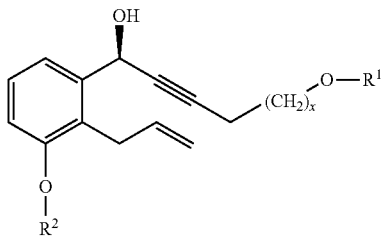

XIII where in the formula the meanings of x, $R^1$ and $R^2$ are as defined above—is reacted with a compound suitable for the introduction of group $R^3$—where $R^3$ represents a protective group containing silicium atom, tetrahydropyranyl-, trityl-, methoxymethyl-, ethoxymethyl-, methoxyethoxymethyl-, methylthiomethyl-, benzyloxymethyl- or $C_{1-13}$ acyl- group-, b.) the resulting compound of the general formula XII

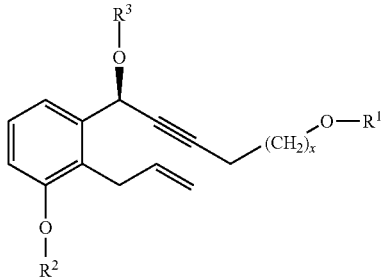

XII where in the formula the meanings of x, $R^1$, $R^2$ and $R^3$ are as defined above—is subjected to intramolecular cyclisation, c.) the resulting compound of the general formula XI

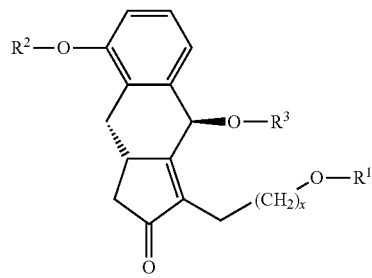

XI where in the formula the meanings of x, $R^1$, $R^2$ and $R^3$ are as defined above—is catalytically hydrogenated, and in the case where x=0 isomerized, d.) the resulting compound of the general formula X

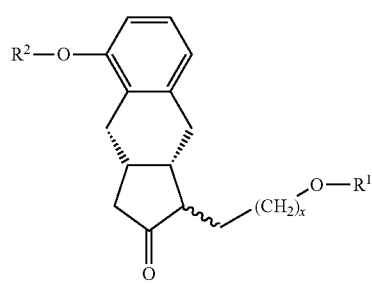

X where in the formula the meanings of x, $R^1$, $R^2$ are as defined above —, is reduced, e.) the resulting compound of the general formula IX

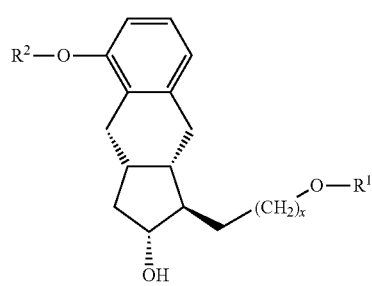

IX where in the formula the meanings of x, $R^1$ and $R^2$ are as defined above—is reacted with a compound suitable for the introduction of group $R^4$—where $R^4$ represents a protective group containing silicium atom, trityl-, methoxytrityl-, p-methoxybenzyl-, methoxymethyl-, ethoxymethyl-, methoxyethoxymethyl-, methylthiomethyl-, benzyloxymethyl- or $C_{1-13}$ acyl- group, with the proviso that the $R^4$ protective group must be selectively removable from $R^2$, and $R^1$ must be selectively removable from $R^4$, f.) from the resulting compound of the general formula VIII

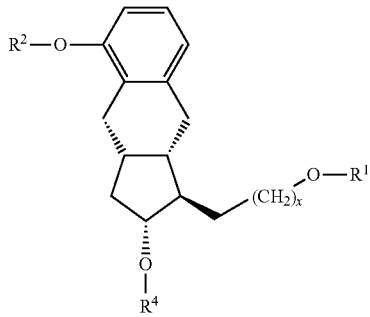

VIII where in the formula the meanings of x, $R^1$, $R^2$ and $R^4$ are as defined above—the $R^1$ protective group is cleaved in acidic medium, g) the resulting compound of the general formula VII

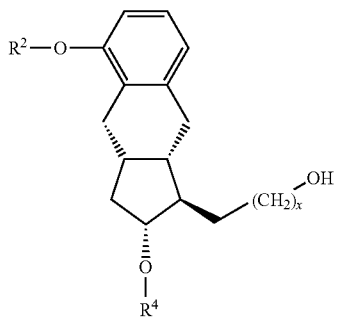

VII where in the formula the meanings of x, $R^2$ and $R^4$ are as defined above—is oxidized, h.) the resulting compound of the general formula VI

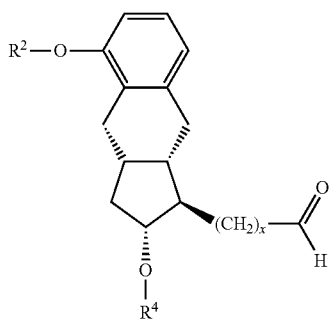

VI where in the formula the meanings of x, $R^2$ and $R^4$ are as defined above— h1.) in the case where x means 0, is reacted in Wittig reaction with the compound of general formula

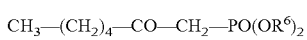

$CH_3—(CH_2)_4—CO—CH_2—PO(OR^6)_2$ where in the formula $R^6$ stands for $C_{1-4}$ alkyl- or phenyl-group-, and the resulting compound of the general formula V

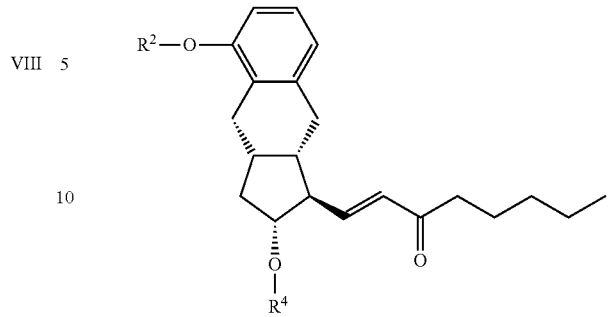

V where in the formula the meanings of $R^2$ and $R^4$ are as defined above—is selectively reduced, the protective group of the resulting compound of the general formula IVa.

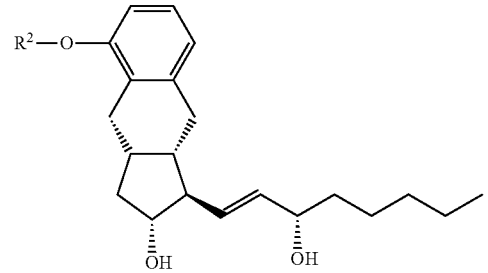

IVa where in the formula the meanings of $R^2$ and $R^4$ are as defined above—

$R^4$ is removed, the resulting compound of the general formula III.

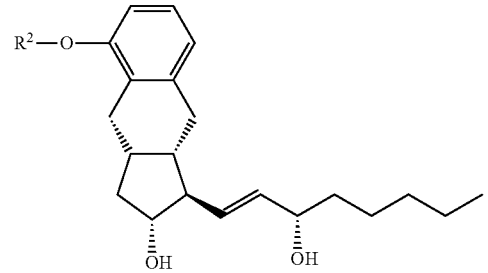

III where in the formula the meaning of $R^2$ is as defined above—is hydrogenated, or h2.) in the case where x means 2, is reacted with organic metal reagent in the presence of chiral catalyst, and the protective group $R^4$ of the resulting compound of the general formula IVb.

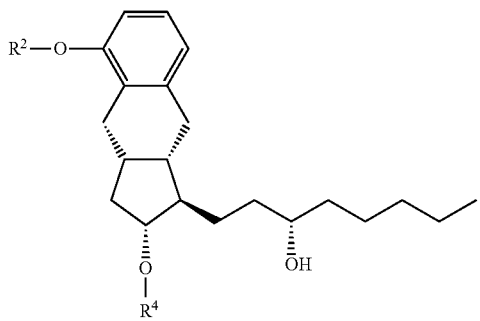

IVb where in the formula the meanings of $R^2$ and $R^4$ are as defined above—then $R^4$ is removed,
i) the compound of the general formula II. obtained in steps h1.) or h2.)

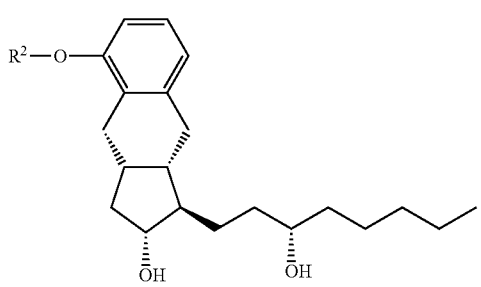

II where in the formula the meaning of $R^2$ is as defined above—is transformed by known method into treprostinil of formula I, and if desired, into its amorph, anhydrate, monohydrate and polyhydrate salts given with bases.

As $R^1$ protective group preferably methoxymethyl-, methoxyethoxymethyl-, or tetrahydropyranyl- group, as $R^2$ protective group methyl group, as $R^3$ protective group a protective group containing silicium atom, preferably tert-butyldimethylsilyl group, as $R^4$ protective group p-phenylbenzoyl group may be applied.

The invention furthermore relates to the preparation of the optically active compounds of the general formula II

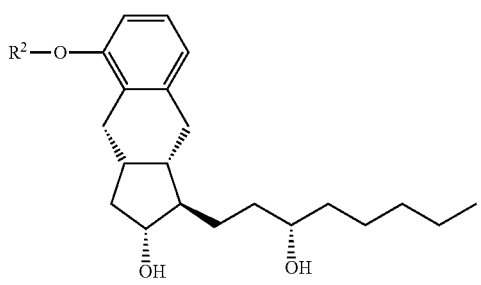

II where in the formula
$R^2$ represents —$(CH_2)_n Y$, where
Y stands for hydrogen atom, halogen atom, phenyl-, nitrile-, —$OR^5$ or —$COOR^5$ group, wherein
$R^5$ means $C_{1-4}$ alkyl-, tetrahydropyranyl-, tri($C_{1-4}$)alkyl-silyl- or ($C_{1-4}$)alkyl-di($C_{6-10}$)arylsilyl- group and n stands for 1, 2, 3, 4.

According to the invention the compounds of the general formula II. can be prepared so that a compound of the general formula III

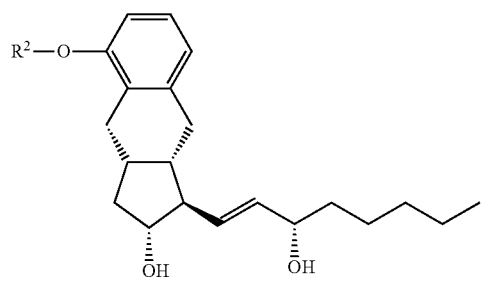

III where in the formula the meaning of $R^2$ is as defined above—is hydrogenated, or the $R^4$ protective group of a compound of the general formula IVb.

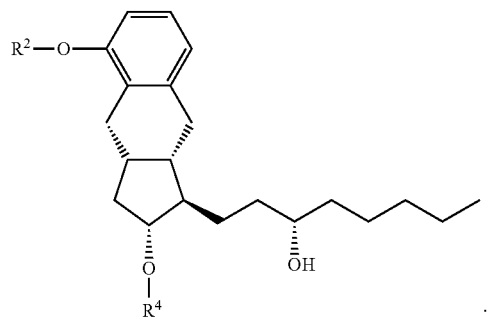

IVb where in the formula the meaning of $R^2$ is as defined above and
$R^4$ represents a protective group containing silicium atom, trityl-, methoxytrityl-, p-methoxybenzyl-, methoxymethyl-, ethoxymethyl-, methoxyethoxymethyl-, methylthiomethyl-, benzyloxymethyl- or $C_{1-13}$ acyl- group, with the proviso that the $R^4$ protective group must be selectively removable from $R^2$—is removed.

Hydrogenation of the compound of the general formula III is carried out in the presence of catalyst.

As catalyst platinum oxide, Pd/C catalyst, preferably Pd/C catalyst may be applied.

The compounds of the general formula III

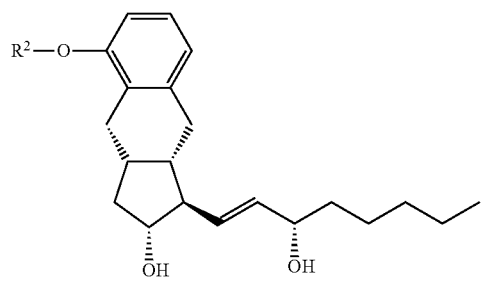

III are novel—where in the formula
$R^2$ represents —$(CH_2)$ Y, where
Y stands for hydrogen atom, halogen atom, phenyl-, —$OR^5$ or —$COOR^5$ group, wherein $R^5$ means $C_{1-4}$ alkyl-, tetrahydropyranyl-, tri($C_{1-4}$)alkylsilyl- or ($C_{1-4}$)alkyl-di($C_{6-10}$)arylsilyl- group and n stands for 1, 2, 3, 4—, with the proviso that $R^5$ in —COOR$^5$ cannot stay for $C_{1-4}$ alkyl.

The compounds of the general formula III can be prepared so that the $R^4$ protective group of the compounds of the general formula IVa.

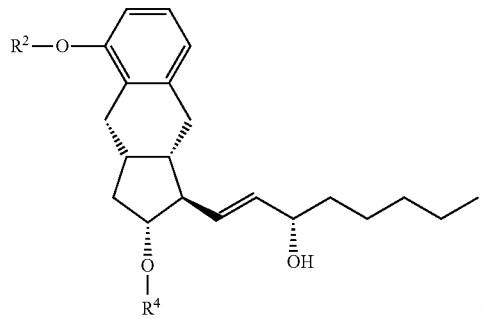

IVa where in the formula
$R^2$ has the meaning as defined above and
$R^4$ represents a protective group containing silicium atom, trityl-, methoxytrityl-, p-methoxybenzyl-, methoxymethyl-, ethoxymethyl-, methoxyethoxymethyl-, methylthiomethyl-, benzyloxymethyl- or $C_{1-13}$ acyl- group, with the proviso that the $R^4$ protective group must be selectively removable from $R^2$-$R^4$ is removed.

The $R^4$ protective group containing the silicium atom is preferably phenyldimethylsilyl-, triethylsilyl-, triisopropylsilyl-, tert-butyldimethylsilyl- or tert-butyldiphenylsilyl-group.

Removal of the $R^4$ protective group is carried out by methanolysis, in the presence of base.

The compounds of the general formula IV

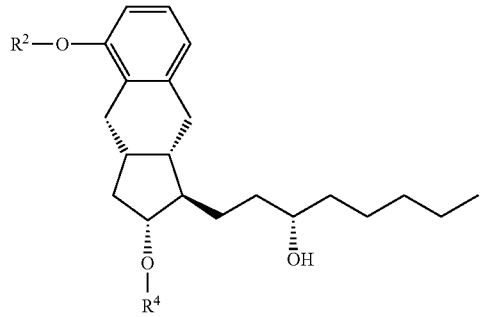

IV where in the formula
$R^2$ represents —(CH$_2$)$_n$Y, where
Y stands for hydrogen atom, halogen atom, phenyl-, nitrile-, —OR$^5$ or —COOR$^5$ group, wherein R$^5$ means $C_{1-4}$ alkyl-, tetrahydropyranyl-, tri($C_{1-4}$)alkylsilyl- or ($C_{1-4}$)alkyl-di($C_{6-10}$)arylsilyl- group,
n stands for 1, 2, 3, 4,
$R^4$ represents a protective group containing silicium atom, trityl-, methoxytrityl-. p-methoxybenzyl-, methoxymethyl-, ethoxymethyl-, methoxyethoxymethyl-, methylthiomethyl-, benzyloxymethyl- or $C_{1-13}$ acyl- group, with the proviso that the $R^4$ protective group must be selectively removable from $R^2$, and the dotted line represents single or double bond—are novel compounds.

The novel compounds of the general formula IVa.

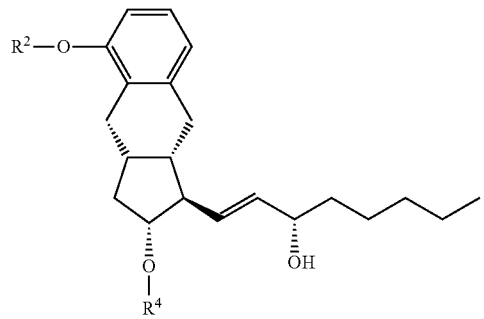

IVa where in the formula
$R^2$ represents —(CH$_2$)$_n$Y, where
Y stands for hydrogen atom, halogen atom, phenyl-, nitrile-, —OR$^5$ or —COOR$^5$ group, wherein
$R^5$ means $C_{1-4}$ alkyl-, tetrahydropyranyl-, tri($C_{1-4}$)alkylsilyl- or ($C_{1-4}$)alkyl-di($C_{6-10}$)arylsilyl- group,
n stands for 1, 2, 3, 4, and
$R^4$ represents a protective group containing silicium atom, trityl-, methoxytrityl-, p-methoxybenzyl-, methoxymethyl-, ethoxymethyl-, methoxyethoxymethyl-, methylthiomethyl-, benzyloxymethyl- or $C_{1-13}$ acyl- group, with the proviso that the $R^4$ protective group must be selectively removable from $R^2$,
can be prepared so that a compound of the general formula V

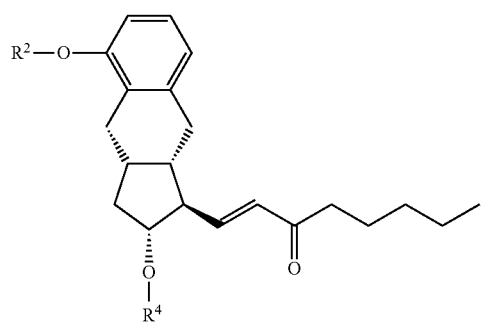

V where in the formula the meanings of $R^2$ and $R^4$ are as defined above—is selectively reduced.

Reduction of the compound of formula V is performed with borane compound, in the presence of oxazaborolidine catalyst.

As borane compound catecholborane, borane-diethylaniline complex, borane-dimethyl sulfide complex, preferably borane-dimethyl sulfide complex is applied.

The compounds of the general formula V are novel.

The novel compounds of the general formula V can be prepared so that a compound of the general formula Via.

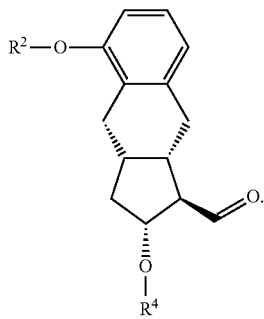

VIa

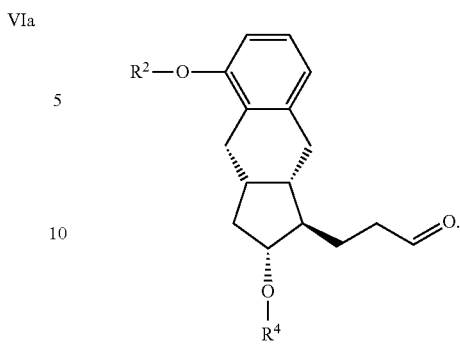

VIb where in the formula the meanings of $R^2$ and $R^4$ are as defined above—are reacted in Wittig reaction with the compound of general formula

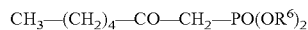

$CH_3-(CH_2)_4-CO-CH_2-PO(OR^6)_2$ where in the formula $R^6$ represents $C_{1-4}$ alkyl- or phenyl- group.

The novel compounds of the general formula IVb.

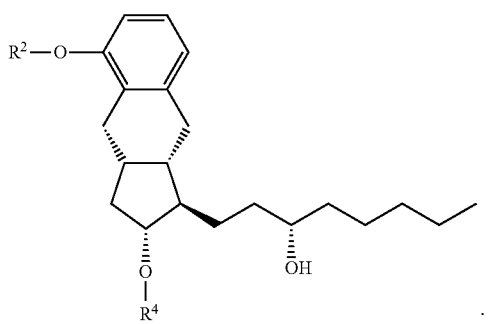

IVb where in the formula $R^2$ represents $-(CH_2)_nY$, where

Y stands for hydrogen atom, halogen atom, phenyl-, nitrile-, $-OR^5$ or $-COOR^5$ group, wherein $R^5$ means $C_{1-4}$ alkyl-, tetrahydropyranyl-, tri($C_{1-4}$)alkylsilyl- or ($C_{1-4}$)alkyl-di($C_{6-10}$)arylsilyl- group, n stands for 1, 2, 3, 4, and $R^4$ represents a protective group containing silicium atom, trityl-, methoxytrityl-, p-methoxybenzyl-, methoxymethyl-, ethoxymethyl-, methoxyethoxymethyl-, methylthiomethyl-, benzyloxymethyl- or $C_{1-13}$ acyl- group, with the proviso that the $R^4$ protective group must be selectively removable from $R^2$, can be prepared so that a compound of the general formula VIb.

where in the formula $R^2$ and $R^4$ have the meanings as defined above —, is reacted with an organic metal reagent, in the presence of chiral catalyst.

As organic metal reagent dipentylzinc or pentylmagnesium bromide, as chiral catalyst (2S)-3-exo-(morpholino) isoborneol may be applied.

The compounds of the general formulae VIa. and VIb. are novel.

The compounds of the general formula VI

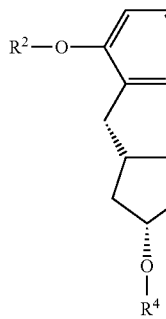

VI where in the formula $R^2$ represents $-(CH_2)_nY$, where

Y stands for hydrogen atom, halogen atom, phenyl-, nitrile-, $-OR^5$ or $-COOR^5$ group, wherein $R^5$ means $C_{1-4}$ alkyl-, tetrahydropyranyl-, tri($C_{1-4}$)alkylsilyl- or ($C_{1-4}$)alkyl-di($C_{6-10}$)arylsilyl- group, n stands for 1, 2, 3, 4, $R^4$ represents a protective group containing silicium atom, trityl-, methoxytrityl-, p-methoxybenzyl-, methoxymethyl-, ethoxymethyl-, methoxyethoxymethyl-, methylthiomethyl-, benzyloxymethyl- or $C_{1-13}$ acyl- group, with the proviso that the $R^4$ protective group must be selectively removable from $R^2$, and x represents 0 or 2—can be prepared so that a compound of the general formula VII

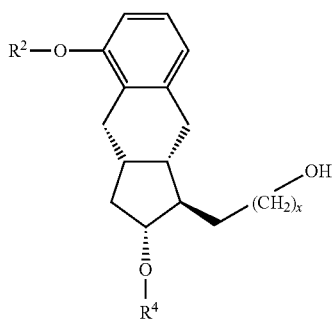

VII where in the formula x, $R^2$ and $R^4$ have the meanings as defined above-, is oxidized.

Oxidation of the compound of formula VII is carried out with PCC (pyridinium chlorochromate) or under Swern conditions (oxalyl chloride/DMSO/organic base) or with TEMPO (2,2,6,6-tetramethyl-1-piperidinyloxy free radical), or under Pfitzner-Moffat conditions (DCC (dicyclohexylcarbodiimide)/DMSO/acid).

The compounds of the general formula VII are novel.

The novel compounds of the general formula VII can be prepared so that the $R^1$ protective group of a compound of the general formula VIII

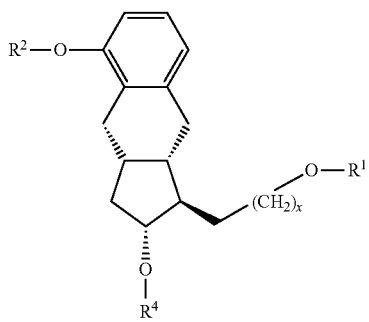

VIII where in the formula $R^1$ represents a protective group containing silicium atom, tetrahydropyranyl-, trityl-, methoxymethyl, -ethoxymethyl-, methoxyethoxymethyl-, methylthiomethyl-, benzyloxymethyl- group, with the proviso that the $R^1$ protective group must be selectively removable from $R^2$ and $R^4$ x, $R^2$ and $R^4$ have the meanings as defined above —, is removed in acidic medium.

The protective group $R^1$ which contains silicium atom is preferably phenyldimethylsilyl-, triethylsilyl-, triisopropylsilyl-, tert-butyldimethylsilyl- or tert-butyldiphenylsilyl- group.

The compounds of the general formula VIII are novel.

The novel compounds of the general formula VIII can be prepared so that a compound of the general formula IX.

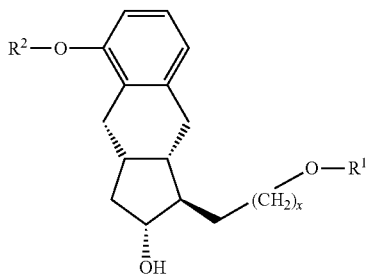

IX where in the formula x, $R^1$ and $R^2$ have the meanings as defined above-, is reacted with a compound suitable for the introduction of a group $R^4$.

As the compound suitable for the introduction of group $R^4$ preferably p-phenylbenzoyl chloride is applied.

The compounds of the general formula IX are novel.

The novel compounds of the general formula IX can be prepared so that a compound of the general formula X

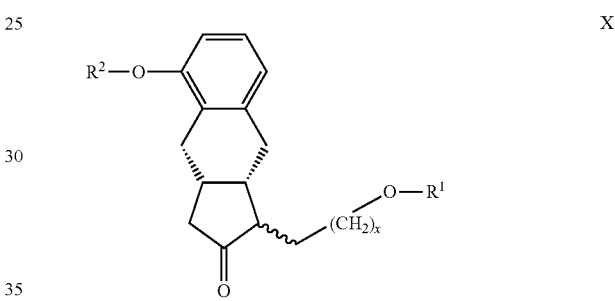

X where in the formula x, $R^1$ and $R^2$ have the meanings as defined above—, is reduced.

Reduction of the compound of the general formula X can be carried out with diisobutylaluminum hydride, lithium aluminum hydride, aluminum isopropylate, or sodium borohydride, preferably sodium borohydride.

The novel compounds of the general formula X can be prepared so that a compound of the general formula XI

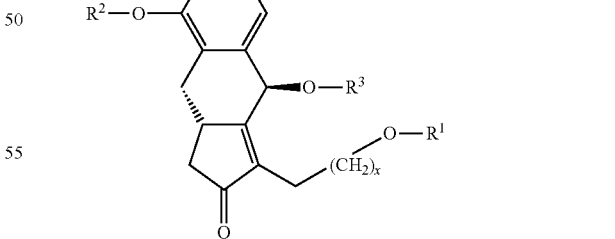

XI where in the formula x, $R^1$ and $R^2$ have the meanings as defined above, $R^3$ represents a protective group containing silicium atom, tetrahydropyranyl-, trityl-, methoxymethyl, -ethoxymethyl-, methoxyethoxymethyl-, methylthiomethyl-, benzyloxymethyl- or $C_{1-13}$ acyl- group- is catalytically hydrogenated, and in the case where x=0 isomerized.

For the hydrogenation of the compound of formula XI as catalyst Pd/C catalyst or platinum oxide, preferably Pd/C catalyst may be used.

The compounds of the general formula XI are novel.

The novel compounds of the general formula XI can be prepared so that a compound of the general formula XII

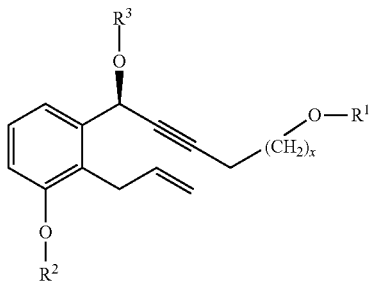

XII where in the formula x, $R^1$, $R^2$ and $R^3$ have the meanings as defined above—is subjected to intramolecular cyclisation.

For the intramolecular cyclisation favourably the Pauson-Khand cyclisation method is applied. The Pauson-Khand cyclisation is performed using dicobalt octacarbonyl.

Dicobalt octacarbonyl may be applied in equimolar, or less than equimolar or more than equimolar ratios.

The reaction is preferably performed in carbon monoxide atmosphere using ethyl acetate as solvent.

The novel compounds of the general formula XII can be prepared so that a compound of the general formula XIII

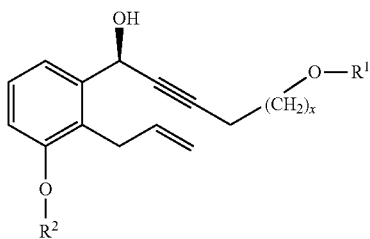

XIII where in the formula x, $R^1$ and $R^2$ have the meanings as defined above—is reacted with a compound suitable for the introduction of group $R^3$.

The novel compounds of the general formula XIII can be prepared so that a.) a compound of the general formula XIV

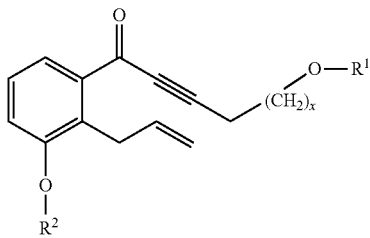

XIV where in the formula x, $R^1$ and $R^2$ have the meanings as defined above—is selectively reduced, or b.) a compound of the general formula XVI

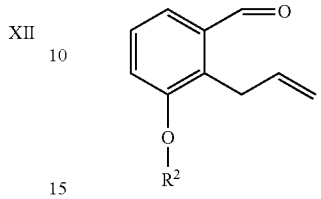

XVI where in the formula $R^2$ has the meaning as defined above —, is reacted with a compound of the general formula XVII

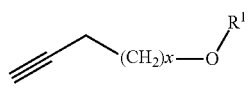

XVII where in the formula $R^1$ and x have the meanings as defined above—in the presence of a chiral base and zinc salt.

Reduction of the compound of the general formula XIV is carried out with borane compound, in the presence of chiral oxazaborolidine catalyst.

As borane compound, borane-dimethyl sulfide complex, catecholborane or borane-diethylaniline complex, preferably borane-dimethyl sulfide complex, as chiral base, chiral aminoalcohols or diamines, preferably (+)-N-methylephedrine may be applied.

In the reaction of the compounds of the general formulae XVI and XVII, as zinc salt preferably zinc triflate may be applied.

The novel compounds of the general formula XIV can be prepared so that a compound of the general formula XV

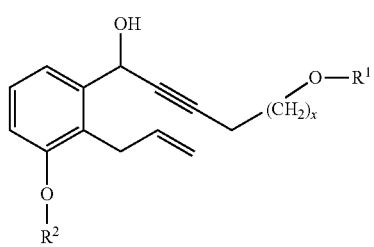

XV where in the formula x, $R^1$ and $R^2$ have the meanings as defined above —, is oxidized.

Oxidation of the compound of formula XV is carried out with PCC (pyridinium chlorochromate) or under Swern reaction conditions (oxalyl chloride/DMSO/organic base).

The novel compounds of the general formula XV can be prepared so that a compound of the general formula XVI

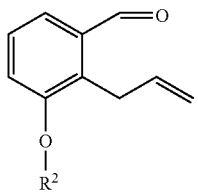

where in the formula
R² has the meaning as defined above —, is reacted with a compound of the general formula XVII

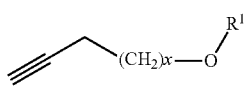

where in the formula
R¹ has the meaning as defined above and x is 0 or 2-, in the presence of Grignard reagent.

As Grignard reagent methyl-, ethyl-, propyl-, butyl-, cyclohexyl-magnesium bromide, preferably methylmagnesium bromide may be applied.

A further subject of our invention is novel method for the preparation of the amorph, anhydrate, monohydrate and polyhydrate salts of treprostinil of formula I given with bases

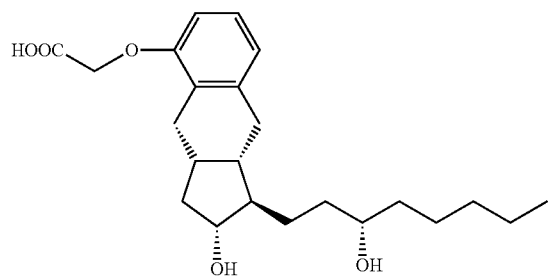

Treprostinil salts, among them treprostinil sodium salt, in general form are described in WO99/25357 (United Therapeutics), without characterizing them with chemical-physical date. First time in Exhibit 1-Applicant's submission to EP1628654 (United Therapeutics) is the melting point of treprostinil sodium salt mentioned as being 56° C.

WO 2012/088607 (Alphora) describes a new process for the preparation of treprostinil sodium salt in that treprostinil is dissolved in a water-miscible organic solvent to form treprostinil solution, than the solution is reacted with an aqueous solution containing an alkali metal cation to form a reaction mixture containing the treprostinil salt, the salt is allowed to crystallization and the salt formed is collected.

According to the present invention the amorph, anhydrate, monohydrate and polyhydrate salts of treprostinil of formula I given with bases are prepared in a way that treprostinil is dissolved in polar solvent, the solid base is added to the solution, the reaction mixture is agitated and when salt formation is completed the solution is filtered, concentrated, the solvent of the concentrate is exchanged for the organic solvent of the crystallisation and the treprostinil salt is crystallized.

To prepare the salts of treprostinil of formula I. given with bases, as polar solvent $C_{1-5}$ open-chain or branched organic alcohol, preferably ethanol, as base a solvent-free organic or inorganic base which contains the cation of the desired salt, for example an organic or inorganic base containing alkali metal cation or alkali earth-metal cation, e.g. sodium carbonate monohydrate, sodium hydrogen carbonate or sodium methylate, preferably a hydrate of sodium carbonate may be applied.

The reaction mixture is agitated in an inert atmosphere until salt formation is completed.

According to one embodiment of the invention as organic solvent of the crystallisation aqueous ether-, ester- or ketone-type solvent, i.e. as ether-type solvent an open-chain or branched simple or mixed ether, preferably tert-butyl methyl ether may be applied.

Crystallisation is preferably carried out at a temperature between 50° C.-(-40° C.).

As a result of the above method using an organic or inorganic base containing sodium cation white crystalline treprostinil sodium salt monohydrate (Form A) is obtained which is a new compound.

According to an another embodiment of the invention if the organic solvent of crystallisation is a water-free ether-, ester- or ketone-type solvent, then the amorphous treprostinil sodium salt is obtained which is a new compound.

According to the invention treprostinil sodium salt anhydrate (Form B) can be prepared by carrying out the above process till the crystallisation step and performing the crystallisation at 60-100° C. or in vacuum. Another possible method is that the sodium salt monohydrate is taken up and stirred at 60-90° C. for 1-6 hours in a solvent which does not, or only sparingly dissolves the salt. As solvent preferably hexane, heptane, toluene, ethyl acetate may be applied.

If treprostinil sodium salt monohydrate or the anhydrate is kept in an atmosphere of 60% moisture content for 48 hours, or on the air for 5-8 days, then the novel treprostinil sodium salt polyhydrate (Form C) is obtained.

DSC and X-ray powder diffraction (XRPD) spectra of the different forms are shown in the FIGS. 1-9.

BRIEF DESCRIPTION OF THE SEVERAL VIEWS OF THE DRAWINGS

FIG. 1 shows a DSC diagram of treprostinil sodium salt (amorphous form).

FIGS. 2 and 3 show DSC diagrams of treprostinil sodium salt monohydrate.

FIGS. 4 and 5 show DSC diagrams of treprostinil sodium salt anhydrate.

FIG. 6 shows a DSC diagram of treprostinil sodium salt polyhydrate.

FIG. 7 shows an XRPD diagram of treprostinil sodium salt monohydrate.

FIG. 8 shows an XRPD diagram of treprostinil sodium salt anhydrate.

FIG. 9 shows an XRPD diagram of treprostinil sodium salt polyhydrate.

These above mentioned salt forms show suitable stability and applicability for the preparation of pharmaceutical formulations.

In a preferred embodiment of the invention:

The propargyl alcohol is protected with methoxymethyl group.

The protected propargyl alcohol (XVII) is reacted with 2-allyl-3-methoxybenzaldehyde (XVI) in the presence of methylmagnesium bromide Grignard reagent. The thus obtained racemic alcohol (XV) is oxidized.

The oxidation is carried out e.g. by the Swern oxidation method or by oxidation with chromium(VI).

Stereoselective reduction of the ketone XIV results the chiral alcohol XIII.

The stereoselective reduction may be carried out e.g. with borane-dimethyl sulfide complex in the presence of Corey catalyst.

The chiral alcohol XIII may directly be prepared by reacting the protected propargyl alcohol (XVII) with 2-allyl-3-methoxybenzaldehyde (XVI) in the presence of chiral base, e.g. (+)-N-methylephedrine and zinc triflate.

The hydroxyl group is protected with tert.-butyldimethylsilyl group, the silyl ether (XII) is cyclized in Pauson-Khand reaction in the presence of dicobalt octacarbonyl. As a result of the reaction the tricycle (XI) is formed by incorporation of a CO molecule.

The cyclisation can be carried out using equimolar amount of dicobalt octacarbonyl, or more preferably with catalytic amount of dicobalt octacarbonyl under carbon monoxide atmosphere.

The silyloxy group is removed by catalytic hydrogenation and the double bond of the five-membered ring is saturated. The stereostructure of the tricyclic ketone (X) is formed by isomerisation with base (diazabicyclononane/ethanol).

The oxo group is reduced (IX), the resulting secondary hydroxyl group is protected with p-phenylbenzoyl (PPB) group (VIII).

The methoxymethyl protecting group is cleaved by treatment with acid (VII).

The primary hydroxyl group is oxidized (VI).

The resulting aldehyde VI is, without isolation, reacted with 2-oxo-heptylphosphonate.

The thus obtained enone V is reduced by a selective reduction method, e.g. with borane-dimethyl sulfide complex, in the presence of Corey catalyst.

The p-phenylbenzoyl protecting group of the resulting compound of formula IV is removed by methanolysis, in the presence of base.

Saturation of the double bond of the enol of formula III by catalytic hydrogenation results the benzindene derivative of formula II.

According to another preferred embodiment of the invention 2-pent-4-ynoxytetrahydropyran is used as starting material, instead of the protected propargyl alcohol. The side-chain is built out stereoselectively in the presence of chiral catalyst, by reaction with dipentylzinc or pentylmagnesium bromide.

The benzindene of formula II is the key-intermediate to treprostinil, it is transformed to treprostinil by known chemical steps.

The first chemical step is the cleavage of the methyl ether. Removal of the methyl group is carried out with a mercaptan, in the presence of aluminum halide.

As for aluminum halide aluminum trichloride, as for mercaptan, instead of the commonly used ethanethiol, the odourless dodecanethiol has been chosen for the preparation of the trihydroxy derivative. (Scheme 6)

Scheme 6

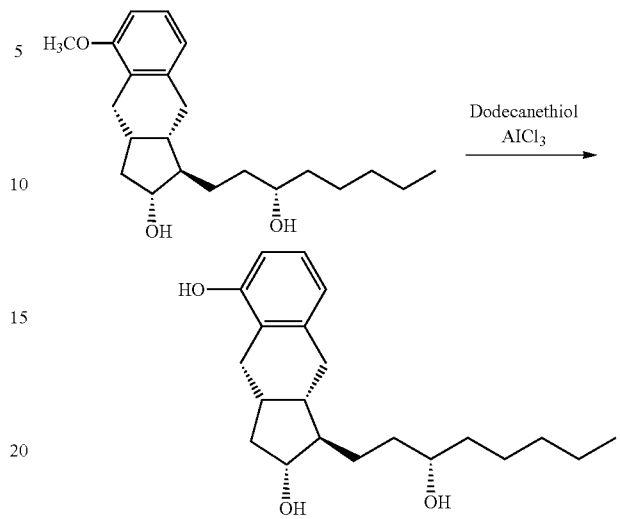

The next step is the alkylation of the aromatic hydroxyl group with a haloacetic acid ester, e.g. bromo- or chloro-acetic acid ethyl- or methyl ester. In our process the trihydroxy derivative is alkylated with bromoacetic acid ethyl ester. (Scheme 7)

Scheme 7

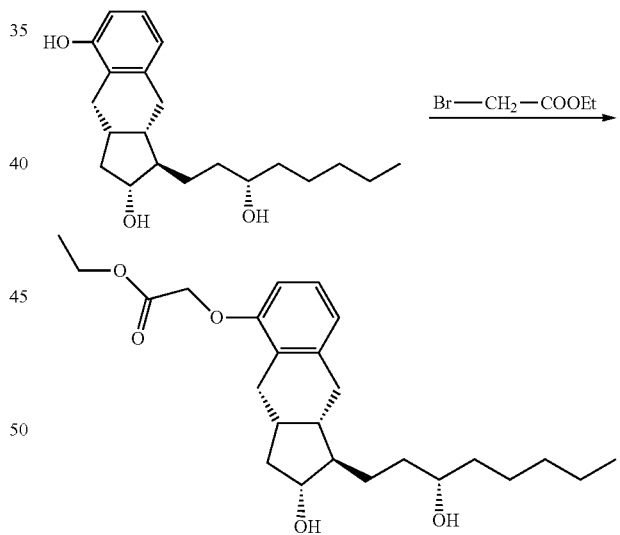

Hydrolysis of the ethyl ester derivative results crystalline treprostinil.

In our method the hydrolysis is carried out with aqueous sodium hydroxide solution, in tetrahydrofuran.

When the reaction is completed, the reaction mixture is washed with tert-butyl methyl ether. The pH of the aqueous phase is set to pH≤3 by addition of aqueous acid solution. Treprostinil is extracted with tert-butyl methyl ether, the product solution is washed and evaporated. (Scheme 8)

Scheme 8

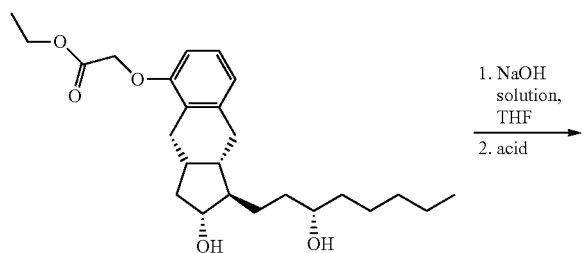

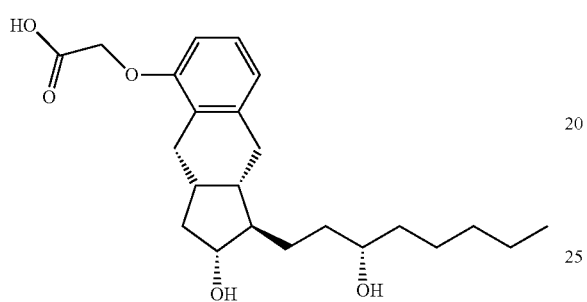

For the salt formation, treprostinil is dissolved in ethanol and solid sodium carbonate monohydrate is added to it. (Scheme 9).

Scheme 9

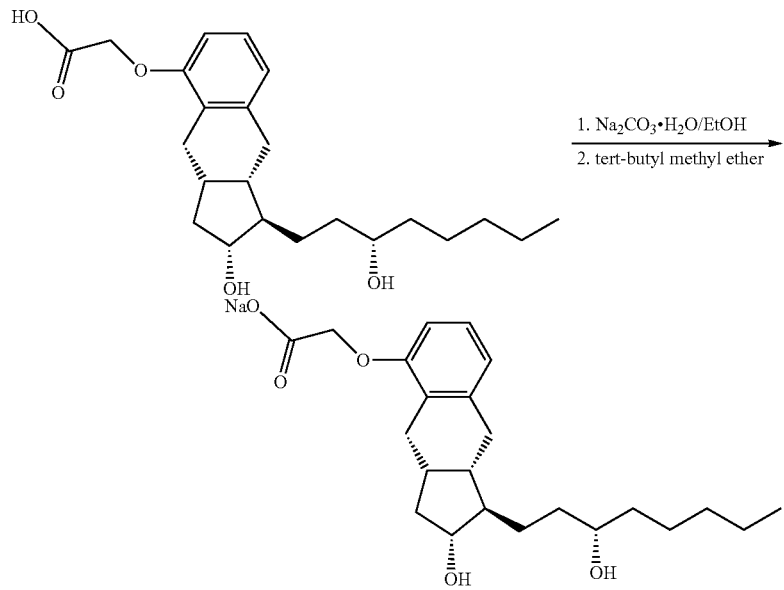

The solution is filtered through microfilter, the ethanol is exchanged for tert-butyl methyl ether which has been saturated with water and the treprostinil sodium salt is crystallized at room temperature.

The advantages of the method according to the invention:
The formation of the benzindene tricycle does not require expensive chiral starting material.
The construction of the side-chain is realized by well-scalable and robust chemical steps (Wittig- or modified Wittig reaction) which are used in the prostaglandin chemistry, or carried out stereoselectively by use of organic metal compound, in the presence of chiral catalyst.

The enone obtained in the Wittig reaction can be transformed into the desired enantiomer in stereoselective reaction, in a good yield.

The applied p-phenylbenzoyl group (PPB-group) is well detectable in UV.

The PPB-group enhances the crystallisation ability of the intermediates and thus helps their purification.

Schemes 10, 11, 12, and 13 are demonstrated below:

Schemes 10, 11, 12, 13:

Scheme 10

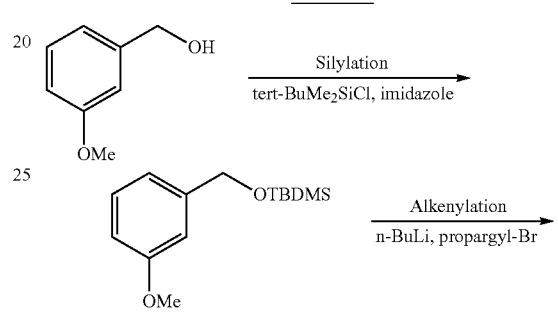

-continued

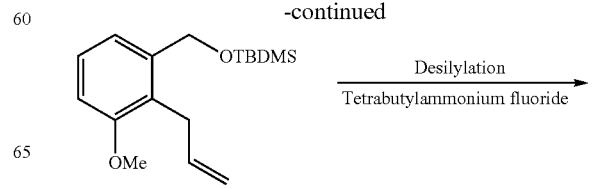

Scheme 11
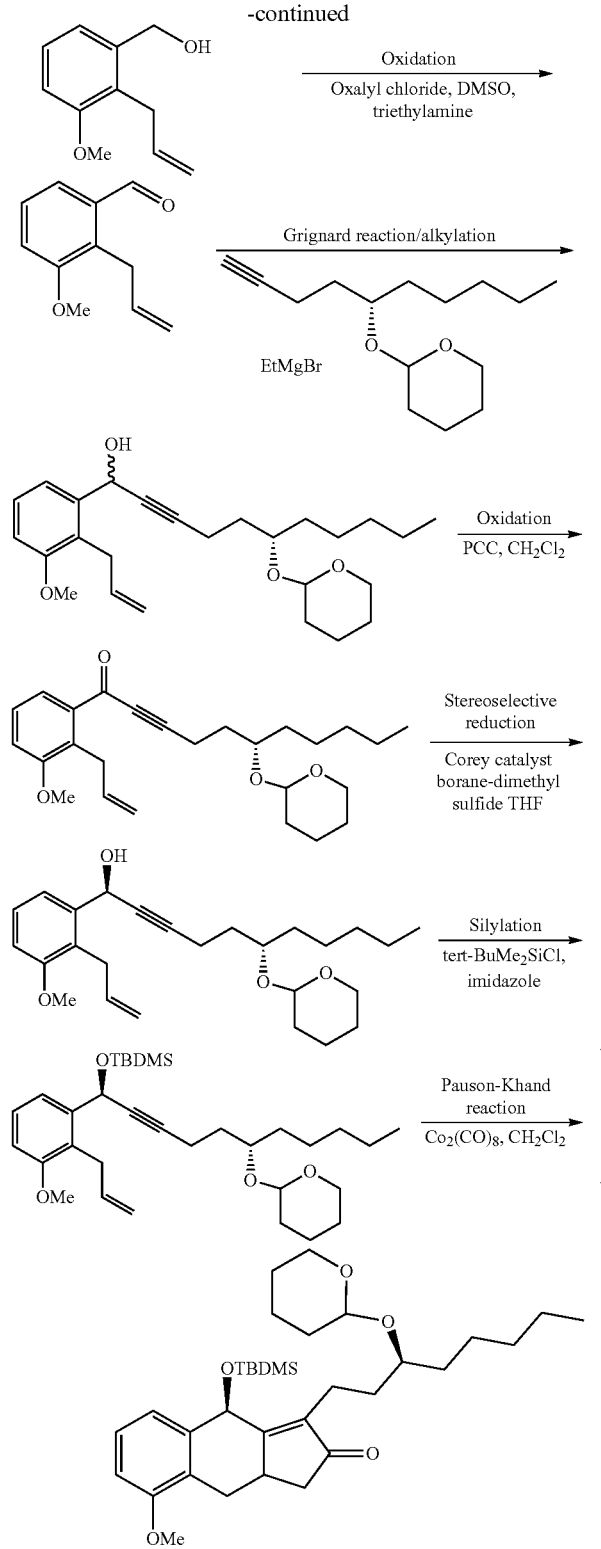
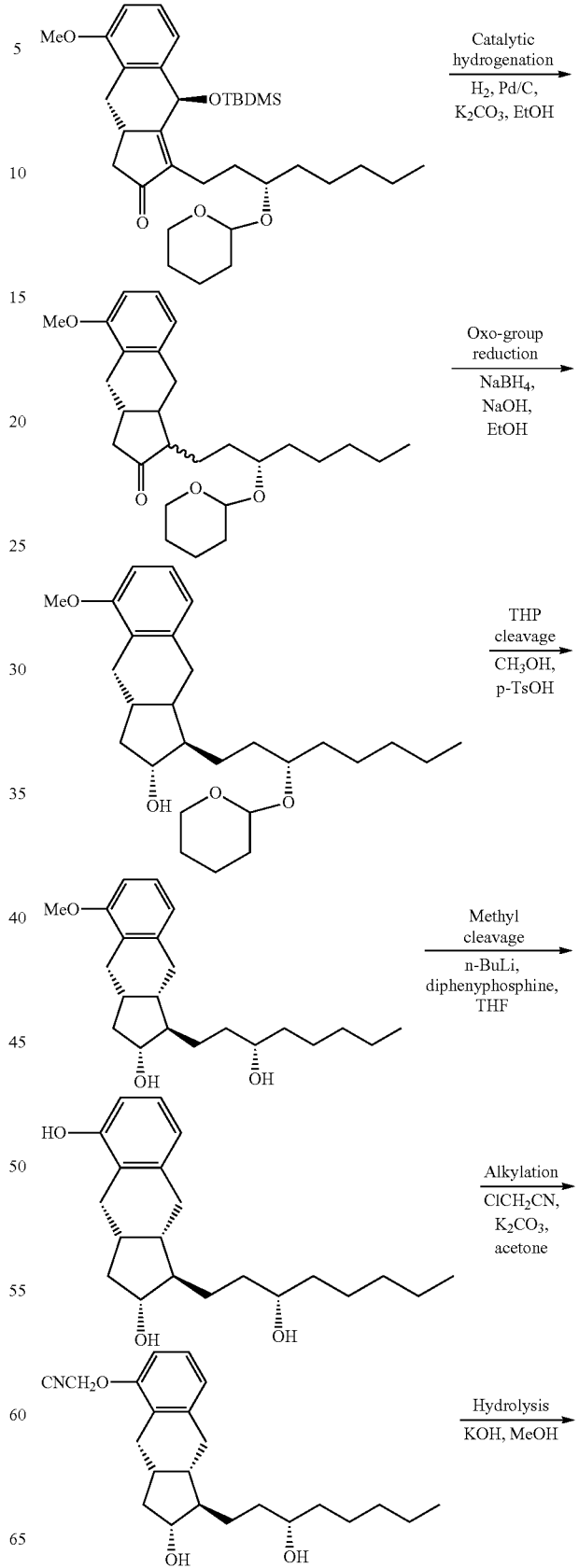
TBDMS = tertiary-butyldimethylsilyl
PCC = pyridinium chlorochromate
Corey catalyst:
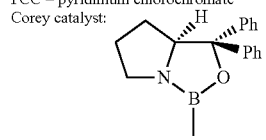

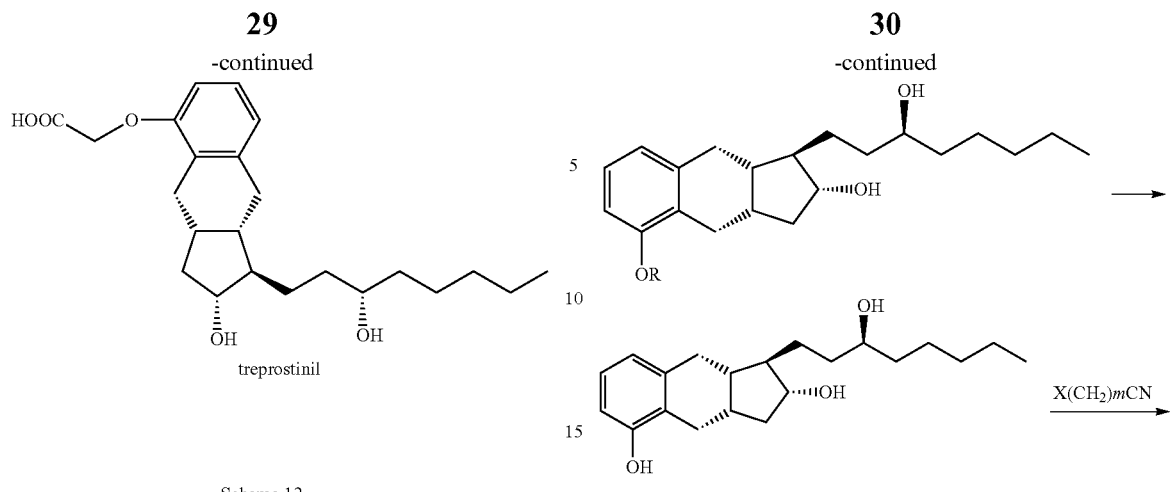
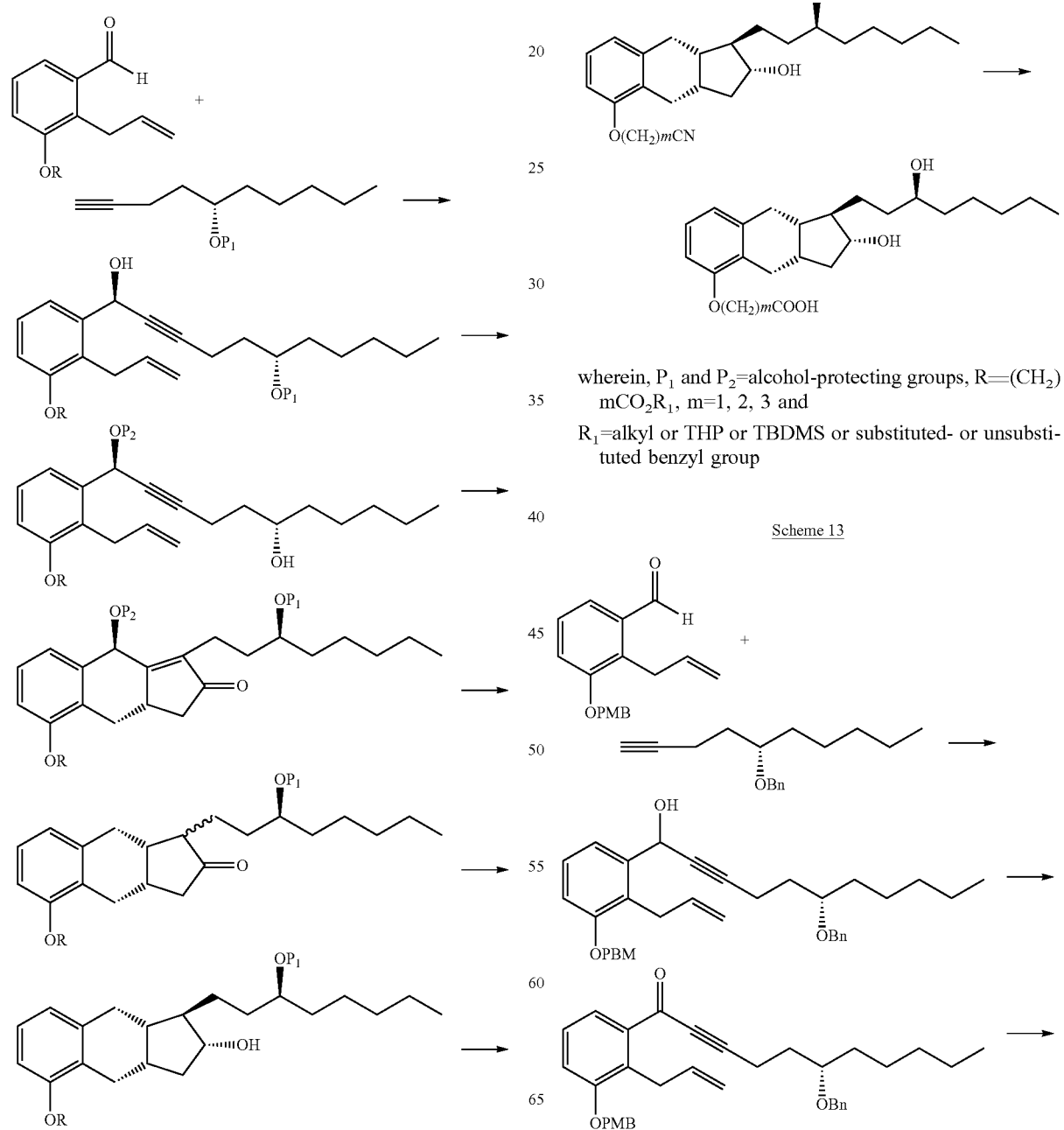
wherein, P₁ and P₂=alcohol-protecting groups, R=(CH₂)mCO₂R₁, m=1, 2, 3 and
R₁=alkyl or THP or TBDMS or substituted- or unsubstituted benzyl group

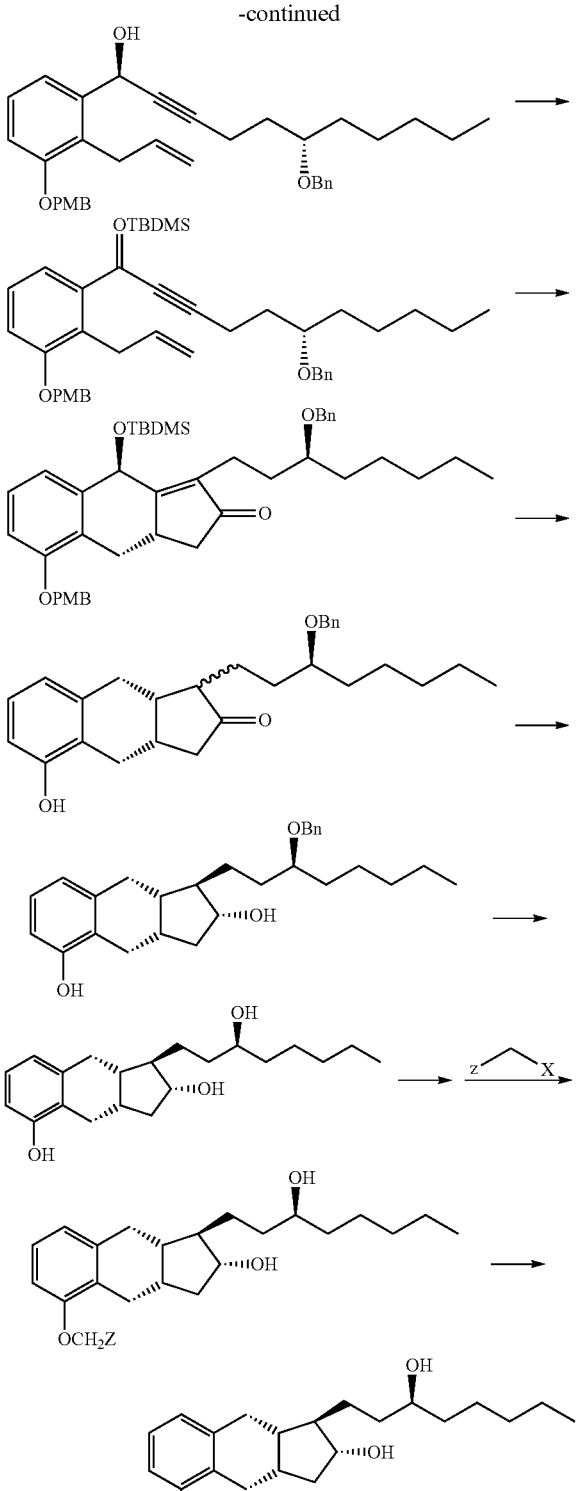

wherein PMB=p-methoxybenzyl, Bn=benzyl,
Z=carboxyl group or carboxylic acid derivative,
X=halogen atom Further details of the processes according to the invention are demonstrated by the examples, without limiting the invention to the examples.

EXAMPLES

Example 1

1a.)

Preparation of 3-(Methoxymethoxy)-1-propyne (MOM-propynol, TREPO-1)

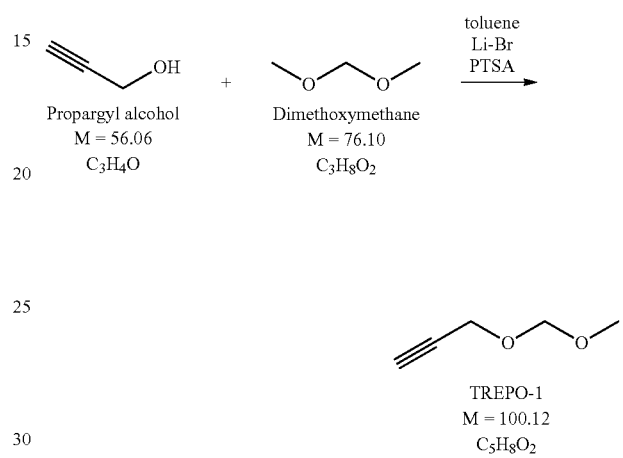

2.27 ml of propargyl alcohol and 8 ml of dimethoxymethane are dissolved in 8 ml of toluene. To the solution 0.66 g of p-toluenesulfonic acid and 0.33 g of lithium bromide are added. The reaction mixture is stirred at room temperature for 20 hours, washed with sodium hydrogen carbonate solution and with water. The organic phase is dried and the solution is taken into the next step without evaporation.

Yield: cca. 2 g (50%) of product, in solution.

NMR data: (DMSO-d6), 1H NMR (500 MHz): 4.62 ppm (H-4, 2), s; 4.16 ppm (H-3, 2), d, J=2.3 Hz; 3.41 ppm (H-1, 1), t, J=2.3 Hz; 3.26 ppm (H-5, 3), s; 13C NMR (125.8 MHz): 94.15 ppm (C-4), 79.90 ppm (C-2), 76.97 ppm (C-1), 54.97 ppm (C-5), 53.60 ppm (C-3).

1b.) Preparation of 1-(2-Allyl-3-methoxyphenyl)-4-methoxymethoxy-but-2-yn-1-ol (TREP-1) (Non-Selective Alkynylation)

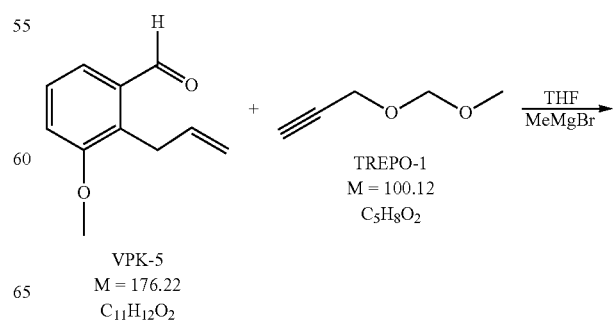

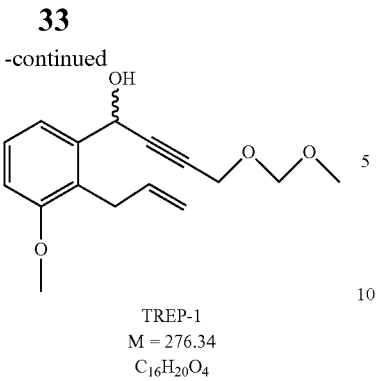

TREP-1
M = 276.34
C₁₆H₂₀O₄

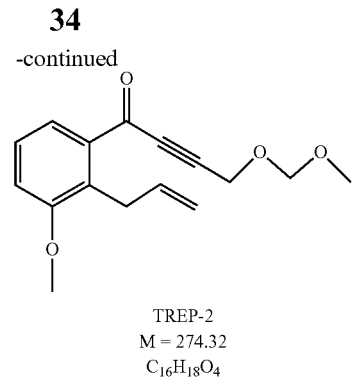

TREP-2
M = 274.32
C₁₆H₁₈O₄

64 g (0.64 mol) of 3-(methoxymethoxy)-1-propyne (TREPO-1) is dissolved in nitrogen atmosphere in 600 ml of water-free tetrahydrofuran and the solution is heated to 60-65° C. To the reaction mixture 220 ml of ethylmagnesium bromide solution (3M solution in diethyl ether) (0.66 mol) is added slowly. At the end of the addition the reaction mixture is heated at reflux temperature for 45 minutes then, after cooling to 0-5° C., the solution of 100 g of 2-allyl-3-methoxybenzaldehyde (VPK-5) (0.57 mol) in 100 ml of water-free tetrahydrofuran is added dropwise. The mixture is stirred at room temperature. When the reaction is completed, the mixture is cooled to 0° C. and NaHSO₄ (sodium hydrogen sulfate) solution is added to it. After agitation the phases are separated, the aqueous layer is extracted with ethyl acetate. The united organic phase is washed with NaHCO₃ (sodium hydrogen carbonate) solution and dried over sodium sulfate. The drying material is filtered off, the filtrate solution is evaporated in vacuum. The crude product is taken into the next step, without purification.

Yield: 156.8 g (100%) of light brown oil.

NMR data: (CDCl3), 1H NMR (500 MHz): 7.32 ppm (H-6, 1), dd, J=7.8 Hz and 0.8 Hz; 7.24 ppm (H-5, 1), m (t), J=7.9 Hz, 6.87 ppm (H-4, 1), d (dd), J=7.8 Hz and ~1.0 Hz; 5.98 ppm (H-14, 1), ddt, J=17.1 Hz, 10.2 Hz and 5.8 Hz; 5.67 ppm (H-7, 1), m (dt), J=5.4 Hz and 1.6 Hz; 4.985 ppm (H-15a, 1), dq, J=10.1 Hz and 1.6 Hz; 4.93 ppm (H-15b, 1), dq, J=17.1 Hz and 1.8 Hz; 4.69 ppm (H-11, 2), s; 4.28 ppm (H-10, 2), d, J=1.7 Hz; 3.82 ppm (H-16, 3), s; 3.61 ppm (H-13a, 1), ddt, J=15.7 Hz, 5.8 Hz and 1.6 Hz; 3.55 ppm (H-13b, 1), ddt, J=15.7 Hz, 5.8 Hz and 1.6 Hz; 3.36 ppm (H-12, 3), s; 2.55 ppm (OH-7, 1), d, J=5.5 Hz; 13C NMR (125.8 MHz): 157.75 ppm (C-3), 139.93 ppm (C-1), 136.99 ppm (C-14), 127.59 ppm (C-5), 125.97 ppm (C-2), 119.31 ppm (C-6), 114.89 ppm (C-15), 110.93 ppm (C-4), 94.93 ppm (C-11); 86.25 ppm (C-8), 82.01 ppm (C-9), 61.98 ppm (C-7), 55.88 ppm (C-16); 55.63 ppm (C-12), 54.59 ppm (C-10), 29.53 ppm (C-13).

1c.) Preparation of I-(2-Allyl-3-methoxyphenyl)-4-methoxymethoxy-but-2-yn-1-one (TREP-2)

1c1. Method (Oxidation with PCC)

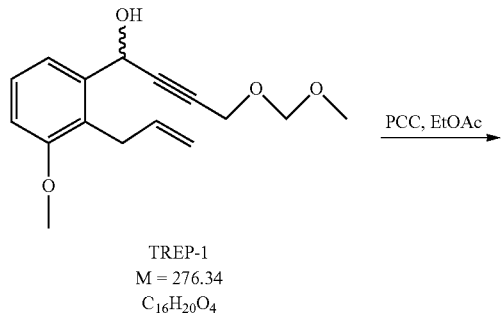

TREP-1
M = 276.34
C₁₆H₂₀O₄

200 g of silica gel is suspended in 1.5 l of ethyl acetate and 470 g (2.18 mol) of piridinium chlorochromate (PCC) is added to it. To the orange coloured suspension the solution of 150 g (0.54 mol) of TREP-1 in 0.5 l of ethyl acetate is added under stirring at 255° C. The reaction mixture is stirred at 35±5° C. At the end of the reaction diisopropyl ether and silica gel are added to the mixture. The suspension is filtered, the solid material is washed with ethyl acetate. The liquid filtrate is evaporated in vacuum. The crude product is purified by chromatography on silica gel using hexane:ethyl acetate eluent.

Yield: 88.1 g (59.2%) of light brown oil.

1c2. Method (Swern Oxidation)

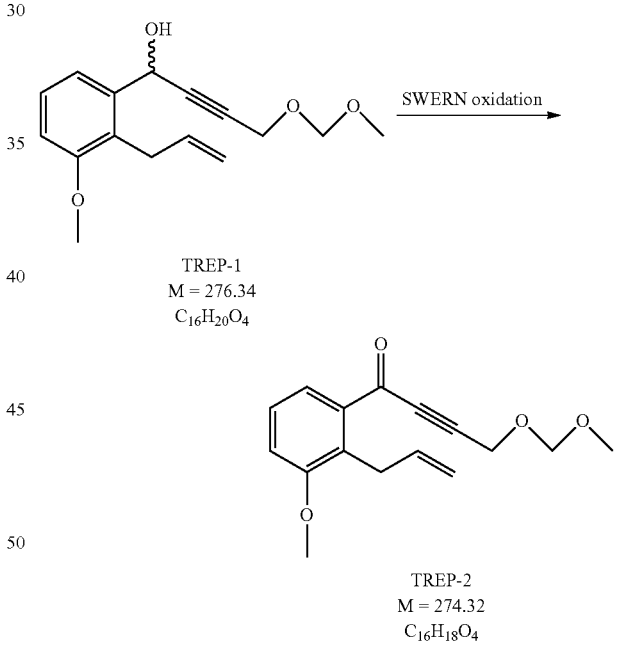

93 ml of oxalyl chloride is dissolved in 1.7 l of dichloromethane and reacted at −75/−85° C. with 148 ml of dimethyl sulfoxide (DMSO). To the mixture 179 g of TREP-1 is added at −75/−85° C. After 1 hour of stirring the reaction mixture is quenched with 621 ml of triethylamine and NaHSO₄ solution. The organic phase is extracted with dichloromethane, the united organic phase is washed with 1M NaHCO₃ solution. The crude product is purified by chromatography on silica gel.

Yield: 140 g (79%) of light brown oil.

NMR data: (CDCl3), 1H NMR (500 MHz): 7.75 ppm (H-6, 1), dd, J=7.8 Hz and 0.9 Hz; 7.305 ppm (H-5, 1), t, J=8.0 Hz; 7.08 ppm, (H-4, 1), d (dd), J=8.1 Hz and ~1.0 Hz; 5.96 ppm (H-14, 1), ddt, J=17.1 Hz, 10.1 Hz and 6.2 Hz; 5.01-4.92 ppm (H-15, 2), m (in: 4.98 ppm (H-15b, 1), dq, J=17.2 Hz and 1.7 Hz and 4.94 ppm (H-15a, 1), dq, J=10.1 Hz and 1.6 Hz); 4.745 ppm (H-11, 2), s; 4.45 ppm (H-10, 2), s; 3.85 ppm (H-16, 3), s; 3.78 ppm (H-13, 2), dt, J=6.2 Hz and 1.5 Hz; 3.40 ppm (H-12, 3), s; 13C NMR (125.8 MHz): 179.21 ppm (C-7), 158.21 ppm (C-3), 136.66 ppm (C-14); 133.60 ppm (C-1); 130.29 ppm (C-2), 126.98 ppm (C-5), 124.98 ppm (C-6), 115.42 ppm (C-4), 114.93 ppm (C-15), 95.38 ppm (C-11), 88.69 ppm (C-9), 85.73 ppm (C-8), 56.16 ppm (C-16), 55.87 ppm (C-12), 54.32 ppm (C-10), 29.78 ppm (C-13).

1d.) Preparation of (1 S)-1-(2-allyl-3-methoxyphenyl)-4-(methoxymethoxy)but-2-yn-1-ol (TREP-3)

1d1. Method (Selective Reduction)

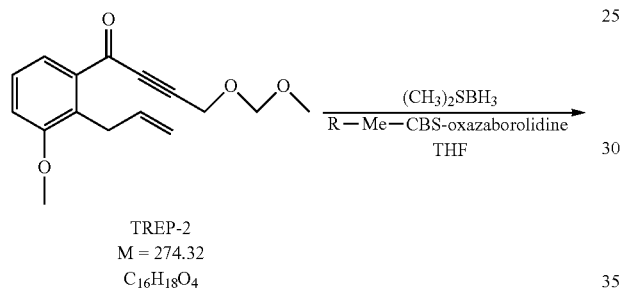

TREP-2
M = 274.32
C₁₆H₁₈O₄

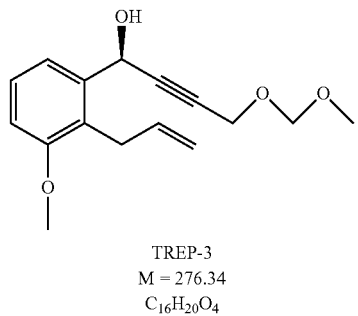

TREP-3
M = 276.34
C₁₆H₂₀O₄

In 600 ml of water-free tetrahydrofuran (THF) under nitrogen atmosphere 85 g of TREP-2 (0.31 mol) is dissolved. The solution is cooled to 0-5° C. and 370 ml (0.37 mol) of oxazaborolidine solution (1M solution in toluene) is added to it. The mixture is cooled to (−30° C. and 50 ml (0.52 mol) of borane-dimethyl sulfide complex is added to it dropwise at (−30° C. The reaction mixture is stirred at that temperature. At the end of the reaction the mixture is allowed to warm up to (−15)° C., 200 ml of methanol is carefully added (strong foaming and heat formation). After the methanol addition the reaction mixture is stirred for 30 minutes, then NH₄Cl solution is added at 0-5° C. and the quenched reaction mixture is extracted with 3×2.5 l of ethyl acetate. The united organic phase is washed with water and dried over sodium sulfate. The drying material is filtered off, the filtrate is evaporated.

Yield: 85.6 g (100%) of light brown oil.

1d2. Method (Selective Alkynylation)

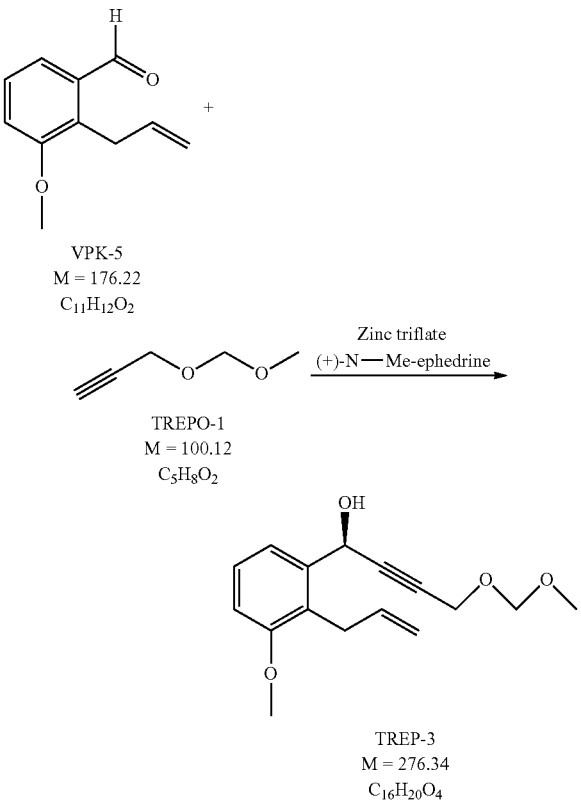

The reaction vessel is charged with 216 mg (0.59 mmol) of zinc triflate and 82 mg (0.45 mmol) of (+)-N-methyl-ephedrine, flushed with nitrogen gas for 10 minutes, then 1 ml of dist. toluene and 63 microl (0.45 mmol) of triethylamine are added. The reaction mixture is stirred at room temperature for 1 hour, then 250 microl (0.45 mmol) of TREPO-1 solution and after 15 minutes of stirring 24 microl of VPK-5 (2-allyl-3-methoxybenzaldehyde) (0.14 mmol) are added. Following 24 hours of stirring at room temperature, the reaction mixture is quenched with 1 ml of saturated NH₄Cl solution. The aqueous phase is extracted with toluene, the united organic phase is washed consecutively with NaHCO₃ solution and saturated NaCl solution, then evaporated.

Yield: 30 mg (78%) of light brown oil.

NMR data: (CDCl3), 1H NMR (500 MHz): 7.32 ppm (H-6, 1), dd, J=7.8 Hz and 0.9 Hz; 7.25 ppm (H-5, 1), m (t), J=8.0 Hz, 6.875 ppm (H-4, 1), d (dd), J=7.8 Hz and ~1.0 Hz; 5.98 ppm (H-14, 1), ddt, J=17.1 Hz, 10.2 Hz and 5.8 Hz; 5.68 ppm (H-7, 1), broad; 4.99 ppm (H-15a, 1), dq, J=10.1 Hz and 1.6 Hz; 4.93 ppm (H-15b, 1), dq, J=17.1 Hz and 1.8 Hz; 4.70 ppm (H-11, 2), s; 4.285 ppm (H-10, 2), d, J=1.8 Hz; 3.82 ppm (H-16, 3), s; 3.62 ppm (H-13a, 1), ddt, J=15.7 Hz, 5.8 Hz and 1.6 Hz; 3.545 ppm (H-13b, 1), ddt, J=15.7 Hz, 5.8 Hz and 1.6 Hz; 3.36 ppm (H-12, 3), s; 2.34 ppm (OH-7, 1), broad; 13C NMR (125.8 MHz): 157.79 ppm (C-3), 139.90 ppm (C-1), 137.06 ppm (C-14), 127.67 ppm (C-5), 125.99 ppm (C-2), 119.35 ppm (C-6), 114.96 ppm (C-15), 110.98 ppm (C-4), 94.99 ppm (C-11); 86.18 ppm (C-8), 82.13 ppm (C-9), 62.10 ppm (C-7), 55.93 ppm (C-16); 55.70 ppm (C-12), 54.62 ppm (C-10), 29.57 ppm (C-13).

1e.) Preparation of [(1 S)-1-(2-Allyl-3-methoxyphenyl)-4-(methoxymethoxy)but-2-ynoxy]-tert-butyldimethylsilane (TREP-4)

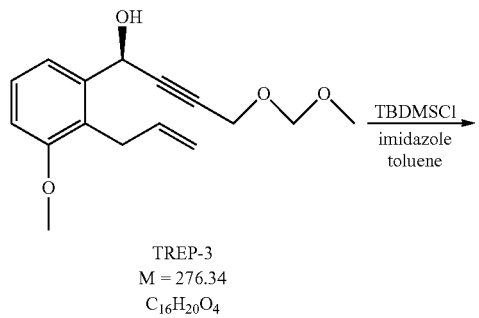

TREP-3
M = 276.34
C<sub>16</sub>H<sub>20</sub>O<sub>4</sub>

TBDMSCl
imidazole
toluene

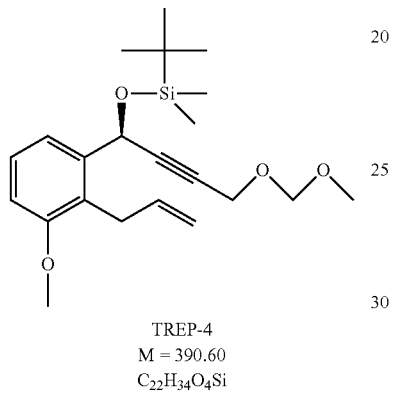

TREP-4
M = 390.60
C₂₂H₃₄O₄Si

In 850 ml of toluene are dissolved 85 g (0.31 mol) of TREP-3 and 26.6 g (0.39 mol) of imidazole. The solution is cooled to 5-10° C. and 56.8 g (0.38 mol) of tert-butyldimethylsilyl chloride (TBDMSCl) is added. The reaction mixture is stirred at room temperature for 4 hours, then 500 ml of water is added under agitation. The phases are separated, the aqueous layer is extracted with toluene, the united organic phase is evaporated in vacuum. The crude product is chromatographed on silica gel using hexane: ethyl acetate eluent.

Yield: 104.2 g (86.7%) of light brown oil.

NMR data: (CDCl3), 1H NMR (500 MHz): 7.27 ppm (H-6, 1), m (dd), J=7.9 Hz and 1.1 Hz, 7.225 ppm (H-5, 1), t, J=7.9 Hz; 6.83 ppm (H-4, 1), dd, J=7.9 Hz and 1.0 Hz; 5.95 ppm (H-14, 1), dddd, J=17.0 Hz, 10.3 Hz, 6.5 Hz and 5.3 Hz; 5.64 ppm (H-7, 1), t, J=1.5 Hz; 5.00-4.91 ppm (H-15, 2), m (4.98 ppm (H-15a, 1), dq, J=10.1 Hz and 1.6 Hz; 4.94 ppm (H-15b, 1), dq, J=17.1 Hz and 1.8 Hz); 4.67 ppm (H-11, 2), s; 4.22 ppm (H-10, 2), m; 3.82 ppm (H-16, 3); s; 3.62 ppm (H-13a, 1), ddt, J=15.7 Hz, 5.1 Hz and 1.9 Hz; 3.49 ppm (H-13b, 1), ddt, J=15.7 Hz, 6.5 Hz and 1.5 Hz; 3.34 ppm (H-12, 3), s; 0.91 ppm (H-20, H-21 and H-22, 9), s; 0.13 ppm, (H-17/H-18, 3), s; 0.085 (H-18/H-17, 3), s; 13C NMR (125.8 MHz): 157.50 ppm (C-3), 141.44 ppm (C-1), 136.55 (C-14), 127.32 (C-5), 124.78 (C-2), 118.73 ppm (C-6), 114.71 ppm (C-15), 110.10 ppm (C-4), 94.80 ppm (C-11), 87.16 (C-8), 80.71 ppm (C-9), 62.27 ppm (C-7), 55.82 ppm (C-16), 55.63 ppm (C-12), 54.60 ppm (C-10), 29.59 ppm (C-13), 25.93 ppm (C-20, C-21 and C-22), 18.40 ppm (C-19), −4.45 ppm (C-17/C-18), −4.74 ppm (C-18/C-17).

1f.) Preparation of (3aS,9R)-9-[tert-butyl(dimethyl)silyl]oxy-5-methoxy-1-(methoxymethoxymethyl)-3,3a,4,9-tetrahydrocyclopenta[b]naphthalen-2-one (TREP-5)

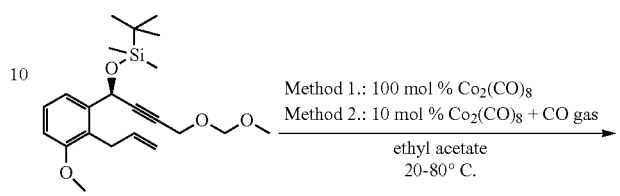

TREP-4
M = 390.60
C₂₂H₃₄O₄Si

Method 1.: 100 mol % Co₂(CO)₈
Method 2.: 10 mol % Co₂(CO)₈ + CO gas ethyl acetate
20-80° C.

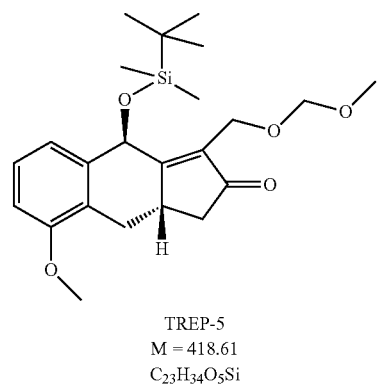

TREP-5
M = 418.61
C₂₃H₃₄O₅Si

1f1. Method (with 100 Mol % of Dicobalt Octacarbonyl)

93 g (0.24 mol) of TREP-4 is dissolved under nitrogen atmosphere in 930 ml of ethyl acetate and to the solution 85.5 g (0.25 mol) of dicobalt octacarbonyl is added. The reaction mixture is stirred at room temperature for 2.5 hours and then warmed to 60-70° C. The evolving carbon monoxide gas is lead away in closed system. At the end of the reaction the mixture is cooled to room temperature and air is bubbled through for 12 hours. The reaction mixture is filtered, the precipitate is washed with ethyl acetate. The united filtrate solution is evaporated in vacuum. The crude product is chromatographed on silica gel using hexane: ethyl acetate eluent.

Yield: 64.6 g (64.8%) of light brown oil.

1f2. Method (with 10 mol % dicobalt octacarbonyl+ carbon monoxide gas)

93 g (0.24 mol) of TREP-4 is dissolved in 930 ml of ethyl acetate under nitrogen atmosphere and 8.55 g (0.025 mol) of dicobalt octacarbonyl is added to it. The vessel is flushed with carbon monoxide, the reaction mixture is stirred at room temperature for 2.5 hours and then heated to 60-70° C. At the end of the reaction the mixture is cooled to room temperature, filtered, the precipitate is washed with ethyl acetate. The united filtrate solution is evaporated in vacuum. The crude product is chromatographed on silica gel using hexane: ethyl acetate eluent.

Yield: 85 g (85%) of light brown oil.

NMR data: (CDCl3), 1H NMR (500 MHz): 7.24 ppm (H-22, 1), m (t), J=8.0-7.4 Hz, 6.92 ppm (H-23, 1), d, J=7.3 Hz; 6.79 ppm (H-21, 1), d, J=7.8 Hz; 5.775 ppm (H-7, 1), s; 4.68-4.53 ppm (H-15, 2), m, (in: 4.62 ppm (H-15a, 1), d, J=5.6 Hz and 4.59 ppm (H-15b, 1), d, J=5.6 Hz); 4.30 ppm (H-13, 2), m; 3.815 ppm (H-2, 3), s; 3.55 ppm (H-4a, 1), dd, J=16.9 Hz and 7.3 Hz; 3.45 ppm (H-9, 1), m (ddd), J~7.8-7.0 Hz; 3.33 ppm (H-17, 3), s; 2.75 ppm (H-10a, 1), dd, J=18.7 Hz and 5.8 Hz; 2.33-2.15 ppm (H-10b and H-4b, 2), m, (in: 2.27 ppm (H-10b, 1), d, J~19.5 Hz and 2.22 ppm (H-4b, 1), dd, J=16.8 Hz and 10.2 Hz); 0.82 ppm (H-27, H-28 and H-29, 9), s; 0.15 ppm (H-24/H-25, 3), s; 0.10 ppm (H-24/H-25, 3), s; 13C NMR (125.8 MHz): 208.44 ppm (C-11), 176.76 ppm (C-8), 156.93 ppm (C-3), 138.31 ppm (C-6), 132.99 ppm (C-12), 127.61 ppm (C-22), 124.88 ppm (C-5), 122.07 ppm (C-23), 109.41 ppm (C-21), 96.42 ppm (C-15), 65.25 ppm (C-7), 59.07 ppm (C-13), 55.55 ppm (C-17), 55.47 ppm (C-2), 42.32 ppm (C-10), 33.49 ppm (C-4), 32.61 ppm (C-9), 25.75 ppm (C-27, C-28 and C-29), 18.20 ppm (C-26), −4.19 ppm (C-24/C-25), −4.32 ppm (C-25/C-24).

1g.) Preparation of (1S,9aS)-5-methoxy-1-(methoxymethoxymethyl)-1,3,3a,4,9,9a-hexahydro-cyclopenta[b]naphthalen-2-one (TREP-6)

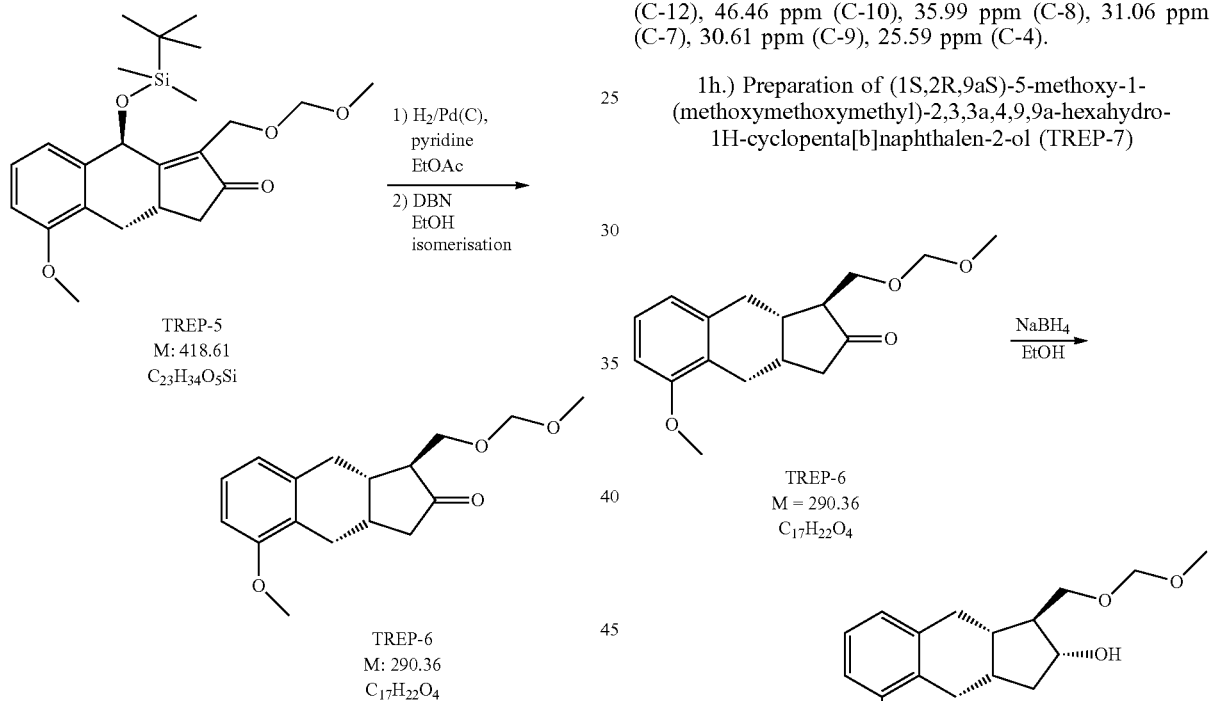

63 g (0.15 mol) of TREP-S is dissolved in 630 ml of ethyl acetate and 19 ml of pyridine is added to the solution. The reaction mixture is hydrogenated over 25 g of 10% palladium on charcoal catalyst under 6 bar pressure. At the end of the reaction the catalyst is filtered off and washed with ethyl acetate. The filtrate is evaporated in vacuum. The crude product is chromatographed on silica gel using hexane: ethyl acetate mixture as eluent. The evaporated main fraction is crystallized at 0° C. from hexane-ethyl acetate mixture and collected by filtration. The evaporated mother liquor is, in order of isomerisation, dissolved in the mixture 100 ml of toluene and 60 ml of ethanol. 12 ml of DBN reagent (2,3,4,6,7,8-hexahydropyrrolo[1,2-a]pyrimidine) is added to it at 0° C. and the mixture is agitated for 15 minutes. The reaction mixture is then quenched with NaHSO₄ solution, extracted with tert-butyl methyl ether and evaporated. The residue is chromatographed on silica gel using hexane:ethyl acetate mixture as eluent. The evaporated main fraction is crystallized at 0° C. from hexane-ethyl acetate mixture. The crystals are collected by filtration and united with earlier gained crystals.

Yield: 30.2 g (69.1%) of white crystals. Mp: 65-67° C.
NMR data: (CDCl3), 1H NMR (500 MHz): 7.13 ppm (H-22, 1), m (t), J=7.9 Hz, 6.78 ppm (H-23, 1), d, J=7.6 Hz; 6.71 ppm (H-21, 1), d, J=8.2 Hz; 4.62-4.56 ppm (H-15, 2). m, (in: 4.60 ppm (H-15a, 1), d, J=6.5 Hz and 4.58 ppm (H-15b, 1), d, J=6.5 Hz); 3.86 ppm (H-13a, 1), dd, J=9.8 Hz and 4.2 Hz; 3.81 ppm (H-2, 3), s; 3.67 ppm (H-13b, 1), m (dd), J=9.8 Hz and 3.6 Hz, 3.35 ppm (H-17, 3), s; 3.09 ppm (H-7a, 1), dd, J=16.6 Hz and 6.5 Hz; 3.03 ppm (H-4a, 1), dd, J=17.3 Hz and 7.1 Hz, 2.82 ppm (H-7b, 1), m (dd), J=16.6 Hz and 3.6 Hz, 2.715 ppm (H-8, 1), m (dtd), J=10.3 Hz, 6.8 Hz and 3.7 Hz, 2.605 ppm (H-9, 1), m (dqd), J~8.7 Hz, ~7.3 Hz and 3.1 Hz; 2.47 ppm (H-10a, 1), m (dd), J=18.1 Hz and 7.6 Hz, 2.29-2.205 ppm (H-4b and H-10b, 2), m; 2.07 ppm (H-12, 1), m (ddd), J=10.5 Hz and ~3.6 Hz; 13C NMR (125.8 MHz): 218.28 ppm (C-11), 156.96 ppm (C-3), 136.27 ppm (C-6), 126.58 ppm (C-22), 124.50 ppm (C-5), 121.34 ppm (C-23), 107.60 ppm (C-21), 96.65 ppm (C-15), 64.64 ppm (C-13), 55.40 ppm (C-2), 55.31 ppm (C-17), 51.68 ppm (C-12), 46.46 ppm (C-10), 35.99 ppm (C-8), 31.06 ppm (C-7), 30.61 ppm (C-9), 25.59 ppm (C-4).

1h.) Preparation of (1S,2R,9aS)-5-methoxy-1-(methoxymethoxymethyl)-2,3,3a,4,9,9a-hexahydro-1H-cyclopenta[b]naphthalen-2-ol (TREP-7)

22 g (75.8 mmol) TREP-6 is dissolved in 100 ml of toluene, 100 ml of ethanol is added to it and the solution is cooled to (−)15-(−25° C. To the solution 3 g (79.3 mmol) of sodium borohydride (NaBH₄) is added and the reaction mixture is stirred while keeping the above temperature. At the end of the reaction the pH is set to pH=4-6 with NaHSO₄ solution. Stirring is continued for 30 minutes, then the phases are separated. The aqueous phase is extracted with toluene. The united organic phase is washed consecutively with NaHCO₃ solution and water, then dried over sodium sulfate. The drying material is filtered off, the filtrate solution is evaporated in vacuum.

Yield: 22.15 g (100%) of colourless oil.

NMR data: (CDCl3), 1H NMR (500 MHz): 7.10 ppm (H-22, 1), t, J=7.8 Hz; 6.79-6.73 ppm (H-21 and H-22, 2), m (in: 6.765 ppm (H-23, 1), d, J=7.3 Hz and 6.76 ppm (H-21, 1), d, J=8.2 Hz); 4.64 ppm (H-15, 2), s; 3.91 ppm (H-11, 1), td, J=9.8 Hz and 6.4 Hz; 3.83-3.74 ppm (H-2 and H-13a, 4), m (in: 3.81 ppm (H-2, 3), s and 3.80 ppm (H-13a, 1), dd, J=9.2 Hz and 4.7 Hz); 3.59 ppm (H-13b, 1), t (dd), J~9.0 Hz; 3.38 ppm (H-17, 3), s; 2.79-2.69 ppm (H-4a and H-7a, 2), m (in: 2.76 ppm (H-4a, 1), dd, J=14.7 Hz and 6.2 Hz and 2.72 ppm (H-7a, 1), dd, J=14.2 Hz and 6.2 Hz); 2.61-2.53 ppm (H-4b and OH-11, 2), m (in: 2.58 ppm (OH-11, 1), broad and 2.56 ppm (H-4b, 1), dd, J=14.7 Hz and 6.2 Hz); 2.45 ppm (H-7b, 1), dd, J=14.3 Hz and 6.2 Hz; 2.31 ppm (H-9, 1), m (tdt), J=10.6 Hz, 7.4 Hz and 6.3 Hz; 2.20 ppm (H-10a, 1), ddd, J=12.0 Hz, 7.3 Hz and 6.4 Hz; 1.96 ppm (H-8, 1), tt, J=10.4 Hz and 6.1 Hz; 1.60 ppm (H-12, 1), qd/dddd, J=9.2 Hz and 4.8 Hz; 1.20 ppm (H-10b, 1), dt, J=11.9 Hz and 10.5 Hz; 13C NMR (125.8 MHz): 156.72 ppm (C-3), 140.18 ppm (C-6), 126.89 (C-5), 126.34 ppm (C-22), 120.60 ppm (C-23), 108.64 ppm (21), 96.73 ppm (C-15), 76.30 ppm (C-11), 70.75 ppm (C-13), 55.69 ppm (C-2), 55.43 ppm (C-17), 51.91 ppm (C-12), 40.45 ppm (C-10), 37.82 ppm (C-8), 33.37 ppm (C-7), 33.20 ppm (C-9), 25.62 ppm (C-4).

1i.) Preparation of [(1S,2R,9aS)-5-methoxy-1-(methoxymethoxymethyl)-2,3,3a,4,9,9a-hexahydro-1H-cyclopenta[b]naphthalen-2-yl] 4-phenylbenzoate (TREP-8)

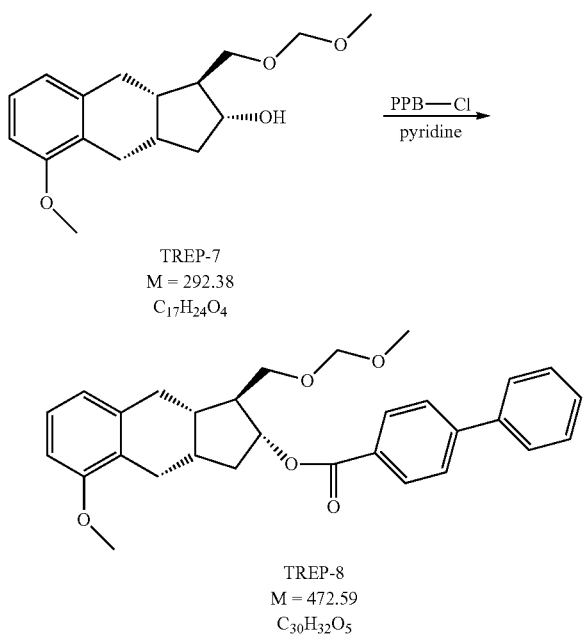

22 g (75 mmol) of TREP-7 is dissolved in 50 ml of pyridine under nitrogen atmosphere and 17.9 g (82 mmol) of p-phenylbenzoyl chloride (PPB-Cl) is added to it at a temperature of max. 50° C. The reaction mixture is stirred at 50-60° C. At the end of the reaction ethanol and water are added and the mixture is cooled to 0/5° C.-ra. After 3 hours of stirring the crystals are filtered off and washed with ethanol-water mixture.

Yield: 34.1 g (96%) of white crystals. Mp: 106-107° C.

NMR data: (CDCl3), 1H NMR (500 MHz): 8.06 ppm (H-26 and H-26', 2), m (d), J=8.5 Hz; 7.65-7.59 ppm (H-27, H-27', H-30 and H-30', 4), m, (in: 7.63 ppm (H-27 and H-27', 2), m (d), J=8.5 Hz and 7.61 ppm (H-30 and H-30', 2), m (d), J~7.5 Hz); 7.47 ppm (H-31 and H-31', 2), m (t), J~7.5 Hz; 7.39 ppm (H-32, 1), m (t/tt), J=7.4 Hz; 7.15 ppm (H-22, 1), t, J=7.8 Hz; 6.83 ppm (H-23, 1), d, J=7.5 Hz; 6.79 ppm (H-21, 1), d, J=8.1 Hz; 5.23 ppm (H-11, 1), td, J=8.7 Hz and 6.2 Hz; 4.64 ppm (H-15, 2), m (s); 3.83 ppm (H-2, 3), s; 3.72-3.63 ppm (H-13, 2), m (in: 3.69 ppm (H-13a, 1), dd, J=9.9 Hz and 4.8 Hz and 3.66 ppm (H-13b, 1), dd, J=9.9 Hz and 5.3 Hz); 3.35 ppm (H-17, 3), s; 2.87 ppm (H-4a and H-7a, 2), m (dd), J=14.7 Hz and 6.1 Hz; 2.68-2.58 ppm (H-4b and H-7b, 2), m (in: 2.65 ppm (H-7b, 1), dd, J=15.1 Hz and 6.3 Hz and 2.62 ppm (H-4b, 1), dd, J=15.5 Hz and 6.2 Hz); 2.53-2.40 ppm (H-9 and H-10a, 2), m (in: 2.475 ppm (H-10a, 1), m and 2.465 ppm (H-9, 1), m); 2.305 ppm (H-8, 1), m (tt), J~9.4 Hz and 6.3 Hz; 2.01 ppm (H-12, 1), m (tt), J=8.9 Hz and 4.9 Hz; 1.41 ppm (H-10b, 1), m; 13C NMR (125.8 MHz): 166.40 ppm (C-24), 156.74 ppm (C-3), 145.65 ppm (C-28), 140.18 ppm (C-29), 140.03 ppm (C-6), 130.20 ppm (C-26 and C-26', 2), 129.35 ppm (C-25), 129.03 ppm (C-31 and C-31', 2), 128.22 ppm (C-32), 127.39 ppm (C-30 and C-30', 2), 127.10 ppm (C-27 and C-27', 2), 126.69 (C-5), 126.38 ppm (C-22), 120.71 ppm (C-23), 108.46 ppm (21), 96.72 ppm (C-15), 76.16 ppm (C-11), 67.41 ppm (C-13), 55.65 ppm (C-2), 55.32 ppm (C-17), 50.16 ppm (C-12), 37.93 ppm (C-10), 37.55 ppm (C-8), 33.70 ppm (C-9), 33.28 ppm (C-7), 25.72 ppm (C-4).

1j.) Preparation of [(1S,2R,9aS)-1-(hydroxymethyl)-5-methoxy-2,3,3a,4,9,9a-hexahydro-1H-cyclopenta[b]naphthalen-2-yl] 4-phenylbenzoate (TREP-9)

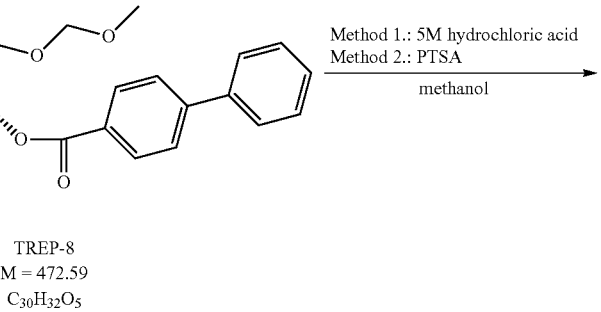

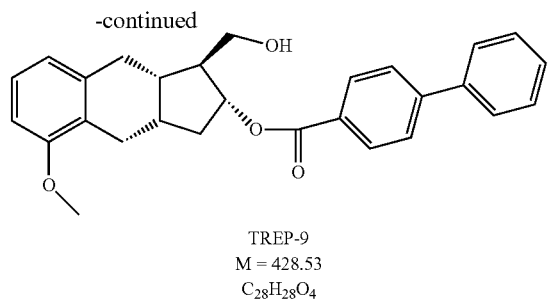

TREP-9
M = 428.53
C₂₈H₂₈O₄

28 g (59.2 mmol) of TREP-8 is dissolved in 140 ml of tetrahydrofuran and to the solution 280 ml of methanol is added.

In Method 1i1. 140 ml of 5M hydrochloric acid is added to the mixture and stirred at 45-50° C.

In Method 1 i2. 14 g of p-toluene sulfonic acid monohydrate is added to the mixture and stirred at 45-50° C.

At the end of the reaction the mixture is neutralized with NaHCO₃ solution, the organic solvents are distilled off. The residue is extracted with ethyl acetate, the united organic phase is washed with water, dried over sodium sulfate. The crude product is chromatographed on silica gel, using hexane: ethyl acetate mixture as eluent.

Yield: 23.4 g (92%) of colourless oil.

NMR data: (CDCl3), 1H NMR (500 MHz): 8.05 ppm (H-26 and H-26', 2), m (d), J=8.5 Hz; 7.65-7.58 ppm (H-27, H-27', H-30 and H-30', 4), m, (in: 7.63 ppm (H-27 and H-27', 2), m (d), J=8.5 Hz and 7.60 ppm (H-30 and H-30', 2), m (d), J~7.4 Hz); 7.46 ppm (H-31 and H-31', 2), m (t), J~7.5 Hz; 7.39 ppm (H-32, 1), m (t/tt), J=7.3 Hz; 7.14 ppm (H-22, 1), t, J=7.8 Hz; 6.82-6.76 ppm (H-21 and H-23, 2), m (in: 6.792 ppm (H-23, 1), d, J~7.3 Hz and 6.788 ppm (H-21, 1), d, J~8.4 Hz); 5.21 ppm (H-11, 1), td, J~9.3 Hz and 6.5 Hz; 3.84 ppm (H-2, 3), s; 3.71 ppm (H-13, 2), m; 2.86-2.76 ppm (H-4a and H-7a, 2), m (in: 2.82 ppm (H-7a, 1), dd, J=14.6 Hz and 6.3 Hz and 2.80 ppm (H-4a, 1), dd, J=15.0 Hz and 6.2 Hz); 2.73-2.64 ppm (H-4b and OH-13, 2), m (in: 2.70 ppm (H-4b, 1), dd, J=15.1 Hz and 5.8 Hz and 2.67 ppm (OH-13, 1), broad); 2.56 ppm (H-7b, 1), dd, J=14.6 Hz and 5.6 Hz; 2.45 ppm (H-9, 1), m; 2.40-2.31 ppm (H-8 and H-10a, 2), m (in: 2.365 ppm (H-10a, 1), m, J~11.9 and 7.0 and 2.35 ppm (H-8, 1), m, J=10.4 Hz and 7.1 Hz); 1.71 ppm (H-12, 1), m tt, J=9.2 Hz and 4.1 Hz; 1.53 ppm (H-10b, 1), dt, J=12.1 Hz and 9.5 Hz; 13C NMR (125.8 MHz): 167.40 ppm (C-24), 156.86 ppm (C-3), 146.01 ppm (C-28), 140.08 ppm (C-29), 139.79 ppm (C-6), 130.34 ppm (C-26 and C-26', 2), 129.06 ppm (C-31 and C-31', 2), 128.83 ppm (C-25), 128.32 ppm (C-32), 127.41 ppm (C-30 and C-30', 2), 127.16 ppm (C-27 and C-27', 2), 126.51 (C-5), 126.42 ppm (C-22), 120.88 ppm (C-23), 108.52 ppm (C-21), 75.40 ppm (C-11), 61.16 ppm (C-13). 55.69 ppm (C-2). 52.83 ppm (C-12), 37.56 ppm (C-10), 36.32 ppm (C-8), 33.01 ppm (C-9), 32.71 ppm (C-7), 25.48 ppm (C-4).

1k.) Preparation of [(1R,2R,3aS,9aS)-5-methoxy-1-[(E)-3-oxooct-1-enyl]-2,3,3a,4,9,9a-hexahydro-1H-cyclopenta[b]naphthalen-2-yl] 4-phenylbenzoate (TREP-11)

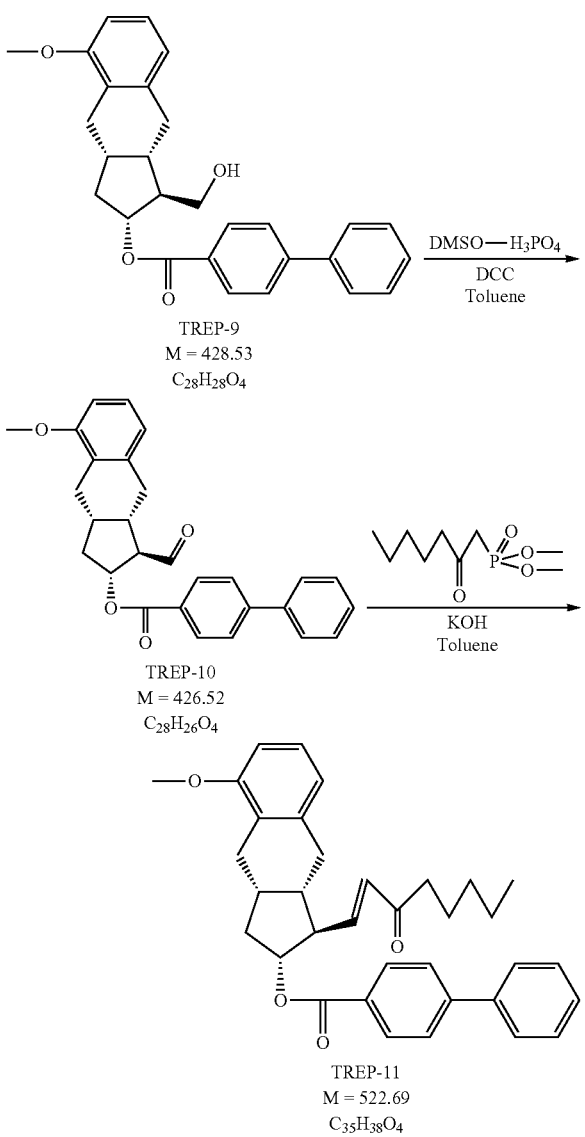

TREP-9
M = 428.53
C₂₈H₂₈O₄

TREP-10
M = 426.52
C₂₈H₂₆O₄

TREP-11
M = 522.69
C₃₅H₃₈O₄

20 g (46.7 mmol) of TREP-9 is dissolved in an inert atmosphere in 200 ml water-free toluene. 30 g of dicyclohexylcarbodiimide (DCC) and 10 ml of dimethyl sulfoxide in phosphoric acid are added. The reaction mixture is heated to 50° C. and in portions, a further 5 ml of dimethyl sulfoxide in phosphoric acid are added. When the oxidation is completed, the reaction mixture is cooled to −10° C. and at that temperature 4 g (71 mmol) of potassium hydroxide and then 10.9 g (49 mmol) of 2-oxo-heptylphosphoric acid dimethyl ester in toluene solution are added. At the end of the reaction, under agitation, the mixture is poured onto acid solution. The precipitated crystals are filtered off and washed. The phases of the filtrate are separated, the organic phase is washed with 1M sodium hydrogen carbonate solution and then with diluted hydrochloric acid solution. The organic phase is evaporated and purified by chromatography on silica gel column using toluene:hexane eluent.

Yield: 23 g (94.3%) of light brown oil.

Alternative method of 1k/2

20 g(46.7 mmol) of TREP-9 is dissolved in 200 ml toluene and 0.9 g potassium bromide and 0.2 g TEMPO/(2,2,6,6-Tetramethyl-piperidin-1-yl)oxyl/catalyst are added to the solution. The reaction mixture is cooled to the range of 0 C-(+10 C) and 150 ml sodium hypochlorite solution are added(active chlorine content is 6-14%) and the mixture is stirred at this temperature. When the oxidation is completed the phases of the reaction mixture are separated, organic phase is washed with aqueous solution of Na2S2O3, with aqueous solution of KBr and finally with water.

10.9 g (49 mmol) 2-oxo-heptylphosphoric acid dimethyl ester and 100 ml 3M potassium hydroxide solution are added to the organic phase. The reaction mixture is agitated at room temperature. After completion of the reaction the phases are separated and the organic phase is washed with 1M sodium hydrogen sulfate solution and 15% NaCl solution.

The organic phase is evaporated and purified by chromatography on silica gel column using toluene:hexane eluent.

Yield: 23 g (94,35%) of light brown oil.

NMR data: (CDCl3), 1H NMR (500 MHz): 8.00 ppm (H-26 and H-26', 2), m (d), J=8.3 Hz; 7.64-7.56 ppm (H-27, H-27', H-30 and H-30', 4), m, (in: 7.61 ppm (H-27 and H-27', 2), m (d), J=8.4 Hz and 7.59 ppm (H-30 and H-30', 2), m (d), J~7.7 Hz); 7.45 ppm (H-31 and H-31', 2), m (t), J~7.5 Hz; 7.38 ppm (H-32, 1), m (t/tt), J=7.3 Hz; 7.165 ppm (H-22, 1), t, J=7.9 Hz; 6.83-6.76 ppm (H-13, H-21 and H-23, 3), m (in: 6.80 ppm (H-21 and H-23, 2), d, J=7.9 Hz and 6.80 ppm (H-13, 1), dd, J=15.8 Hz and 8.3 Hz); 6.12 ppm (H-14, 1), d, J=15.8 Hz; 5.18 ppm (H-11, 1), td, J=9.6 Hz and 6.2 Hz; 3.83 ppm (H-2, 3), m (s); 2.79-2.70 ppm (H-4 and H-7a, 3), m (in: 2.75 ppm (H-7a, 1), dd, J=14.7 Hz and 5.9 Hz and 2.73 ppm (H-4, 2), d, J=5.5 Hz); 2.62-2.48 ppm (H-7b, H-9, H-10a and H-16, 5), m (in: 2.565 ppm (H-9, 1), m; 2.55 ppm (H-16, 1), t, J=7.4 Hz; 2.53 ppm (H-10a, 1), m; 2.515 ppm (H-7b, 1), m); 2.40-2.27 ppm (H-8 and H-12, 2), m (in: 2.36 ppm (H-12, 1), m and 2.31 ppm (H-8, 1), m); 1.67-1.53 ppm (H-17, 2), m (tt), J=7.4 Hz, 1.38-1.22 ppm (H-10b, H-18 and H-19, 5), m (in: 1.34 ppm (H-10b, 1), m (dt), J~11.8 Hz and 9.6 Hz; 1.29 ppm (H-19, 2) m and 1.28 ppm (H-18, 2) m); 0.87 ppm (H-20, 3), m (t), J=6.9 Hz; 13C NMR (125.8 MHz): 200.85 ppm (C-15), 166.23 ppm (C-24), 156.99 ppm (C-3), 146.53 ppm (C-13), 145.89 ppm (C-28), 140.14 ppm (C-29), 139.28 ppm (C-6), 131.85 ppm (C-14), 130.22 ppm (C-26 and C-26', 2), 129.05 ppm (C-31 and C-31', 2), 128.93 ppm (C-25), 128.28 ppm (C-32), 127.41 ppm (C-30 and C-31', 2), 127.14 ppm (C-27 and C-27', 2), 126.70 (C-22), 126.23 ppm (C-5), 120.93 ppm (C-23), 108.76 ppm (C-21), 77.31 ppm (C-11), 55.69 ppm (C-2), 53.49 ppm (C-12), 40.24 ppm (C-8), 40.16 ppm (C-16), 37.89 ppm (C-10), 33.16 ppm (C-9), 31.88 ppm (C-7), 31.58 ppm (C-18), 25.32 ppm (C-4), 24.08 ppm (C-17), 22.60 ppm (C-19), 14.05 ppm (C-20).

Preparation of 2-Oxo-heptylphosphonic Acid Dimethyl Ester

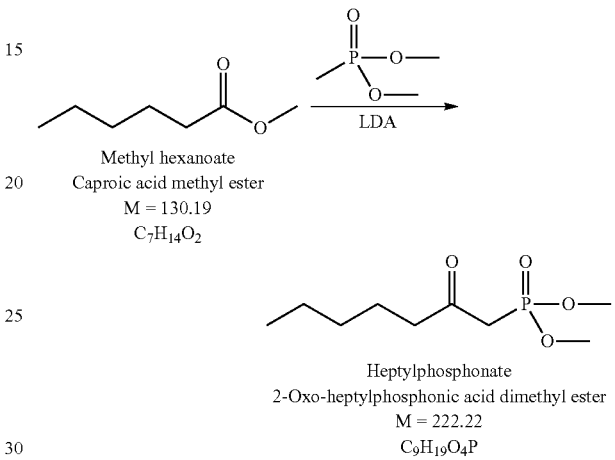

Methyl hexanoate
Caproic acid methyl ester
M = 130.19
$C_7H_{14}O_2$

Heptylphosphonate
2-Oxo-heptylphosphonic acid dimethyl ester
M = 222.22
$C_9H_{19}O_4P$ Preparation of Lithium Diisopropylamide (LDA)

In nitrogen atmosphere, under stirring 3.017 g of diisopropylamine is dissolved in 13.6 ml of tetrahydrofuran (THF) and to it is added at 0±5° C. the hexane solution of 17.9 ml butyl lithium (BuLi) (1.6M solution in hexane). The mixture is stirred for 1 hour at room temperature.

Phosphonate Formation

Under nitrogen atmosphere 1.85 g of dimethyl methylphosphonate and 1.77 ml of methyl hexanoate are dissolved in 10.2 ml of tetrahydrofuran (THF), under stirring. The solution is cooled to 0/−5° C. and at that temperature in a period of approx. 30 minutes the lithium diisopropylamide (LDA) solution is added dropwise. The reaction mixture is stirred at 0/−5° C. for 1 hour and then 37 ml of 2M NaHCO3 solution is added. Stirring is continued at room temperature for 1 hour, the phases are separated, the aqueous phase is extracted with tert-butyl methyl ether (TBME). The united organic phase is washed with saturated sodium chloride solution, evaporated in vacuum and dried by distilling toluene over it in rotadest on a water bath of 45+5° C.

Yield: 2.718 g (90%) of yellow oil.

NMR data: (DMSO), 1H NMR (500 MHz): 3.65 ppm (H-9 and H-10, 6), d, J=11.2 Hz; 3.26 ppm (H-1, 2), m (d), J=22.1 Hz, 2.555 ppm (H-3, 2), t, J=7.2 Hz; 1.45 ppm (H-4, 2), qui (tt), J=7.3 Hz; 1.32-1.15 ppm (H-5 and H-6, 4), m, (in: 1.26 ppm (H-6, 2), m and 1.20 ppm (H-5, 2), m); 0.85 ppm (H-7, 3), t, J=7.2 Hz; 13C NMR (125.8 MHz): 202.23 ppm (C-2), d, J=5.9 Hz; 52.47 ppm (C-9 and C-10, 2), d, J=6.3 Hz; 43.04 ppm (C-3), d, J=1.4 Hz; 40.21 ppm (C-11), d, J=125.5 Hz, 30.50 ppm (C-5); 22.40 ppm (C-4); 21.82 ppm (C-6); 13.72 ppm (C-7); 31P NMR (202.46 MHz): 23.52 ppm (P-8), m.

11.) Preparation of [(1R,2R,3aS,9aS)-1-[(E,3S)-3-hydroxyoct-1-enyl]-5-methoxy-2,3,3a,4,9,9a-hexahydro-1H-cyclopenta[b]naphth-2-yl] 4-phenylbenzoate (TREP-12)

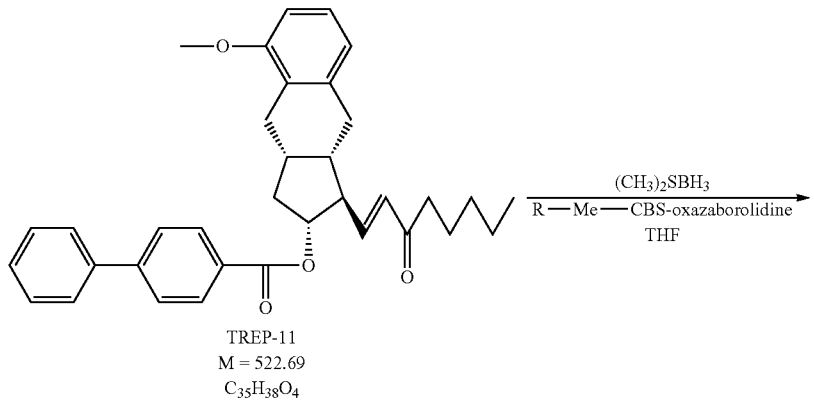

TREP-11
M = 522.69
C₃₅H₃₈O₄

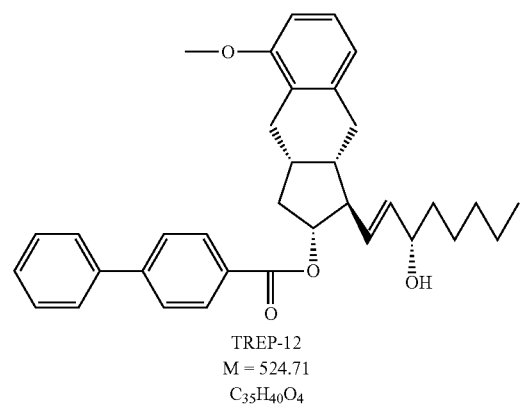

TREP-12
M = 524.71
C₃₅H₄₀O₄

19 g (36.3 mmol) of TREP-11 is dissolved under nitrogen atmosphere in 190 ml water-free tetrahydrofuran. The solution is cooled to 0-5° C. and 36.3 ml (36.3 mmol) of oxazaborolidine solution (I M toluene solution) is added. The mixture is cooled to (−30°) C and while keeping that temperature, 9.5 ml (99 mmol) of borane-dimethyl sulfide complex is added to it dropwise. The reaction mixture is stirred at that temperature. At the end of the reaction the mixture is allowed to warm to (−15°) C and carefully methanol is added to it (strong foaming and heat formation). The mixture is stirred for 30 minutes and then NaHSO₄ solution is added to it at 0-5° C. The precipitated crystals are filtered off and washed with toluene. The liquid filtrate is extracted with 3×50 ml of toluene. The united organic phase is washed with water and dried over sodium sulfate. The drying material is filtered off and the filtrate is evaporated.

Yield: 18.2 g (95.4%) of light brown oil.

NMR data: (CDCl3), 1H NMR (500 MHz): 8.02 ppm (H-26 and H-26', 2), m (d), J=8.4 Hz; 7.63-7.56 ppm (H-27, H-27', H-30 and H-30', 4), m, (in: 7.60 ppm (H-27 and H-27', 2), m (d), J=8.3 Hz and 7.59 ppm (H-30 and H-30', 2), m (d), J~7.1 Hz); 7.45 ppm (H-31 and H-31', 2), m (t), J~7.4 Hz; 7.38 ppm (H-32, 1), m (t/tt), J=7.3 Hz; 7.15 ppm (H-22, 1), m (t), J=7.8 Hz; 6.83-6.76 ppm (H-21 and H-23, 2), m (in: 6.79 ppm (H-21 and H-23, 2), m); 5.635 ppm (H-13, 1), dd, J=15.4 Hz and 7.6 Hz; 5.54 ppm (H-14, 1), m (dd), J=15.4 Hz and 6.4 Hz, 5.09 ppm (H-11, 1), td, J=9.5 Hz and 6.1 Hz, 4.085 ppm (H-15, 1), m (q), J=6.4 Hz, 3.82 ppm (H-2, 3), m (s), 2.79-2.70 ppm (H-4a and H-7a, 2), m (in: 2.74 ppm (H-4a and H-7a, 2), m (dd), J~13.8 Hz and ~5.5 Hz); 2.665 ppm (H-4b, 1), m (dd), J=14.9 Hz and 5.2 Hz, 2.57-2.41 ppm (H-7b, H-9 and H-10a, 3), m (in: 2.51 ppm (H-7, 1), m (dd), J=14.6 Hz and 4.6 Hz; 2.48 ppm (H-9, 1), m; 2.47 ppm (H-10a, 1), m); 2.25-2.11 ppm (H-8 and H-12, 2), m, (in: 2.20 ppm (H-12, 1), m and 2.18 ppm (H-8, 1), m); 1.68 ppm (OH-15, 1), broad; 1.60-1.39 ppm (H-16, 2). m. (in: 1.51 ppm (H-16a, 1), m and 1.45 ppm (H-16b, 1), m); 1.38-1.18 ppm (H-10b, H-17, H-18 and H-19, 7), m, (in: 1.31 ppm (H-10b and H-17a, 2), m; 1.25 ppm (H-17b, H-18 and H-19, 5) m); 0.85 ppm (H-20, 3), m (t), J=6.8 Hz 13C NMR (125.8 MHz): 166.50 ppm (C-24), 156.90 ppm (C-3), 145.71 ppm (C-28), 140.18 ppm (C-29), 139.89 ppm (C-6), 135.69 ppm (C-13), 131.52 ppm (C-14), 130.18 ppm (C-26 and C-26', 2), 129.26 ppm (C-25), 129.03 ppm (C-31 and C-31', 2), 128.22 ppm (C-32), 127.38 ppm (C-30 and C-30', 2), 127.10 ppm (C-27 and C-27', 2), 126.55 ppm (C-5), 126.49 (C-22), 120.87 ppm (C-23), 108.58 ppm (C-21), 77.84 ppm (C-11), 72.76 ppm (C-15), 55.68 ppm (C-2), 53.53 ppm (C-12), 40.14 ppm (C-8), 37.66 ppm (C-10), 37.26 ppm (C-16), 33.00 ppm (C-9), 32.02 ppm (C-7), 31.86 ppm (C-18), 25.53 ppm (C-4), 25.12 ppm (C-17), 22.71 ppm (C-19), 14.14 ppm (C-20).

1m.) Preparation of (1R,3aS,9aS)-1-[(E)-3-hydroxyoct-1-enyl]-5-methoxy-2,3,3a,4,9,9a-hexahydro-1H-cyclopenta[b]naphthalen-2-ol (TREP-13)

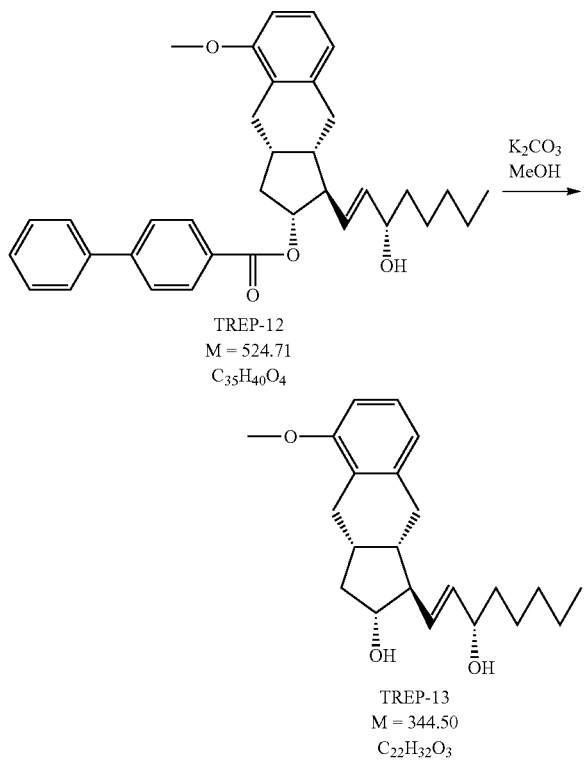

17 g (32.4 mmol) of TREP-12 is dissolved in 70 ml of methanol, 4.2 g (30.3 mmol) of $K_2CO_3$ is added and the mixture is stirred at 40° C. till the end of the reaction. When the desired conversion is reached, the reaction mixture is cooled to 0° C. and in portions phosporic acid solution is added to it. The precipitated p-phenylbenzoyl methyl ester (PPB-methyl ester) is filtered off and washed. The filtrate is concentrated, water and toluene are added to it and the phases are separated. The aqueous phase is extracted with toluene, the organic phase is dried over $Na_2SO_4$, the drying material is filtered off, the filtrate is evaporated and purified by chromatography on silica gel column (using hexane:tert-butyl methyl ether mixture eluent). The main fraction is crystallized from the mixture of hexane and tert-butyl methyl ether. The precipitated crystals are filtered off, washed and dried.

Yield: 8 g (72%) of white crystals. Mp: 75-77° C.

NMR data: (CDCl3), 1H NMR (500 MHz): 7.10 ppm (H-22, 1), t, J=7.8 Hz; 6.78-6.70 ppm (H-21 and H-23, 2), m (in: 6.75 ppm (H-21, 1), m (d), J=8.3 Hz and 6.73 ppm (H-23, 1), m (d), J=7.4 Hz); 5.52-5.42 ppm (H-13 and H-14, 2), m (in: 5.47 ppm (H-13 and H-14, 2), m); 4.04 ppm (H-15, 1), m, J=6.5 Hz and 3.2 Hz; 3.80 ppm (H-2, 3), s; 3.70 ppm (H-11, 1), td, J=10.1 Hz and 6.1 Hz; 2.70-2.46 ppm (H-4a, H-7a, H-7b, OH-11 and OH-15, 5), m (in: 2.66 ppm (H-4a, 1), m (dd), J=14.9 Hz and 6.2 Hz; 2.63 ppm (H-7a, 1), m (dd), J~14.9 Hz and –0.6.1 Hz; 2.59 ppm (H-4b, 1), m (dd), J=14.7 Hz and 5.6 Hz; 2.57 ppm (OH-11 and OH-15, 2), m (broad)); 2.40-2.27 ppm (H-7b and H-9, 2), m (in: 2.37 ppm (H-7b, 1), m (dd), J=14.3 Hz and 5.4 Hz; 2.32 ppm (H-9, 1), m); 2.23-2.13 ppm (H-10a, 1), m, (in: 2.19 ppm (H-10a, 1), m (ddd), J=12.1 Hz, 7.4 Hz and 6.4 Hz); 2.02 ppm (H-8, 1), m (tt), J=10.9 Hz and 5.5 Hz; 1.71 ppm (H-12, 1), m; 1.57 ppm (H-16a, 1), m; 1.48 ppm (H-16b, 1), m; 1.43-1.23 ppm (H-17, H-18 and H-19, 6), m, (in: 1.37 ppm (H-17a, 1), m; 1.33 ppm (H-19, 2), m; 1.325 ppm (H-17b, 1), m; 1.32 ppm (H-18, 2), m); 1.08 ppm (H-10b, 1) m(dt/q), J=11.7 Hz and 10.5 Hz; 0.91 ppm (H-20, 3), m (t), J=6.9 Hz; 13C NMR (125.8 MHz): 156.81 ppm (C-3), 140.33 ppm (C-6), 136.20 ppm (C-14), 133.38 ppm (C-13), 126.87 ppm (C-5), 126.38 (C-22), 120.77 ppm (C-23), 108.58 ppm (C-21), 75.87 ppm (C-11), 73.32 ppm (C-15), 56.94 ppm (C-12), 55.71 ppm (C-2), 40.61 ppm (C-8), 40.49 ppm (C-10), 37.29 ppm (C-16), 32.73 ppm (C-9), 32.21 ppm (C-7), 31.85 ppm (C-18), 25.54 ppm (C-4), 25.37 ppm (C-17), 22.78 ppm (C-19), 14.18 ppm (C-20).

1n.) Preparation of (1R,3aS,9aS)-1-(3-hydroxyoctyl)-5-methoxy-2,3,3a,4,9,9a-hexahydro-1H-cyclopenta[b]naphthalen-2-ol (TREP-14)

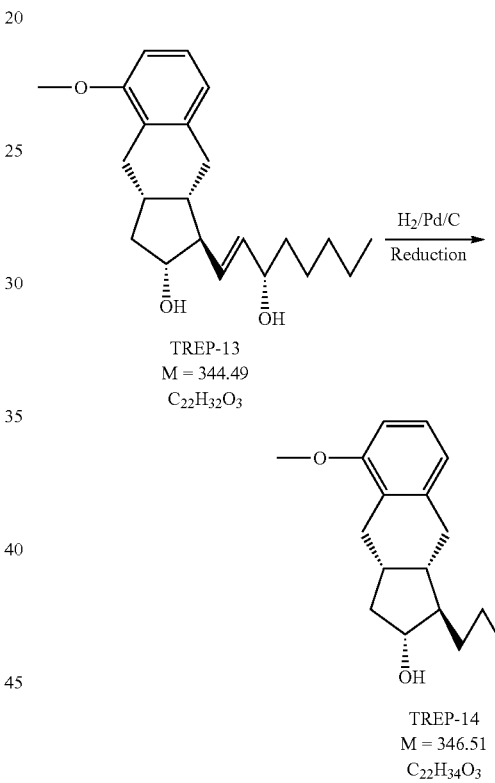

In the mixture of 77 ml of methyl ethyl ketone and 154 ml of ethanol 7.7 g (22.3 mmol) of TREP-13 is dissolved. The reaction mixture is hydrogenated under 6 bar pressure over 0.77 g of 10% palladium on charcoal catalyst desactivated with sodium nitrite. At the end of the reaction the catalyst is filtered off, washed with ethyl acetate, the filtrate is evaporated in vacuum and the residue is crystallized from hexane:ethyl acetate mixture.

Yield: 6.4 g (83%) of white crystals. Mp: 71-72° C.

NMR data: (CDCl3), 1H NMR (500 MHz): 7.09 ppm (H-22, 1), t, J=7.8 Hz; 6.78-6.71 ppm (H-21 and H-23, 2), m (in: 6.75 ppm (H-23, 1), m (d), J~7.4 Hz and 6.74 ppm (H-21, 1), m (d), J=8.1 Hz); 3.80 ppm (H-2, 3), s; 3.71 ppm (H-11, 1), td, J~9.6 Hz and 6.1 Hz; 3.59 ppm (H-15, 1), m; 2.83-2.69 ppm (H-4a and H-7a, 2), m (in: 2.79 ppm (H-4a, 1), m (dd), J=14.7 Hz and 6.1 Hz; 2.74 ppm (H-7a, 1), m (dd), J=14.3 Hz and 6.2 Hz); 2.51-2.40 ppm (H-4b és H-7b, 2), m (in: 2.47 ppm (H-4b, 1), m (dd), J=14.8 Hz and 6.5 Hz; 2.44 ppm (H-7b, 1), m (dd)), J=14.4 Hz and 6.6 Hz); 2.40-2.19 ppm (H-9 and OH-11/OH-15, 2), m (in: 2.31 ppm (OH-11/OH-15, 1), broad and 2.22 ppm (H-9, 1), m, J=10.2 Hz and ~7.0 Hz); 2.19-1.97 ppm (H-10a and OH-11/OH-15, 2), m, (in: 2.155 ppm (H-10a, 1), m (ddd), J=11.7 Hz, 7.4 Hz and 6.1 Hz and 2.08 ppm (OH-11/OH-15, 1), broad); 1.92-1.74 ppm (H-8 and H-11/H-15/water, 2), m, (in: 1.87 ppm (H-8, 1), m (tt), J=10.0 Hz and 6.4 Hz and 1.81 ppm (OH-11/OH-15, 1), broad); 1.69-1.50 ppm (H-13 and H-14, 4), m (in: 1.62 ppm (H-13a and H-14a, 2) m; 1.57 ppm (H-13b, 1), m and 1.55 ppm (H-14b, 1), m); 1.50-1.38 ppm (H-16 and H-17a, 3), m (in: 1.47 ppm (H-16a, 1), m and 1.435 ppm (H-16b, 1), m and 1.43 ppm (H-17a, 1), m); 1.38-1.22 ppm (H-12, H-17b, H-18 and H-19, 6), m (in: 1.32 ppm (H-19, 2), m; 1.31 ppm (H-17b, 1), m; 1.30 ppm (H-12 and H-18, 3), m); 1.14 ppm (H-10b, 1), m (dt), J=11.5 Hz and 10.1 Hz; 0.90 ppm (H-20, 3), m (t), J=6.9 Hz; 13C NMR (125.8 MHz): 156.64 ppm (C-3), 140.65 ppm (C-6), 127.09 ppm (C-5), 126.26 (C-22), 120.60 ppm (C-23), 108.51 ppm (C-21), 77.51 ppm (C-11), 72.70 ppm (C-15), 55.72 ppm (C-2), 52.40 ppm (C-12), 41.54 ppm (C-10), 41.44 ppm (C-8), 37.58 ppm (C-16), 35.14 ppm (C-14), 33.82 ppm (C-7), 32.96 ppm (C-9), 32.05 ppm (C-18), 28.77 ppm (C-13), 25.88 ppm (C-4), 25.52 ppm (C-17), 22.78 ppm (C-19), 14.18 ppm (C-20).

1o.) Preparation of (1R,2R,3aS,9aS)-1-[(3S)-3-hydroxyoctyl]-2,3,3a,4,9,9a-hexahydro-1H-benz[f]indene-2,5-diol (TREP-15)

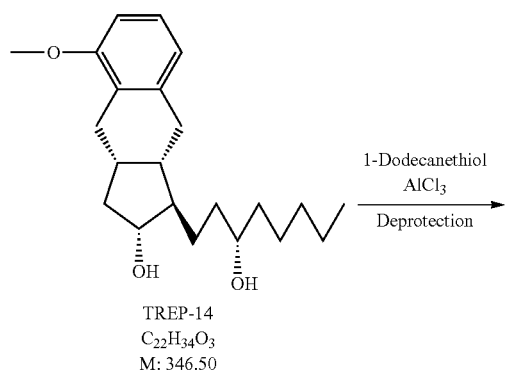

TREP-14
$C_{22}H_{34}O_3$
M: 346.50

1-Dodecanethiol
$AlCl_3$
Deprotection

TREP-15
$C_{21}H_{32}O_3$
M: 332.48

To 2.4 l of l-dodecanethiol under nitrogen atmosphere 400 g of water-free aluminum chloride is added. The mixture is cooled to 0-5° C. and the solution of 200 g of TREP-14 in 560 ml of dichloromethane is added to it. The reaction mixture is stirred at room temperature. At the end of the reaction the mixture is poured onto 4 l of water and then 664 ml of 2M sodium hydrogen sulfate is added. The phases are separated, the aqueous phase is extracted with ethyl acetate. The organic phase is washed with saturated sodium chloride solution, dried over sodium sulfate and evaporated. The residue is crystallized from hexane. The crystals are filtered off, washed and recrystallized from hexane: ethyl acetate mixture.

Yield: 182 g (95%) of white crystals. Mp: 113-115° C.

NMR data: (CDCl3), 1H NMR (500 MHz): 6.99 ppm (H-22, 1), t, J=7.7 Hz; 6.73 ppm (H-23, 1), d, J=7.4 Hz; 6.65 ppm (H-21, 1), d, J=8.0 Hz; 4.95 ppm (OH-3, 1), s; 3.75 ppm (H-11, 1), td, J=9.4 Hz and 6.2 Hz; 3.62 ppm (H-15, 1), m; 2.78-2.675 ppm (H-4a and H-7a, 2), m (in: 2.735 ppm (H-7a, 1), m (dd), J=14.0 Hz and 7.0 Hz; 2.72 ppm (H-4a, 1), m (dd), J=14.6 Hz and 6.5 Hz); 2.51-2.42 ppm (H-4b and H-7b, 2), m (in: 2.47 ppm (H-4b, 1), m (dd), J=14.6 Hz and 6.3 Hz; 2.46 ppm (H-7b, 1), m (dd)), J=14.2 Hz and 6.2 Hz); 2.28 ppm (H-9, 1), m, J=10.3 Hz, ~7.3 Hz and ~6.5 Hz; 2.175 ppm (H-10a, 1), m (ddd/dt), J=12.0 Hz, 7.3 Hz and 6.4 Hz; 1.95-1.85 ppm (H-8, 1), m (in: 1.90 ppm (H-8, 1), m (tt), J=10.0 Hz and 6.2 Hz); 1.72-1.61 ppm (H-13a and H-14a, 2), m (in: 1.655 ppm (H-14a, 1), m and 1.65 ppm (H-14a, 1), m); 1.61-1.51 ppm (H-13b and H-14b, 2), m (in: 1.56 ppm (H-14b, 1), m and 1.55 ppm (H-13b, 1), m); 1.51-1.385 ppm (H-16 and H-17a, 3), m (in: 1.48 ppm (H-16a, 1), m and 1.44 ppm (H-16b and H-17a, 2), m); 1.385-1.22 ppm (H-12, H-17b, H-18 and H-19, 6), m (in: 1.32 ppm (H-19, 2), m; 1.31 ppm (H-17b, 1), m; 1.305 ppm (H-18, 2), m; 1.285 ppm (H-12, 1), m); 1.16 ppm (H-10b, 1), dt, J=11.8 Hz and 10.2 Hz; 0.90 ppm (H-20, 3), m (t), J=6.9 Hz;

13C NMR (125.8 MHz): 152.65 ppm (C-3), 141.00 ppm (C-6), 126.39 (C-22), 124.60 ppm (C-5), 120.67 ppm (C-23), 113.15 ppm (C-21), 77.56 ppm (C-11), 72.79 ppm (C-15), 52.30 ppm (C-12), 41.50 ppm (C-10), 41.41 ppm (C-8), 37.58 ppm (C-16), 35.09 ppm (C-14), 33.74 ppm (C-7), 33.00 ppm (C-9), 32.05 ppm (C-18), 28.78 ppm (C-13), 26.12 ppm (C-4), 25.52 ppm (C-17), 22.79 ppm (C-19), 14.20 ppm (C-20).

1p.) Preparation of 2-[[(1R,2R,3aS,9aS)-2,3,3a,4,9,9a-hexahydro-2-hydroxy-1-[(3S)-3-hydroxyoctyl]-1H-benz[f]inden-5-yl]oxy]acetic acid ethyl ester (TREP-16)

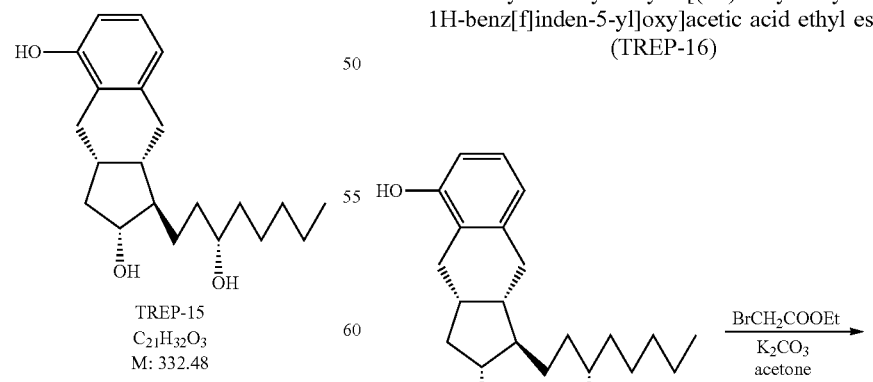

TREP-15
$C_{21}H_{32}O_3$
M: 332.48

$BrCH_2COOEt$
$K_2CO_3$
acetone

-continued

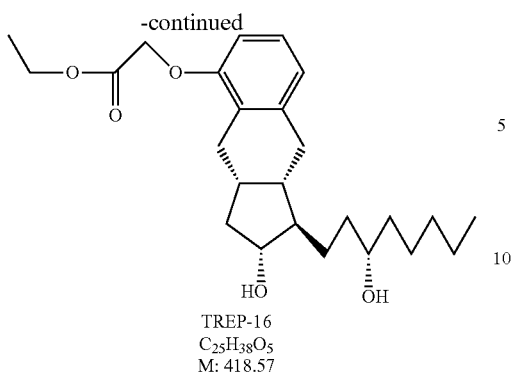

TREP-16
C$_{25}$H$_{38}$O$_5$
M: 418.57

170 g (0.51 mol) of TREP-15 is dissolved in 3.4 l of acetone. To the solution 340 g (2.46 mol) of anhydrous potassium carbonate and 89.6 g (0.536 mol) of bromoacetic acid ethyl ester are added and the mixture is stirred at 30-35° C. At the end of the reaction the reaction mixture is filtered, the filtrate is evaporated. From the residue the product is crystallized with TBME (tert-butyl methyl ether):hexane mixture, filtered off, washed and dried.

Yield: 203 g (95%) of white crystals. Mp: 53-55° C.

NMR data:

(CDCl3, 1H NMR (500 MHz): 7.03 ppm (H-22, 1), t. J=7.8 Hz; 6.78 ppm (H-23, 1), d, J=7.4 Hz; 6.605 ppm (H-21, 1), d, J=8.2 Hz; 4.58 ppm (H-2, 2), s; 4.23 ppm (H-24, 2), q, J=7.1 Hz; 3.66 ppm (H-11, 1), td, J=9.6 Hz and 6.2 Hz; 3.55 ppm (H-15, 1), m; 2.87 ppm (H-4a, 1), dd, J=14.7 Hz and 6.1 Hz; 2.80-2.455 ppm (H-4b, H-7a, OH-11 and OH-15, 4), m (in: 2.72 ppm (H-7a, 1), dd, J=14.2 Hz and 6.2 Hz; 2.67 ppm (OH-11 and OH-15, 2), 2.50 ppm (H-4b, 1), dd, J=14.7 Hz and 6.7 Hz); 2.42 ppm (H-7b, 1), dd, J=14.2 Hz and 6.8 Hz; 2.25-2.07 ppm (H-9 and H-10a, 2), m, (in: 2.20 ppm (H-9, 1), m, J=10.2 Hz, ~6.5-7.1 Hz; 2.125 ppm (H-10a, 1), m (ddd/dt), J~12.0 Hz, ~7.2 Hz and ~6.2 Hz), 1.83 ppm (H-8, 1), m (tt), J=9.9 Hz and 6.6 Hz; 1.70-1.57 ppm (H-13a and H-14a, 2), m (in: 1.635 ppm (H-14a, 1), m and 1.625 ppm (H-14a, 1), m); 1.57-1.36 ppm (H-13b, H-14b, H-16 and H-17a, 5), m (in: 1.50 ppm (H-14b. 1), m; 1.48 ppm (H-13b, 1), m; 1.435 ppm (H-16a, 1), m; 1.415 ppm (H-17a, 1), m, 1.40 ppm (H-16b, 1), m); 1.36-1.19 ppm (H-12, H-17b, H-18, H-19 and H-25, 9), m (in: 1.295 ppm (H-19, 2), m; 1.28 ppm (H-17b, 1), m; 1.275 ppm (H-18, 2), m; 1.27 ppm (H-25, 3), t, J=7.1 Hz; 1.24 ppm (H-12, 1), m); 1.14 ppm (H-10b, 1), dt, J=11.6 Hz and 10.2 Hz; 0.88 ppm (H-20, 3), t, J=6.9 Hz; 13C NMR (125.8 MHz): 169.32 ppm (C-1), 154.94 ppm (C-3), 141.15 ppm (C-6), 127.92 (C-5), 126.11 ppm (C-22), 121.55 ppm (C-23), 109.76 ppm (C-21), 77.16 ppm (C-11), 72.47 ppm (C-15), 66.12 ppm (C-2), 61.26 ppm (C-24), 52.31 ppm (C-12), 41.27 ppm (C-8), 41.25 ppm (C-10), 37.49 ppm (C-16), 35.06 ppm (C-14), 33.88 ppm (C-7), 32.80 ppm (C-9), 31.99 ppm (C-18), 28.63 ppm (C-13), 26.08 ppm (C-4), 25.47 ppm (C-17), 22.71 ppm (C-19), 14.22 (C-25), 14.13 ppm (C-20).

1q.) Preparation of 2-[[(1R,2R,3aS,9aS)-2,3,3a,4,9, 9a-hexahydro-2-hydroxy-1-[(3S)-3-hydroxyoctyl]-1H-benz[f]inden-5-yl]oxy]acetic Acid (Treprostinil)

180 g (0.43 mol) of TREP-16 (ethyl ester) is dissolved in 650 ml of tetrahydrofuran. Under nitrogen atmosphere, at room temperature 2.7 l of 0.5 M sodium hydroxide solution is added and the reaction mixture is stirred at room temperature. At the end of the reaction the mixture is washed with distilled tert-butyl methyl ether. To the aqueous alkaline phase tert-butyl methyl ether is added and the pH of the mixture is set to pH≤3 with 1M sodium hydrogen sulfate solution. The aqueous acidic phase is then extracted with tert-butyl methyl ether, the united organic phase is washed with water and evaporated.

Yield: 165 g (98%) of crystallizing oil.

NMR data (d6-DMSO), 1H NMR (400 MHz): 12.915 (COOH-1, 1), broad; 7.03 ppm (H-22, 1), t, J=7.8 Hz; 6.76 ppm (H-23, 1), d, J=7.4 Hz; 6.68 ppm (H-21, 1), d, J=8.2 Hz; 4.62 ppm (H-2, 2), s; 4.47 ppm (OH-11, 1), broad; 4.21 ppm (OH-15, 1), broad; 3.47 ppm (H-11, 1), m (q), J~8.0 Hz; 3.35 ppm (H-15, 1), m, 2.80-2.60 ppm (H-4a and H-7a, 2), m (in: 2.725 ppm (H-4a, 1), dd, J=14.7 Hz and 6.2 Hz; 2.67 ppm (H-7a, 1), dd, J=14.2 Hz and 6.2 Hz); 2.48-2.34 ppm (H-4b and H-7b, 2), m (in: 2.49 ppm (H-4b, 1), dd, J=14.6 Hz and 6.6 Hz; 2.39 ppm (H-7b, 1), dd, J=14.2 Hz and 6.5 Hz); 2.11 ppm (H-9, 1), m (tq), J~10.1 Hz and ~6.7 Hz; 1.955 ppm (H-10a, 1), m (ddd/dt), J=12.1 Hz and 6.7 Hz; 1.76 ppm (H-8, 1), m (tt), J=10.0 Hz and 6.2 Hz; 1.61 ppm (H-13a, 1) m; 1.53-1.33 ppm (H-14, H-16a and H-17a, 4), m (in:1.46 ppm (H-14a, 1), m; 1.43 ppm (H-14b, 1), m; 1.38 ppm (H-17a, 1), m; 1.35 ppm (H-16a, 1), m); 1.33-1.15 ppm (H-13b, H-16b, H-17b, H-18 and H-19, 7), m (in: 1.32 ppm (H-13b, 1), m; 1.30 ppm (H-16b, 1), m; 1.275 ppm (H-19, 2), m; 1.26 ppm (H-17b, 1), m; 1.25 ppm (H-18, 2), m); 1.15-0.93 ppm (H-10b, H-13, 2), m (in: H-1.09 ppm (H-12, 1), m (tt), J=9.0 Hz and 6.1 Hz; 1.00 ppm (H-10b, 1), m (ddd/dt), J=11.7 Hz and 10.2 Hz); 0.87 ppm (H-20, 3), m (t), J=6.9 Hz; 13C NMR (100 MHz): 170.36 ppm (C-1), 154.63 ppm (C-3), 140.56 ppm (C-6), 126.75 ppm (C-5), 125.85 (C-22), 120.65 ppm (C-23), 109.37 ppm (C-21), 75.44 ppm (C-11), 70.13 ppm (C-15), 64.96 ppm (C-2), 51.49 ppm (C-12), 41.15 ppm (C-10), 40.48 ppm (C-8), 37.06 ppm (C-16), 35.03 ppm (C-14), 33.37 ppm (C-7), 32.42 ppm (C-9), 31.53 ppm (C-18), 28.36 ppm (C-13), 25.62 ppm (C-4), 24.96 ppm (C-17), 22.18 ppm (C-19), 13.96 ppm (C-20).

1s.) Preparation of (1R,2R,3aS,9aS)-2-[2-Hydroxy-1-[3(S)-hydroxyoctyl]-2,3,3a,4,9,9a-hexahydro-1H-benz[f]inden-5-yloxy]acetic Acid Sodium Salt (Treprostinil Sodium Salt)

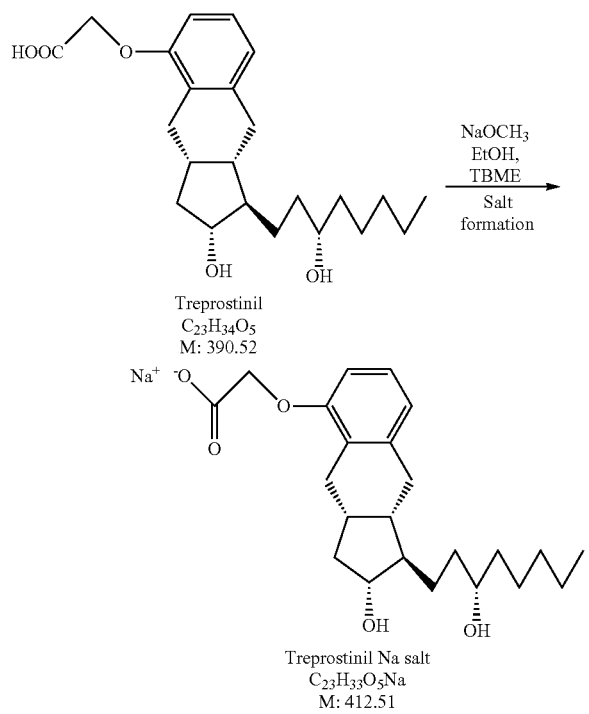

1s1.) 150 g (0.384 mol) of treprostinil is dissolved in 2 l of ethanol. Sodium carbonate monohydrate 26.2 g (0.211 mol) is added to it and under an inert atmosphere the mixture is stirred at room temperature. When the pH of a filtered sample reaches the value of 7-9, the mixture is filtered through a 5 μm pore size filter. The filtrate solution is concentrated on rotadest to approx. 225 g. The concentrate is dissolved in tert-butyl methyl ether which has been saturated with water and allowed to crystallize at room temperature. The crystals are filtered off, washed at room temperature and dried in vacuum at 20-50° C.

Yield: 158 g (100%) of treprostinil sodium salt monohydrate (form "A"), white crystals. Mp: 95-99° C.

1s2.) 150 g (0.384 mol) of treprostinil is dissolved in 2 l of ethanol. 35.5 g (0.422 mol) of sodium hydrogen carbonate is added to it and under an inert atmosphere the mixture is stirred at room temperature. When the pH of a filtered sample reaches the value of 7-8, the mixture is filtered through a 5 μm pore size filter and the filtrate solution is concentrated on rotadest to approx. 225 g. The concentrate is dissolved in tert-butyl methyl ether which has been saturated with water and allowed to crystallize at room temperature. The crystals are filtered off, washed at room temperature and dried in vacuum at 20-50° C.

Yield: 158 g (100%) of treprostinil sodium salt monohydrate (form "A"), white crystals. Mp: 95-99° C.

1s3.) 150 g (0.384 mol) of treprostinil is dissolved in 2 l of ethanol. 21 g (0.39 mol) of sodium methylate is added to it and under an inert atmosphere the mixture is stirred at room temperature until dissolution. The solution is filtered through a 5 μm pore size filter. The filtrate solution is concentrated on rotadest to approx. 225 g. The concentrate is dissolved in tert-butyl methyl ether which has been saturated with water and allowed to crystallize at room temperature. The crystals are filtered off, washed at room temperature and dried in vacuum at 20-50° C.

Yield: 158 g (100%) of treprostinil sodium salt monohydrate (form "A"), white crystals. Mp: 95-99° C.

1s4.) 24 g (61.45 mmol) of treprostinil is dissolved in 360 ml of ethanol and 7.62 g (61.45 mmol) of sodium carbonate monohydrate is added to it. The mixture is stirred under an inert atmosphere at room temperature till complete dissolution. The solution is then filtered through a 5 μm pore size filter and the filtrate solution is concentrated on rotadest. To the concentrate ethanol is added and the solution is concentrated again. The concentrate is dissolved in tert-butyl methyl ether and allowed to crystallize at room temperature. The crystals are collected by filtration, washed and dried in vacuum at 20-50° C.

Yield: 22.8 g (90%) of treprostinil sodium salt, white solid (amorphous form).

Mp: 65-90° C.

Analytical characterisation of treprostinil sodium salt monohydrate (form "A"):

Mp: 95-99° C.
DSC peak: 94-99° C.
Purity: 99.9 by HPLC area %
15-epi-treprostinil: 0.0 by HPLC area %
Water content: 4.3%
Specific optical rotation (c=1%, methanol 25° C.): +41°
Sulfated ash: 16.8%
NMR data: (d6-DMSO), 1H NMR (500 MHz): 6.95 ppm (H-22, 1), t, J=7.8 Hz; 6.65 ppm (H-23, 1), d, J=7.4 Hz; 6.61 ppm (H-21, 1), d, J=8.2 Hz; 4.97-3.93 ppm (H-2, OH-11 and OH-15, 4), m (in: 4.54 ppm (OH-11, 1), broad; 4.32 ppm (OH-15, 1), broad; 4.13 ppm (H-2, 2), s); 3.47 ppm (H-11, 1), td, J~9.4 Hz and 6.2 Hz; 3.35 ppm (H-15, 1), m (tt), J~7.0 Hz and 4.3 Hz; 2.75 ppm (H-4a, 1), dd, J=14.5 Hz and 6.1 Hz; 2.65 ppm (H-7a, 1), dd, J=14.1 Hz and 6.1 Hz; 2.42-2.32 ppm (H-4b and H-7b, 2), m (in: 2.38 ppm (H-4b, 1), dd, J=14.5 Hz and 6.8 Hz; 2.355 ppm (H-7b, 1), dd, J=14.1 Hz and 6.9 Hz); 2.08 ppm (H-9, 1), m (tq), J~10.1 Hz and ~7.0 Hz; 1.96 ppm (H-10a, 1), m (ddd/dt), J=12.1 Hz and 6.6 Hz; 1.73 ppm (H-8, 1), m (tt), J=9.8 Hz and 6.7 Hz; 1.61 ppm (H-13a, 1) m; 1.52-1.32 ppm (H-14, H-16a and H-17a, 4), m (in:1.455 ppm (H-14a, 1), m; 1.42 ppm (H-14b, 1), m; 1.38 ppm (H-17a, 1), m; 1.34 ppm (H-16a, 1), m); 1.32-1.16 ppm (H-13b, H-16b, H-17b, H-18 and H-19, 7), m (in: 1.31 ppm (H-13b, 1), m; 1.285 ppm (H-16b, 1), m; 1.275 ppm (H-19, 2), m; 1.26 ppm (H-17b, 1), m; 1.25 ppm (H-18, 2), m); 1.11 ppm (H-12, 1), m (tt), J=9.0 Hz and 6.3 Hz, 1.02 ppm (H-10b, 1), m (ddd/dt), J=11.3 Hz and 10.3 Hz); 0.865 ppm (H-20, 3), m (t), J=6.9 Hz;

13C NMR (125.8 MHz): 171.55 ppm (C-1), 155.89 ppm (C-3), 139.91 ppm (C-6), 126.38 ppm (C-5), 125.52 (C-22), 119.30 ppm (C-23), 109.74 ppm (C-21), 75.53 ppm (C-11), 70.14 ppm (C-15), 68.29 ppm (C-2), 51.58 ppm (C-12), 41.26 ppm (C-10), 40.63 ppm (C-8), 37.06 ppm (C-16), 35.07 ppm (C-14), 33.59 ppm (C-7), 32.55 ppm (C-9), 31.54 ppm (C-18), 28.40 ppm (C-13), 25.82 ppm (C-4), 24.97 ppm (C-17), 22.19 ppm (C-19), 13.98 ppm (C-20).

DSC diagram of treprostinil sodium salt monohydrate (form "A") is shown on FIGS. 2 and 3.

XRPD diagram of treprostinil sodium salt monohydrate (form "A") is shown on FIG. 7.

1t.) Preparation of treprostinil sodium salt anhydrate (form "B") Mp.: 125-129° C.):

1t1.) Any of the procedures of Examples 1s1-1 s2-1s3 may be followed with the exception that: the obtained crystals are filtered off, washed and dried in vacuum at 60-100° C.

1t2.) Any of the procedures of examples 1s1-1s2-1s3 may be followed, the obtained crystals are dried in vacuum at 60-100° C.

1t3.) Treprostinil sodium salt monohydrate is agitated in suspension at 60-90° C. for 1-6 hours in a solvent which does not or only sparingly dissolves it. The solvent may be e.g. hexane, heptane, toluene or ethyl acetate.

DSC diagram of treprostinil sodium salt anhydrate (form "B") is shown on FIGS. 4 and 5.

XRPD diagram of treprostinil sodium salt anhydrate (form "B") is shown on FIG. 8.

1v.) Preparation of treprostinil sodium salt polyhydrate (form "C"):

1v1.) Treprostinil sodium salt monohydrate (form "A") is kept in manipulator under an atmosphere of 60% moisture content for 48 hours, or treprostinil sodium salt monohydrate is kept under air for 5-8 days.

1v2.) Treprostinil sodium salt anhydrate (form "B") is kept in manipulator under an atmosphere of 60% moisture content for 48 hours, or is kept under air for 5-8 days.

DSC diagram of treprostinil sodium salt polyhydrate (form "C") is shown on FIG. 6.

XRPD diagram of treprostinil sodium salt polyhydrate (form "C") is shown on FIG. 9.

DSC diagram of treprostinil sodium salt (amorphous form) is shown on FIG. 1.

Characterisation of treprostinil sodium salts:

| Sodium salt | Sign of Form | DSC (peak, ° C.) | Purity (HPLC area %) | Water content (%) | Number of crystal-waters |
|---|---|---|---|---|---|
| monohydrate | A | 94-99 | 99.9 | 4.3-4.4 | 1 |
| anhydrate | B | 125-129 | 99.8 | max 0.5 | 0 |
| polyhydrate | C | 48-52 peak approx. 100° C. (flat) | 99.8 | 17-20 | not defined (3-5) |
| anhydrate | amorph | — | 99.9 | max 0.5 | 0 |

Termogravimetric analysis (TGA) has been carried out by TGA/SDTA851$^e$, Mettler Toledo instrument.

Differential scanning calorimetrical analysis has been carried out by DSC 1 Stare System, Mettler Toledo.

XRPD analysis has been carried out by XPERT-PRO-PANalytical instrument.

Following experimental conditions have been used:

X-ray tube name: PW3373/10 Cu, anode material: Cu

Used wavelength: intended wavelength type: K$\alpha$, K$\alpha_1$ (Å): 1,540598

Scan range (°): 2,0000-40,0014

Example 2

2a.) Preparation of 2-pent-4-ynoxy-tetrahydropyran (MPKO-1)

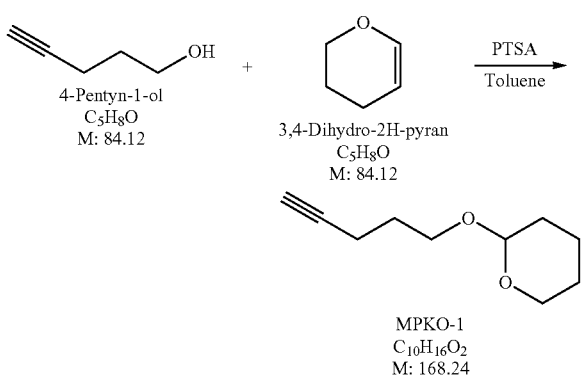

In 5.5 l of distilled toluene 552 g of 4-pentyn-1-ol is dissolved. To the solution are added 677 ml of dihydropyran and the solution of 19.5 g of para-toluenesulfonic acid (PTSA) in 120 ml tetrahydrofuran. The reaction mixture is stirred at room temperature. At the end of the reaction the mixture is quenched with triethylamine, washed with sodium hydrogen carbonate solution and with water. The organic phase is evaporated. The crude product is taken into the next step without purification.

Yield: 1062 g (96%) of colourless oil.

NMR data:

(CDCl3), 1H NMR (500 MHz): 4.59 ppm (H-6, 1), dd, J=4.0 Hz and 3.1 Hz; 3.90-3.79 ppm (H-1a and H-10a, 2), m, (in: 3.86 ppm (H-10a, 1), ddd, J=11.3 Hz, 8.2 Hz and 3.2 Hz; 3.82 ppm (H-1a, 1), dt, J=9.8 Hz and 6.2 Hz); 3.54-3.44 ppm (H-1b and 10Hb, 2), m, (in: 3.50 ppm (H-10b, 1), m; 3.48 ppm (H-1b, 1), dt, J=9.8 Hz and 6.2 Hz); 2.31 ppm (H-3, 2), m (tdd), J=7.1 Hz, 2.5 Hz and 1.5 Hz; 1.94 ppm (H-5, 1), t, J=2.6 Hz; 1.87-1.765 ppm (H-2 and H-8a, 3), m (tt/qui), (in: 1.81 ppm (H-2, 2), qui/tt, J=6.6 Hz; 1.82 ppm (H-8a, 1), m); 1.70 ppm (H-7a, 1), m; 1.615-1.47 ppm (H-7a, H-8a, H-9, 4), m, (in: 1.58 ppm (H-7b, 1), m; 1.57 ppm (H-9a, 1), m, 1.525 ppm (H-9b, 1), m; 1.52 ppm (H-8b, 1), m);

13C NMR (125.8 MHz): 98.95 ppm (C-6), 84.13 ppm (C-4), 68.56 ppm (C-5), 65.93 ppm (C-1), 62.35 ppm (C-10), 30.81 ppm (C-7), 28.84 ppm (C-2), 25.61 ppm (C-9), 19.65 ppm (C-8), 15.48 ppm (C-3).

2b.) Preparation of 1-(2-allyl-3-methoxyphenyl)-6-tetrahydropyran-2-yloxy-hex-2-yn-1-ol (MPK-1)

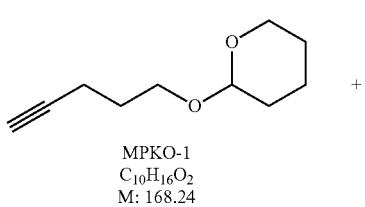

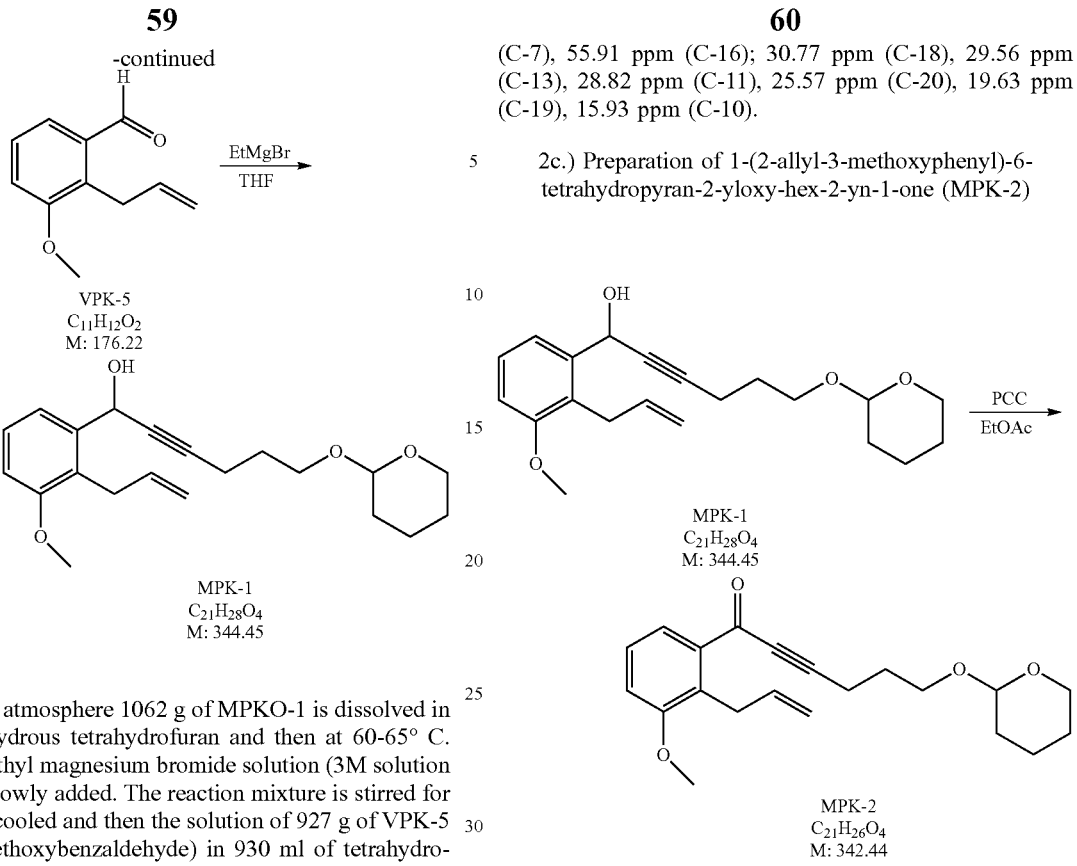

In an inert atmosphere 1062 g of MPKO-1 is dissolved in 8.5 l of anhydrous tetrahydrofuran and then at 60-65° C. 1920 ml of ethyl magnesium bromide solution (3M solution in ether) is slowly added. The reaction mixture is stirred for 45 minutes, cooled and then the solution of 927 g of VPK-5 (2-allyl-3-methoxybenzaldehyde) in 930 ml of tetrahydrofuran is added to it. At the end of the reaction the mixture is quenched with 1M $NaHSO_4$ solution, the aqueous phase is extracted with ethyl acetate, the united organic phase is washed with 0.5M $NaHCO_3$ solution and 15% NaCl solution, dried and concentrated to 2.4 kg. The concentrated crude product is taken into the next step without purification.

Yield: 100% (1812 g) of MPK-1, as light brown oil.

NMR data:

(CDCl3), 1H NMR (500 MHz): 7.34 ppm (H-6, 1), dd, J=7.8 Hz and 0.7 Hz; 7.24 ppm (H-5, 1), m (t), J=8.0 Hz, partly overlapped with the peak of the residual CDCl3 solvent; 6.86 ppm (H-4, 1), d (dbroad), J=8.0 Hz; 5.985 ppm (H-14, 1), ddt, J=17.1 Hz, 10.2 Hz and 5.9 Hz; 5.62 ppm (H-7, 1), broad; 4.98 ppm (H-15a, 1), dq (ddt), J=10.1 Hz, 1.8 Hz and 1.6 Hz; 4.93 ppm (H-15b, 1), dq (ddt), J=17.1 Hz, 1.8 Hz and 1.7 Hz; 4.57 ppm (H-17, 1), m, J=2.5 Hz; 3.88-3.77 ppm (H-12a, H-16 és H-21a, 5), m, (in: 3.85 ppm (H-21a, 1), m; 3.82 ppm (H-16, 3), s; 3.81 ppm (H-12a, 1), dd, 15.9 Hz and 6.2 Hz); 3.625 ppm (H-13a, 1), ddt, J=15.7 Hz, 5.8 Hz and 1.6 Hz; 3.55 ppm (H-13b, 1), ddt, J=15.7 Hz, 5.9 Hz and 1.6 Hz; 3.505-3.43 ppm (H-12b and H-21b, 2), m, (in: 3.47 ppm (H-21b, 1), m; 3.46 ppm (H-12b, 1), m); 2.37 ppm (H-10, 2), td, J=7.1 Hz and 1.8 Hz; 2.30 ppm (OH-7, 1), broad; 1.87-1.75 ppm (H-11 and H-19a, 3), m, (in: 1.815 ppm (H-11, 2), tt (qui), J=6.7 Hz; 1.81 ppm (H-19a, 1), m); 1.69 ppm (H-18a, 1), m; 1.62-1.45 ppm (H-18b, H-19b and H-20, 4), m, (in: 1.565 ppm (H-18b, 1), m; 1.56 ppm (H-20a, 1), m; 1.51 ppm (H-20b, 1), m; 1.505 ppm (H-19b, 1) m);

13C NMR (125.8 MHz): 157.74 ppm (C-3), 140.75 ppm (C-1), 137.20 ppm (C-14), 127.52 ppm (C-5), 125.94 pm (C-2), 119.32 ppm (C-6), 114.86 ppm (C-15), 110.74 ppm (C-4), 98.90 ppm (C-17); 86.66 ppm (C-9), 80.55 ppm (C-8), 66.03 ppm (C-12), 62.32 ppm (C-21), 62.23 ppm (C-7), 55.91 ppm (C-16); 30.77 ppm (C-18), 29.56 ppm (C-13), 28.82 ppm (C-11), 25.57 ppm (C-20), 19.63 ppm (C-19), 15.93 ppm (C-10).

2c.) Preparation of 1-(2-allyl-3-methoxyphenyl)-6-tetrahydropyran-2-yloxy-hex-2-yn-1-one (MPK-2)

To 12 l of ethyl acetate in an inert atmosphere 4 kg of pyridinium chlorochromate (PCC) and then 1.7 kg of anhydrous sodium acetate are added. The suspension is stirred at room temperature for 15 minutes, then the 2.4 kg of MPK-1 solution obtained in the previous step is added. At the end of the reaction diisopropyl ether and silica gel are added to the mixture. After 15-20 minutes of stirring the mixture is filtered, the silica gel is washed with ethyl acetate and the filtrate solution is evaporated. The crude product is purified by chromatography on silica gel column using gradient mixtures of hexane: ethyl acetate as eluent. The fractions which contain the product are collected, concentrated, washed with water, dried over sodium sulfate, the drying material is filtered off and the filtrate solution is evaporated.

Yield: 1246 g (69%) of light brown oil.

NMR data:

(CDCl3), 1H NMR (500 MHz): 7.73 ppm (H-6, 1), dd, J=7.8 Hz and 0.7 Hz; 7.29 ppm (H-5, 1), t, J=8.0 Hz; 7.04 ppm (H-4, 1), d (dbroad), J=8.0 Hz; 5.97 ppm (H-14, 1), ddt, J=17.1 Hz, 10.1 Hz and 6.2 Hz; 4.985 ppm (H-15b, 1), dq (ddt), J=17.1 Hz and 1.7 Hz; 4.94 ppm (H-15a, 1), dq (ddt), J=10.1 Hz and 1.6 Hz; 4.60 ppm (H-11, 1), m (dd), J~4.0 Hz and 2.9 Hz; 3.91-3.81 ppm (H-12a, H-16 and H-21a, 5), m, (in: 3.86 ppm (H-12a, 1), m, 3.855 ppm (H-21a, 1), m; 3.85 ppm (H-16, 3), s); 3.78 ppm (H-13, 2), dt, J=6.2 Hz and 1.5 Hz; 3.55-3.46 ppm (H-12b and H-21b, 2), m, (in: 3.51 ppm (H-12b, 1), m (dt), J=9.9 Hz and 6.0 Hz; 3.50 ppm (H-21b, 1), m); 2.585 ppm (H-10, 2), td, J=7.1 Hz and 1.4 Hz; 1.925 ppm (H-11, 2), tt (qui), J=6.6 Hz; 1.82 ppm (H-19a, 1), m; 1.71 ppm (H-18a, 1), m; 1.64-1.46 ppm (H-18b, H-19b and H-20, 4), m, (in: 1.575 ppm (H-18b, 1), m; 1.57 ppm (H-20a, 1), m; 1.53 ppm (H-20b, 1), m; 1.52 ppm (H-19b, 1) m); 13C NMR (125.8 MHz): 180.21 ppm (C-7), 158.20 ppm (C-3), 137.53 ppm (C-1), 136.90 ppm (C-14), 130.04 pm (C-2), 126.85 ppm (C-5), 124.75 ppm (C-6), 115.01 ppm (C-4), 114.89 ppm (C-15), 99.05 ppm (C-17); 95.03 ppm (C-9), 81.97 ppm (C-8), 65.84 ppm (C-12), 62.46 ppm (C-21), 56.20 ppm (C-16); 30.78 ppm (C-18), 29.89 ppm (C-13), 28.23 ppm (C-11), 25.58 ppm (C-20), 19.68 ppm (C-19), 16.38 ppm (C-10).

2d.) Preparation of (1S)-1-(2-allyl-3-methoxyphenyl)-6-tetrahydropyran-2-yloxy-hex-2-yn-1-ol (MPK-3)

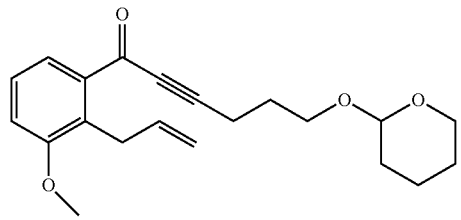

MPK-2
C$_{21}$H$_{26}$O$_4$
M: 342.44

R—Me—CBS-oxazaborolidine
(CH$_3$)$_2$SBH$_3$
$\xrightarrow{\text{THF}}$

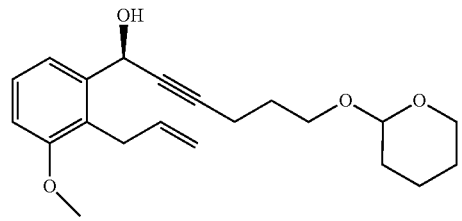

MPK-3
C$_{21}$H$_{28}$O$_4$
M: 344.45

Under an inert atmosphere 1246 g of MPK-2 is dissolved in 6.3 l of anhydrous tetrahydrofuran. The solution is cooled to 0-5° C. and 5.73 l of R-(+)-2-methyl-CBS-oxazaborolidine in 1M toluene solution is added. The mixture is then cooled to (–40)-(–35°) C and 925 ml of borane-dimethyl sulfide complex is added. At the end of the reaction the mixture is quenched with methanol and 5% NH$_4$Cl solution, the aqueous phase is extracted with ethyl acetate, the organic phase is washed with water, dried, filtered and evaporated. The crude product is purified by chromatography on silica gel column using hexane: ethyl acetate mixtures eluents.

Yield: 1178 g (94%) of light brown oil.

NMR data:

(CDCl3), 1H NMR (500 MHz): 7.35 ppm (H-6, 1), d, J=7.8 Hz, 7.24 ppm (H-5, 1), m (t), J=8.0 Hz, 6.86 ppm (H-4, 1), d, J=8.1 Hz; 5.99 ppm (H-14, 1), ddt, J=17.1 Hz, 10.3 Hz and 5.7 Hz; 5.62 ppm (H-7, 1), t, J=1.8 Hz; 4.98 ppm (H-15a, 1), dq, J=10.1 Hz és 1.8 Hz; 4.94 ppm (H-15b, 1), dq, J=17.2 Hz and 1.7 Hz; 4.57 ppm (H-17, 1), m, J=2.4 Hz; 3.91-3.74 ppm (H-12a, H-16 and H-21a, 5), m, (in: 3.84 ppm (H-21a, 1), m; 3.82 ppm (H-16, 3), s; 3.82 ppm (H-12a, 1), m); 3.63 ppm (H-13a, 1), ddt, J=15.6 Hz, 5.8 Hz and 1.7 Hz; 3.55 ppm (H-13b, 1), ddt, J=15.6 Hz, 5.8 Hz and 1.7 Hz; 3.51-3.41 ppm (H-12b and H-21b, 2), m, (in: 3.475 ppm (H-21b, 1), m; 3.47 ppm (H 12b, 1), m (dt), J=9.7 Hz and 6.1 Hz); 2.1144-2.20 ppm (OH-7 and H-10, 3), m, (in: 2.37 ppm (H-10, 2), td, J=7.1 Hz and 1.6 Hz; 2.30 ppm (OH-7, 1), broad); 1.90-1.75 ppm (H-11 and H-19a, 3), m, (in: 1.815 ppm (H-11, 2), tt (qui), J=6.7 Hz; 1.81 ppm (H-19a, 1), m); 1.69 ppm (H-18a, 1), m; 1.62-1.44 ppm (H-18b, H-19b and H-20, 4), m, (in: 1.57 ppm (H-18b, 1), m; 1.56 ppm (H-20a, 1), m; 1.515 ppm (H-20b, 1), m; 1.51 ppm (H-19b, 1) m);

13C NMR (125.8 MHz): 157.76 ppm (C-3), 140.77 ppm (C-1), 137.20 ppm (C-14), 127.51 ppm (C-5), 125.96 pm (C-2), 119.33 ppm (C-6), 114.85 ppm (C-15), 110.75 ppm (C-4), 98.91 ppm (C-17); 86.66 ppm (C-9), 80.57 ppm (C-8), 66.03 ppm (C-12), 62.32 ppm (C-21), 62.24 ppm (C-7), 55.91 ppm (C-16); 30.77 ppm (C-18), 29.56 ppm (C-13), 28.83 ppm (C-11), 25.58 ppm (C-20), 19.63 ppm (C-19), 15.93 ppm (C-10).

2e.) Preparation of [(1S)-1-(2-allyl-3-methoxyphenyl)-6-tetrahydropyran-2-yloxy-hex-2-yn-1-oxy]tert-butyldimethylsilane (MPK-4)

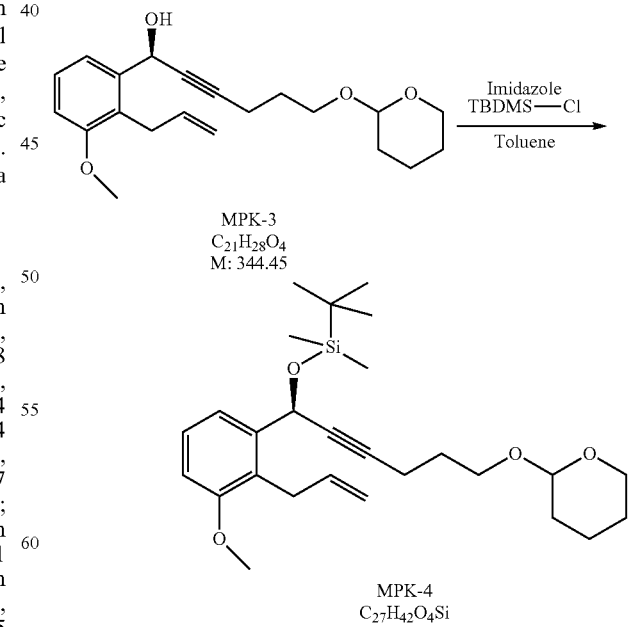

MPK-3
C$_{21}$H$_{28}$O$_4$
M: 344.45

Imidazole
TBDMS—Cl
$\xrightarrow{\text{Toluene}}$

MPK-4
C$_{27}$H$_{42}$O$_4$Si
M: 458.72

The crude MPK-3 obtained in the previous step (theoretical amount 1253 g) is dissolved in 10 l of toluene and to the solution 409 g of imidazole is added. The reaction mixture is cooled to 5-10° C. and 2.02 l of tert-butyldimethylchlorosilane (TBDMS-CI) in 50% toluene solution is added. The mixture is stirred at room temperature. At the end of the reaction water is added to the mixture and the insoluble impurities are filtered off. The filtrate residue is washed with toluene, the phases of the filtrate are separated, the organic phase is evaporated. The crude product is purified by chromatography on silica gel column using hexane: ethyl acetate mixtures as eluent.

Yield: 1515 g (91%) of light brown oil.

NMR data:

(CDCl3), 1H NMR (500 MHz): 7.27 ppm (H-6, 1), m (d/dd), J=8.0 Hz and 1.0 Hz, 7.21 ppm (H-5, 1), t, J=8.0 Hz; 6.81 ppm (H-4, 1), d(dd), J=8.1 Hz and 0.7 Hz; 5.95 ppm (H-14, 1), dddd, J=16.9 Hz, 10.3 Hz, 6.4 Hz and 5.4 Hz; 5.575 ppm (H-7, 1), t, J=1.7 Hz; 5.00-4.90 ppm (H-15, 2), m, (in: 4.97 ppm (H-15a, 1), dq, J~10.2 Hz and 1.6 Hz; 4.94 ppm (H-15b, 1), dq, J~16.9 Hz and 1.8 Hz); 4.55 ppm (H-17, 1), m; 3.87-3.73 ppm (H-12 the two diastereomers, H-16 and H-21a, 5), m, (in: 3.83 ppm (H-21a, 1), m; 3.81 ppm (H-16, 3), s; 3.780 ppm and 3.778 ppm (H-12a, 1), dt, J~9.8 Hz and 6.3 Hz); 3.61 ppm (H-13a, 1), ddt, J=15.6 Hz, 5.2 Hz and 1.8 Hz; 3.55-3.38 ppm (H-12b, H-13b and H-21b, 3), m, (in: 3.505 ppm (H-13b. 1), m (dd), J=15.6 Hz and 6.4 Hz; 3.46 ppm (H-21b, 1), m; 3.42 ppm (H-12b, 1), dt, J=9.8 Hz and 6.3 Hz); 2.295 ppm (H-10, 2), m (td), J=7.2 Hz and 1.9 Hz; 1.86-1.73 ppm (H-11 and H-19a, 3), m, (in: 1.805 ppm (H-19a, 1), m; 1.77 ppm (H-11, 2), tt (qui), J=6.7 Hz); 1.68 ppm (H-18a, 1), m; 1.64-1.45 ppm (H-18b, H-19b és H-20, 4), m, (in: 1.56 ppm (H-20a, 1), m; 1.55 ppm (H-18b, 1), m; 1.51 ppm (H-20b, 1), m; 1.50 ppm (H-19b, 1) m); 0.91 ppm (H-24, H-25 and H-26, 9), m (s), 0.12 ppm (H-22/H-23, 3), s, 0.09 ppm (H-23/H-22, 3), s.

13C NMR (125.8 MHz): 157.47 ppm (C-3), 142.27 ppm (C-1), 136.71 ppm (C-14), 127.20 ppm (C-5), 124.75 pm (C-2), 118.64 ppm (C-6), 114.61 ppm (C-15), 109.88 ppm (C-4), 98.95 ppm (C-17); 85.12 ppm (C-9), 81.51 ppm and 81.50 ppm (C-8), 66.15 ppm and 66.13 ppm (C-12), 62.45 ppm (C-21), 62.30 ppm (C-7), 55.81 ppm (C-16); 30.79 ppm (C-18), 29.58 ppm (C-13), 28.86 ppm and 28.84 (C-11), 25.99 ppm (C-25, C-26 and C-27, 3), 25.60 ppm (C-20), 19.67 ppm (C-19), 18.45 ppm (C-24), 15.93 ppm (C-10), −4.36 ppm (C-22/C-23), −4.69 ppm (C-23/C-22).

2f.) Preparation of (9R)-9-[tert-butyl(dimethyl)silyl]oxy-5-methoxy-1-(3-tetrahydropyran-2-yloxypropyl)-3,3a,4,9-tetrahydrocyclopenta[b]naphthalen-2-one (MPK-5)

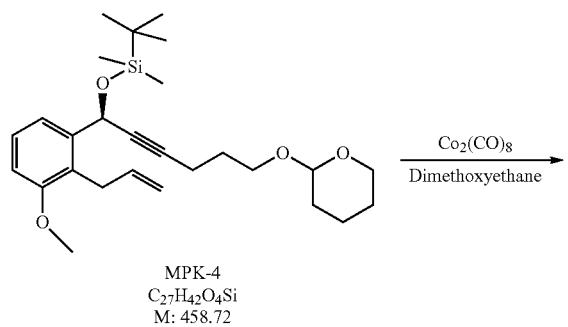

MPK-4
$C_{27}H_{42}O_4Si$
M: 458.72

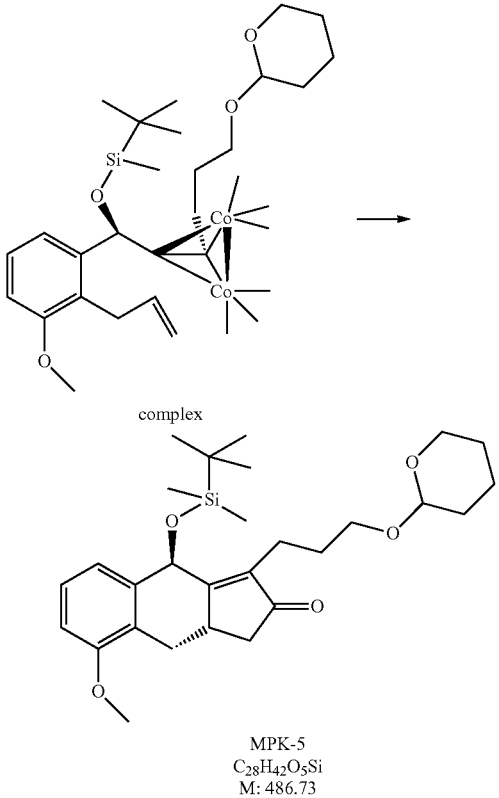

MPK-5
$C_{28}H_{42}O_5Si$
M: 486.73

In 11.5 l of dimethoxyethan, in an inert atmosphere, 1427 g of MPK-4 is dissolved and then 1070 g of dicobalt octacarbonyl is added. The reaction mixture is stirred at room temperature for 2.5 hours, then it is heated to 60-70° C. and stirred for 3 hours. At the end of the reaction air is bubbled through the mixture. Bubbling is continued overnight. The reaction mixture is then filtered, washed with ethyl acetate and evaporated. The crude product is purified by chromatography on silica gel column using hexane: diisopropyl ether mixtures as eluent.

Yield: 1363 g (90%) of light brown oil.

NMR data:

(CDCl3), 1H NMR (500 MHz): 7.22 ppm (H-22, 1), t, J=7.9 Hz; 6.96-6.87 ppm (H-23, 1), m (in: 6.93 ppm (H-23, 0.5) d, J=7.7 Hz; 6.90 ppm (H-23, 0.5), d, J=7.7 Hz); 6.78 ppm (H-21, 1), d, J=8.1 Hz; 5.55 ppm (H-7, 0.5), s; 5.21 ppm (H-7, 0.5), s; 4.50 ppm (H-24, 0.5), m (dd), J=4.1 Hz and 2.9 Hz; 4.26 ppm (H-24, 0.5), m (dd), J=4.1 Hz and 2.9 Hz; 3.84-3.74 ppm (H-2, H-28, 3.5), m (in: 3.81 ppm (H-2, 3), s; 3.78 ppm (H-28, 0.5), m (ddd), J=11.3 Hz, 8.2 Hz and 3.2 Hz); 3.70 ppmn (H-28, 0.5), ddd, J=11.3 Hz, 8.0 Hz and 3.2 Hz; 3.66-3.55 ppm (H-15a, 1), m (in: 3.63 ppm (H-15a, 0.5), dt, J=9.9 Hz and 5.3 Hz; 3.58 ppm (H-15a, 0.5), ddd, J=9.9 Hz, 7.4 Hz and 5.6 Hz); 3.55-3.47 ppm (H-4a, 1), m (in: 3.52 ppm (H-4a, 0.5), dd, J=17.1 Hz and 7.4 Hz; 3.51 ppm (H-4a, 0.5), dd, J=17.0 and 7.4 Hz); 3.43-3.27 ppm (H-9, H-15b, H-28b, 2.5), m (in: 3.38 ppm (H-28b, 1), m; 3.35 ppm (H-9, 1), m; 3.315 ppm (H-15b, 0.5), m(dt), J~9.9 Hz and 5.9 Hz); 3.06 ppm (H-15b, 0.5), ddd, J=9.5 Hz, 8.6 Hz and 4.8 Hz; 2.745-2.65 ppm (H-10a, 1), m (in: 2.702 ppm (H-10a, 0.5), dd, J=18.8 Hz and 6.4 Hz; 2.700 ppm (H-10a, 0.5), dd, J=18.8 Hz and 6.4 Hz); 2.46-2.30 ppm (H-13, 2), m (in: 2.42 ppm (H-13a, 0.5), m; 2.40 ppm (H-13a, 0.5), m; 2.385 ppm (H-13b, 0.5), m; 2.34 ppm (H-13b, 0.5), m); 2.25-2.18 ppm (H-10b, 1), m (in: 2.212 ppm (H-10b, 0.5), dd, J=18.8 Hz and 1.3 Hz; 2.210 ppm (H-10b, 0.5), dd, J=18.8 Hz and 1.3 Hz); 2.175-2.07 ppm (H-4b, 1), m (in: 2.13 ppm (H-4b, 0.5), dd, J=17.1 Hz and 8.9 Hz; 2.115 ppm (H-4b, 0.5), dd, J=17.1 and 8.9 Hz); 1.875-1.72 ppm (H-14a and H-26, 2), m (in: 1.80 ppm (H-26, 1), m; 1.78 ppm (H-14a, 0.5), m; 1.75 ppm (H-14a, 0.5), m); 1.72-1.58 ppm (H-14b and H-25a, 2), m (in: 1.64 ppm (H-25a, 1), m; 1.63 ppm (H-14b, 1), m); 1.58-1.38 ppm (H-25b, H-26b and H-27, 4), m (in: 1.53 ppm (H-25b, 1), m; 1.51 ppm (H-27b, 1) m; 1.48 ppm (H-26b, 1), m; 1.41 ppm (H-27b, 1), m); 0.82 ppm (H-32, H-33 and H-34, 9), s; 0.16-0.12 ppm (H-29/H-30, 3), m (s) (in: 0.143 ppm (H-29/H-30, 1.5), s; 0.135 ppm (H-29/H-30, 1.5), s); 0.10-0.055 ppm (H-30/H-29, 3), m (in: 0.082 ppm (H-30/H-29, 1.5), s, 0.077 ppm (H-30/H-29, 1.5), s, 13C NMR (125.8 MHz): 209.78 ppm (C-11), 173.52 ppm and 173.25 ppm (C-8), 156.95 ppm and 156.92 ppm (C-3), 138.43 ppm and 138.36 ppm (C-6), 136.94 ppm and 136.64 ppm (C-12), 127.45 ppm and 127.39 ppm (C-22), 125.11 pm and 125.10 ppm (C-5), 122.25 ppm and 122.12 ppm (C-23), 109.32 ppm and 109.31 ppm (C-21), 98.82 ppm and 98.73 ppm (C-24), 66.64 ppm and 65.97 ppm (C-15), 65.34 ppm and 65.23 ppm (C-7), 62.36 ppm and 62.26 ppm (C-28), 55.45 ppm (C-2); 42.32 ppm and 42.29 ppm (C-10), 33.76 ppm and 33.50 ppm (C-4), 32.33 ppm and 32.31 ppm (C-9), 30.87 ppm and 30.84 ppm (C-25), 28.56 ppm and 28.21 ppm (C-14), 25.77 ppm (C-32, C-33 and C-34, 3), 25.58 ppm (C-27), 19.80 ppm and 19.68 ppm (C-26), 18.21 ppm and 18.20 ppm (C-31), −4.01 ppm and −4.03 ppm (C-29/C-30), −4.15 ppm (C-30/C-29).

2g.) Preparation of(9aS)-5-methoxy-1-(3-tetrahydropyran-2-yloxypropyl)-1,3,3a,4,9,9a-hexahydrocyclopenta[b]naphth-2-one (MPK-6)

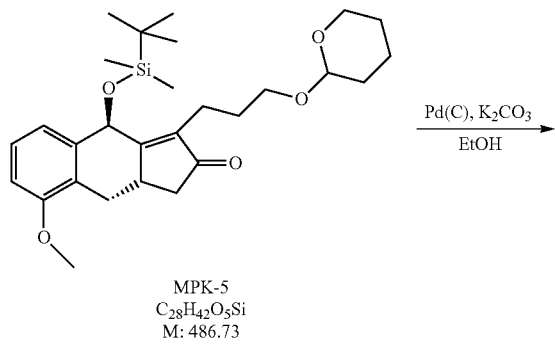

MPK-5
C<sub>28</sub>H<sub>42</sub>O<sub>5</sub>Si
M: 486.73

→ Pd(C), K₂CO₃, EtOH

MPK-6
C₂₂H₃₀O₄
M: 358.48

1363 g MPK-5 is dissolved in 5.5 l of ethyl alcohol, 60 g of potassium carbonate and 480 g of 10% Pd(C) catalyst are added and after proper inertisation the reaction mixture is stirred under 6 bar hydrogen pressure at room temperature. At the end of the reaction the catalyst is filtered off, washed with ethyl alcohol and the filtrate solution is evaporated. The crude product is purified by chromatography on silica gel column using hexane: ethyl acetate mixtures as eluent.

Yield: 703 g (70%) of light brown oil.

NMR data:
(CDCl3), 1H NMR (500 MHz): 7.10 ppm (H-22, 1), t, J=7.9 Hz, 6.74-6.64 ppm (H-21 and H-23, 2), m (in: 6.69 ppm (H-21, 1) d, J~8.4 Hz; 6.71 ppm (H-23, 1), d, J~8.3 Hz), 4.60 ppm (H-24, 1), m (dd), J=4.1 Hz and 3.0 Hz; 3.93-3.76 ppm (H-2, H-15a and H-28a, 5), m (in: 3.87 ppm (H-28a, 1), m; 3.82 ppm (H-2, 3), s; 3.805 ppm (H-15a, 1), m), 3.575-3.335 ppm (H-15b and H-28b, 2), m (in: 3.51 ppm (H-28b, 1), m; 3.44 ppm (H-15b, 1), m), 2.95 ppm (H-4a, 1), m (dd), J=18.3 Hz and 7.4 Hz, 2.80 ppm (H-4b, 1), d, J=18.2 Hz; 2.77-2.625 ppm (H-7a and H-9, 2), m (in: 2.74 ppm (H-7a, 0.5), m (dd), J=16.7 Hz and 5.9 Hz; 2.73 ppm (H-7a, 0.5). m (dd), J=16.7 Hz and 5.9 Hz; 2.68 ppm (H-9, 1), m), 2.56 ppm (H-8, 1), m (tt/qui), J=5.9 Hz and 5.5 Hz, 2.50-2.37 ppm (H-10a and H-12, 2), m (in: 2.44 ppm (H-10a, 1), dd, J=18.8 Hz and 8.2 Hz; 2.41 ppm (H-12, 1), m (ddd), J=5.5 Hz), 2.23 ppm (H-7b, 1), dd, J=16.5 Hz and 11.7 Hz. 2.00-1.79 ppm (H-10b, H-13a and H-26a, 3), m (in: 1.93 ppm (H-10b, 1), dd, J=18.9 Hz and 12.1 Hz; 1.905 ppm (H-13a, 1), m; 1.84 ppm (H-26a, 1), m), 1.79-1.64 ppm (H-14 and H-25a, 3), m (in: 1.79 ppm (H-25a, 1), m; 1.76 ppm (H-14a, 1), m; 1.71 ppm (H-14b, 1), m), 1.64-1.39 ppm (H-13b, H-25b, H-26b and H-27, 5), m (in: 1.59 ppm (H-25b, 1), m; 1.57 ppm (H-27a, 1), m; 1.53 ppm (H-26b, 1), m; 1.52 ppm (H-27b, 1), m; 1.45 ppm (H-13b, 1), m), 13C NMR (125.8 MHz): 219.34 ppm (C-11), 157.72 ppm (C-3), 136.06 and 136.04 ppm (C-6) 126.29 ppm (C-22), 123.37 ppm (C-5), 121.19 ppm (C-23), 107.46 ppm (C-21), 99.09 ppm and 98.96 ppm (C-24), 67.57 ppm and 67.45 ppm (C-15), 62.48 ppm (C-28), 56.82 ppm (C-12), 55.34 ppm (C-2), 41.86 ppm (C-10), 35.51 ppm (C-8), 31.69 ppm (C-9), 30.90 ppm and 30.87 ppm (C-25), 28.32 ppm and 28.28 ppm (C-14), 26.65 ppm (C-7), 25.60 ppm (C-27), 24.55 ppm (C-4), 21.48 ppm and 21.43 ppm (C-13), 19.77 ppm (C-26).

2h.) Preparation o(1 R,2R,9aS)-5-methoxy-1-(3-tetrahydropyran-2-yloxypropyl)-2,3,3a,4,9,9a-hexahydro-1H-cyclopenta[b]naphth-2-ol (MPK-7)

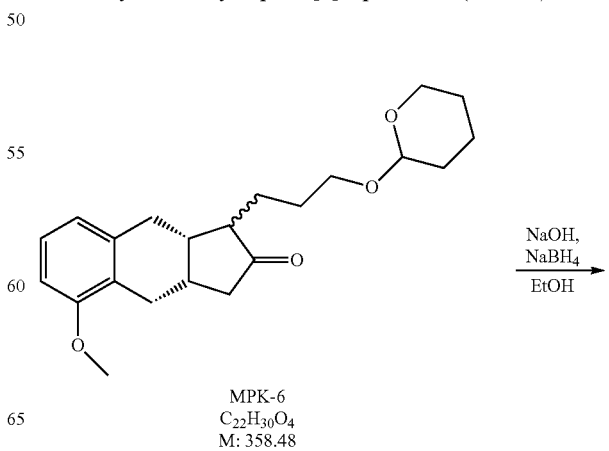

MPK-6
C₂₂H₃₀O₄
M: 358.48

→ NaOH, NaBH₄, EtOH

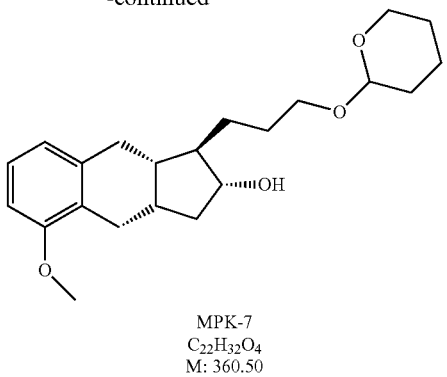

MPK-7
C₂₂H₃₂O₄
M: 360.50

703 g of MPK-6 is dissolved in 14 l of ethyl alcohol, the solution is cooled and at (−)15-(−10° C. 42 g of sodium borohydride is added. The reaction mixture is agitated. At the end of the reaction the mixture is quenched with acetic acid and the ethyl alcohol is distilled off. After the addition of water and ethyl acetate the phases are separated, the aqueous phase is extracted with ethyl acetate. The united organic phase is washed with 1M NaHCO₃ solution and water, dried, filtered and evaporated. The crude product is taken into the next step without purification.

Yield: 636 g (90%) of light brown oil.

NMR data:

(CDCl3), 1H NMR (500 MHz): 7.125-7.04 ppm (H-22, 1), m (in: 7.09 ppm (H-22, 0.5), t, J=7.8 Hz; 7.08 ppm (H-22, 0.5), t, J=7.8 Hz); 6.79-6.71 ppm (H-21 and H-23, 2), m (in: 6.760 ppm (H-21, 0.5), m (d), J=7.6 Hz; 6.754 ppm (H-21, 0.5), m (d), J=7.6 Hz; 6.738 ppm (H-23, 0.5), m (d), J~8.3 Hz; 6.735 ppm (H-23, 0.5), m (d), J=7.8 Hz); 4.63-4.52 ppm (H-24, 1), m (in: 4.585 ppm (H-24, 0.5), m (dd), J=4.1 Hz and 3.1 Hz; 4.56 ppm (H-24, 0.5), m (dd), J~4.3 Hz and 2.9 Hz); 3.87 ppm (H-28a, 0.5), m (ddd); 3.84-3.67 ppm (H-2, H-11, H-15a and H-28a, 5.5), m (in: 3.805 ppm (H-28a, 0.5), m; 3.80 ppm (H-2, 3), s; 3.795 ppm (H-15a, 0.5), m; 3.75 ppm (H-15a, 0.5), m; 3.715 ppm (H-11, 1), td, J=9.8 Hz and 6.2 Hz); 3.54-3.46 ppm (H-28b, 1), m (in: 3.50 ppm (H-28b, 0.5), m; 3.48 ppm (H-28b, 0.5), m)); 3.46-3.36 ppm (H-15b, 1), m (in: 3.43 ppm (H-15b, 0.5), dt, J=9.6 Hz and 6.2 Hz; 3.40 ppm (H-15b, 0.5), dt, J=9.6 Hz and 6.5 Hz); 2.82-2.70 ppm (H-4a and H-7a, 2), m (in: 2.775 ppm (H-4a, 1), dd, J=14.6 Hz and 6.1 Hz; 2.746 ppm (H-7a, 0.5), m (dd), J=14.1 Hz and 6.2; 2.741 ppm (H-7a, 0.5), m (dd), J=14.3 Hz and 6.2); 2.54-2.41 ppm (H-4b and H-7b, 2), m (in: 2.497 ppm (H-4b, 0.5), m (dd), J=14.7 Hz and 6.5 Hz; 2.492 ppm (H-4b, 0.5), m (dd), J=14.7 Hz and 6.4 Hz; 2.455 ppm (H-7b, 1), dd, J=14.3 Hz and 6.4 Hz); 2.30-2.04 ppm (H-9, H-10 and OH-11, 2.5), m (in: 2.249 ppm (H-9, 0.5), m (tt), J=10.3 Hz and 6.9 Hz; 2.214 ppm (H-9, 0.5), m (tt), J=10.0 Hz and 6.8 Hz; 2.16 ppm (H-10a, 1), m (dt/ddd), J=12.0 Hz, 7.1 Hz and 6.3 Hz; 2.15 ppm (OH-11, 0.5), broad); 2.00 ppm (OH-11, 0.5), 1.93-1.64 ppm (H-8, H-14, H-25a and H-26a, 5), m (in: 1.88 ppm (H-8, 1), m (tt), J=10.0 Hz and 6.3 Hz; 1.82 ppm (H-26a, 0.5), m; 1.795 ppm (H-14a, 1), m; 1.79 ppm (H-26a, 0.5), m; 1.755 ppm (H-14b, 1), m; 1.695 ppm (H-25a, 1), m); 1.64-1.44 ppm (H-13, H25b, H-26b and H-27, 6), m (in: 1.58 ppm (H-13a, 1), m; 1.565 ppm (H-25b, 1), m; 1.56 ppm (H-13b, 1), m; 1.555 ppm (H-27a, 1), m; 1.53 ppm (H-26b, 0.5), m; 1.505 ppm (H-27b, 1), m; 1.50 ppm (H-26b, 0.5), m); 1.38-1.20 ppm (H-12, 1), m (in: 1.32 ppm (H-12, 0.5), m, J~9.2 Hz and 6.6 Hz; 1.29 ppm (H-12, 0.5), m; J~9.2 Hz and 6.6 Hz), 1.19-1.08 ppm (H-10, 1), m (in: 1.16 ppm (H-10b, 0.5), m (ddd), J~10.0 Hz; 1.12 ppm (H-10b, 0.5), m (ddd), J~10.0 Hz);

13C NMR (125.8 MHz): 156.23 ppm (C-3), 140.64 ppm and 140.55 ppm (C-6), 127.04 ppm and 127.02 ppm(C-5) 126.20 ppm (C-22), 120.58 ppm (C-23), 108.43 ppm and 108.41 ppm (C-21), 99.09 ppm and 99.07 ppm (C-24), 77.37 ppm (C-11), 68.39 ppm and 68.36 ppm (C-15), 62.52 ppm and 62.42 ppm (C-28), 55.67 ppm (C-2), 51.96 ppm (C-12), 41.61 ppm and 41.41 ppm (C-8), 41.56 ppm and 41.53 ppm (C-10), 33.81 ppm and 33.76 ppm (C-7), 32.94 ppm (C-9), 30.81 ppm and 30.76 ppm (C-25), 29.90 ppm and 29.74 ppm (C-13), 27.73 ppm and 27.66 ppm (C-14), 25.83 ppm (C-4), 25.55 ppm and 25.52 ppm (C-27), 19.79 ppm and 19.69 ppm (C-26).

2i.) Preparation of [(1R,9aS)-5-methoxy-1-(3-tetra-hydropyran-2-yloxypropyl)-2,3,3a,4,9,9a-hexa-hydro-1H-cyclopenta[b]naphth-2-yl] 4-phenylbenzo-ate (MPK-8)

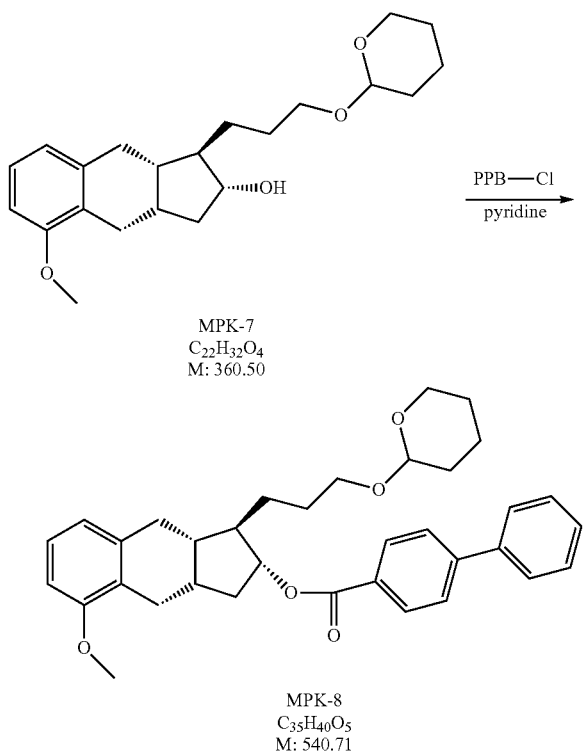

In an inert atmosphere 636 g of MPK-7 is dissolved in 1.4 l of pyridine and 508 g of p-phenylbenzoyl chloride is added to the solution. The reaction mixture is stirred at 50-60° C. At the end of the reaction water and tert-butyl methyl ether are added, the phases are separated, the aqueous phase is extracted with tert-butyl methyl ether. The united organic phase is washed consecutively with NaHSO₄ solution, K₂CO₃ solution and water, dried, filtered and evaporated. The crude product is purified by chromatography on silica gel using hexane: ethyl acetate mixtures as eluent.

Yield: 763 g (80%) of white crystals. Mp: 140-143° C.

NMR data:

(CDCl3), 1H NMR (500 MHz): 8.06 ppm (H-31 and H-31', 2), d, J=8.4 Hz; 7.66-7.58 ppm (H-32, H-32', H-35 and H-35', 4), m (in: 7.63 ppm (H-32 and H-32', 2), m (d), J=8.5 Hz; 7.61 ppm (H-35 and H-35', 2), m (d), J=7.3 Hz); 7.46 ppm (H-36 and H-36', 2), m (t), J=7.5 Hz; 7.39 ppm (H-37, 1), m (t), J=7.4 Hz; 7.14 ppm (H-22, 1), t, J=7.8 Hz; 6.82 ppm (H-23, 1), m (d/dbroad), J=7.4 Hz; 6.77 ppm (H-21, 1), d, J=8.2 Hz; 5.03 ppm (H-11, 1), td, J=8.4 Hz and 6.3 Hz; 4.565 ppm (H-24, 1), m; 3.895-3.79 ppm (H-2 and H-28a, 4), m (in: 3.85 ppm (H-28a, 1), m; 3.82 ppm (H-2, 3), s); 3.79-3.72 ppm (H-15a, 1), m (in: 3.758 ppm (H-15a, 0.5), dt, J-=9.7 Hz and 6.6 Hz; 3.752 ppm (H-15a, 0.5), dt, J=9.7 Hz and 6.5 Hz); 3.48 ppm (H-28b, 1), m; 3.45-3.375 ppm (H-15b, 1), m (in: 3.416 ppm (H-15b, 0.5), dt, J=9.6 Hz and 6.6 Hz; 3.410 ppm (H-15b, 0.5), dt, J-=9.6 Hz and 6.4 Hz); 2.95-2.81 ppm (H-4a and H-7a, 2), m (in: 2.91 ppm (H-4a, 1), dd, J=14.9 Hz and 6.2 Hz; 2.85 ppm (H-7a, 1), dd, J=14.5 Hz and 6.3); 2.635-2.34 ppm (H-4b, H-7b, H-9 and H-10a, 4), m (in: 2.589 ppm (H-7b, 0.5), m (dd), J=14.4 Hz and 6.9 Hz; 2.587 ppm (H-7b, 0.5), m (dd), J=14.6 Hz and 7.0 Hz; 2.535 ppm (H-4b, 1), dd, J=14.9 Hz and 7.2 Hz; 2.48 ppm (H-10a, 1), m (ddd), J=6.4 Hz; 2.40 ppm (H-9, 1), m, J~7.7 Hz); 2.03 ppm (H-8, 1), m (tt), J=9.1 Hz and 6.8 Hz; 1.88-1.45 ppm (H-12, H-13, H-14, H-25, H-26 and H-27, 11), m (in: 1.83 ppm (H-12, 1), m; 1.81 ppm (H-26a, 1), m; 1.77 ppm (H-14a, 1), m; 1.74 ppm (H-14b, 1), m; 1.69 ppm (H-25a, 1), m; 1.63 ppm (H-13a, 1), m; 1.60 ppm (H-13b, 1), m; 1.57 ppm (H-25b, 1), m; 1.55 ppm (H-27a, 1), m; 1.51 ppm (H-27b, 1), m; 1.50 ppm (H-26b, 1), m); 1.385 ppm (H-10b, 1), dt, J=12.3 Hz and 8.7 Hz; 13C NMR (125.8 MHz): 166.44 ppm (C-29), 156.64 ppm (C-3), 145.64 ppm (C-33), 140.26 ppm (C-6); 140.21 ppm (C-34), 130.20 ppm (C-31 és C-31', 2), 129.44 ppm (C-30), 129.03 ppm (C-36 and C-36', 2), 128.21 ppm (C-37), 127.39 ppm (C-35 and C-35', 2), 127.12 ppm (C-32 and C-32', 2), 126.83 ppm (C-5), 126.33 ppm (C-22), 120.58 ppm and 120.57 ppm (C-23), 108.42 ppm (C-21), 99.02 ppm (C-24), 80.04 ppm and 80.00 ppm (C-11), 67.88 ppm and 67.84 ppm (C-15), 62.51 ppm and 62.49 ppm (C-28), 55.65 ppm (C-2), 49.58 ppm (C-12), 41.00 ppm and 40.99 ppm (C-8), 38.00 ppm (C-10), 33.85 ppm (C-9), 33.80 ppm (C-7), 30.89 ppm and 30.88 ppm (C-25), 29.61 ppm and 29.58 ppm (C-13), 27.91 ppm and 27.89 ppm (C-14), 25.92 ppm (C-4), 25.61 ppm (C-27), 19.81 ppm and 19.80 ppm (C-26).

2j.) Preparation of [(1R,2R,9aS)-1-(3-hydroxypropyl)-5-methoxy-2,3,3a,4,9,9a-hexahydro-1H-cyclopenta[b]naphth-2-yl] 4-phenylbenzoate (MPK-9)

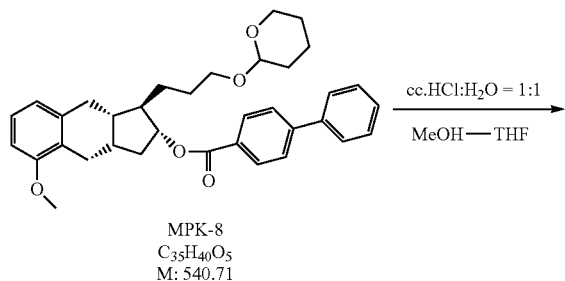

MPK-8
C35H40O5
M: 540.71 cc.HCl:H2O = 1:1
MeOH—THF

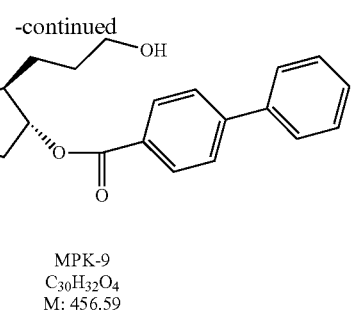

MPK-9
C30H32O4
M: 456.59

574 g of MPK-8 is dissolved in 1.2 l of tetrahydrofuran. 4.6 L of methanol, and then carefully the mixture of 145 ml of conc. hydrochloric acid and 145 ml of water are added. At the end of the reaction the mixture is quenched with 1M NaHCO3 solution and the solvents are distilled off. The residual aqueous phase is extracted with ethyl acetate, the united organic phase is washed with water, dried, filtered and evaporated. The evaporated crude product is purified by chromatography on silica gel.

Yield: 376 g (78%) of colourless oil.

NMR data:

(CDCl3), 1H NMR (500 MHz): 8.05 ppm (H-31 and H-31', 2), d, J=8.4 Hz; 7.67-7.57 ppm (H-32, H-32', H-35 and H-35', 4), m (in: 7.63 ppm (H-32 and H-32', 2), m (d), J=8.4 Hz; 7.605 ppm (H-35 and H-35', 2), m (d), J=7.2 Hz); 7.46 ppm (H-36 and H-36', 2), m (t), J=7.5 Hz; 7.39 ppm (H-37, 1), m (t), J=7.3 Hz; 7.14 ppm (H-22, 1), t, J=7.8 Hz; 6.81 ppm (H-23, 1), d, J=7.4 Hz; 6.78 ppm (H-21, 1), d, J=8.2 Hz; 5.05 ppm (H-11, 1), td, J=8.3 Hz and 6.3 Hz; 3.82 ppm (H-2, 3), s, 3.66 ppm (H-15, 2), m; 2.94-2.80 ppm (H-4a and H-7a, 2), m (in: 2.90 ppm (H-4a, 1), dd, J=14.9 Hz and 6.1 Hz; 2.845 ppm (H-7a, 1), dd, J=14.5 Hz and 6.3); 2.63-2.50 ppm (H-4b and H-7b, 2), m (in: 2.58 ppm (H-7b, 1), dd, J=14.6 Hz and 6.8 Hz; 2.55 ppm (H-4b, 1), dd, J=15.0 Hz and 7.0 Hz); 2.50-2.35 ppm (H-9 and H-10a, 2), m (in: 2.465 ppm (H-10a, 1), m (ddd), J=12.3 Hz, 7.6 Hz and 6.3 Hz; 2.40 ppm (H-9, 1), m, J~7.6 Hz); 2.03 ppm (H-8, 1), m (tt), J=8.9 Hz and 6.9 Hz, 1.81 ppm (H-12, 1), m (tt), J=8.2 Hz and 6.7 Hz; 1.77-1.45 ppm (H-13 and H-14, 4), m (in: 1.73 ppm (H-14a, 1), m; 1.70 ppm (H-14b, 1), m; 1.625 ppm (H-13a, 1), m; 1.60 ppm (H-13b, 1), m), 1.39 ppm (H-10b, 1), dt, J=12.2 Hz and 8.6 Hz, 13C NMR (125.8 MHz): 166.50 ppm (C-29), 156.66 ppm (C-3), 145.72 ppm (C-33), 140.16 ppm (C-6 and C-34, 2); 130.20 ppm (C-31 and C-31', 2), 129.33 ppm (C-30), 129.04 ppm (C-36 and C-36', 2), 128.24 ppm (C-37), 127.39 ppm (C-35 and C-35', 2), 127.16 ppm (C-32 and C-32', 2), 126.78 ppm (C-5), 126.37 ppm (C-22), 120.58 ppm (C-23), 108.45 ppm (C-21), 79.86 ppm (C-11), 63.29 ppm (C-15), 55.65 ppm (C-2), 49.36 ppm (C-12), 40.96 ppm (C-8), 37.98 ppm (C-10), 33.76 ppm (C-9), 33.69 ppm (C-7), 30.77 ppm (C-14), 28.98 ppm (C-13), 25.88 ppm (C-4).

2k.) Preparation of [(1R,9aS)-5-methoxy-1-(3-oxo-propyl)-2,3,3a,4,9,9a-hexahydro-1H-cyclopenta[b]naphth-2-yl] 4-phenylbenzoate (MPK-10)

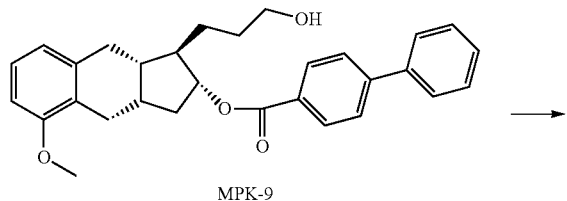

MPK-9
C30H32O4
M: 456.59

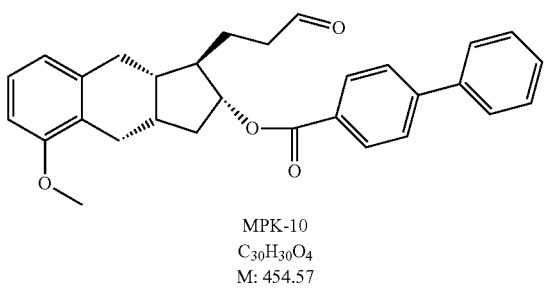

MPK-10
C30H30O4
M: 454.57

In an inert atmosphere 140 ml of oxalyl chloride is dissolved in 4.2 l of dichloromethane. The solution is cooled to (−)−60° C. and 227 ml of dimethyl sulfoxide in 1130 ml dichloromethane solution and then, after stirring 376 g of MPK-9 in 690 ml of dichloromethane solution are added. Stirring is continued at (−)−60° C. At the end of the reaction the mixture is quenched by the addition of 830 ml triethylamine. The mixture is agitated for 1 hour without cooling, then the temperature is elevated to 10° C. and 1M NaHSO4 solution is added. The aqueous phase is extracted with dichloromethane, the united organic phase is washed with water, dried and evaporated. The crude product is purified first by chromatography on silica gel column using hexane:ethyl acetate mixture as eluent, then by crystallisation from toluene:hexane mixture.

Yield: 374 g (100%) of white crystals. Mp: 94-96° C.
NMR data:
(CDCl3), 1H NMR (500 MHz): 9.78 ppm (H-15, 1), t, J=1.3 Hz; 8.05 ppm (H-31 and H-31', 2), m (d), J=8.5 Hz; 7.68-7.57 ppm (H-32, H-32', H-35 and H-35', 4), m (in: 7.64 ppm (H-32 and H-32', 2), m (d), J=8.5 Hz; 7.61 ppm (H-35 and H-35', 2), m (d), J=7.0 Hz); 7.46 ppm (H-36 and H-36', 2), m (t), J=7.6 Hz; 7.39 ppm (H-37, 1), m (t), J=7.4 Hz; 7.15 ppm (H-22, 1), t, J=7.8 Hz, 6.82 ppm (H-23, 1), d, J=7.4 Hz; 6.78 ppm (H-21, 1), d, J=8.2 Hz, 5.02 ppm (H-11, 1), td, J=8.3 Hz and 6.3 Hz; 3.82 ppm (H-2, 3), s; 2.935-2.79 ppm (H-4a and H-7a, 2), m (in: 2.865 ppm (H-4a, 1), dd, J=14.9 Hz and 6.1 Hz; 2.835 ppm (H-7a, 1), dd, J=14.4 Hz and 6.3); 2.65-2.53 ppm (H-4b, H-7b and H-14, 4), m (in: 2.61 ppm (H-14, 2), ddd, J=7.6 Hz, 6.5 Hz and 1.1 Hz; 2.576 ppm (H-7b, 1), dd, J=14.5 Hz and 6.3 Hz; 2.568 ppm (H-4b, 1), dd, J=14.9 Hz and 6.5 Hz); 2.53-2.36 ppm (H-9 and H-100, 2), m (in: 2.485 ppm (H-10β, 1), ddd, J=12.1 Hz, 7.6 Hz and 6.4 Hz; 2.42 ppm (H-9, 1), m); 2.075-1.89 ppm (H-8 and H-13a, 2), m (in: 2.02 ppm (H-8, 1), m, 1.94 ppm (H-13a, 1), m); 1.85-1.73 ppm (H-12 and H-13b, 2), m (in: 1.80 ppm (H-14b, 1), m; 1.79 ppm (H-12, 1), m); 1.345 ppm (H-10a, 1), dt, J=12.2 Hz and 8.8 Hz, 13C NMR (125.8 MHz): 202.22 ppm (C-15), 166.33 ppm (C-29), 156.71 ppm (C-3), 145.85 ppm (C-33), 140.11 ppm (C-34); 139.82 ppm (C-6), 130.20 ppm (C-31 and C-31', 2), 129.11 ppm (C-30), 129.06 ppm (C-36 and C-36', 2), 128.28 ppm (C-37), 127.40 ppm (C-35 and C-35', 2), 127.21 ppm (C-32 and C-32', 2), 126.60 ppm (C-5), 126.46 ppm (C-22), 120.66 ppm (C-23), 108.54 ppm (C-21), 79.48 ppm (C-11), 55.65 ppm (C-2), 48.70 ppm (C-12), 41.95 ppm (C-14), 40.79 ppm (C-8), 37.91 ppm (C-10), 33.53 ppm (C-9), 33.29 ppm (C-7), 25.73 ppm (C-4), 24.69 ppm (C-13).

2l1.) Preparation of [(1R,2R,9aS)-1-[(3S)-3-hydroxyoctyl]-5-methoxy-2,3,3a,4,9,9a-hexahydro-1H-cyclopenta[b]naphth-2-yl] 4-phenylbenzoate (PPB-TREP-14)

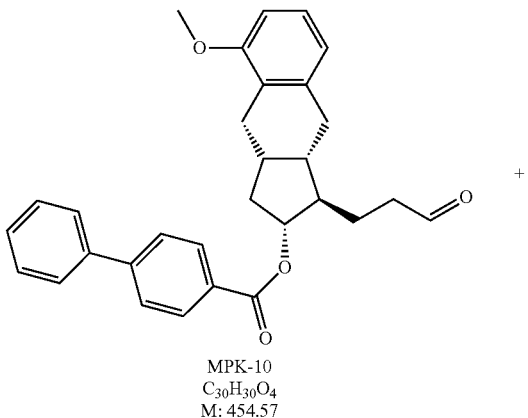

MPK-10
C30H30O4
M: 454.57

+

-continued
dipentylzinc
C₁₀H₂₂Zn
M: 207.66
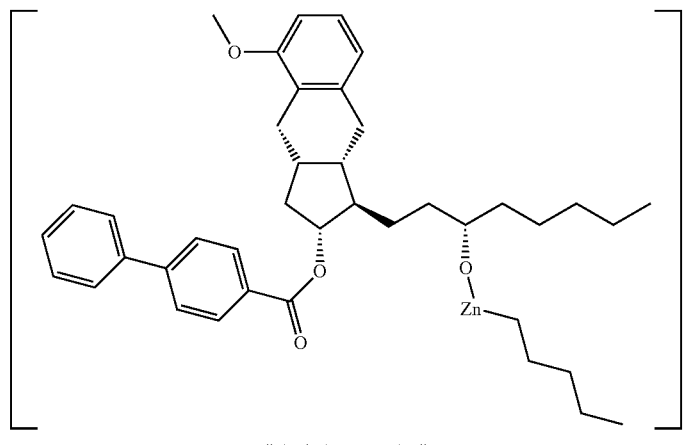
"alcoholate complex"
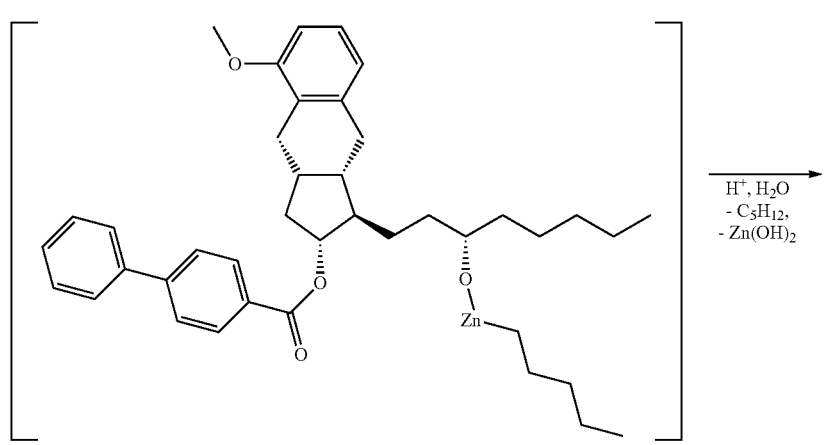
"alcoholate complex"
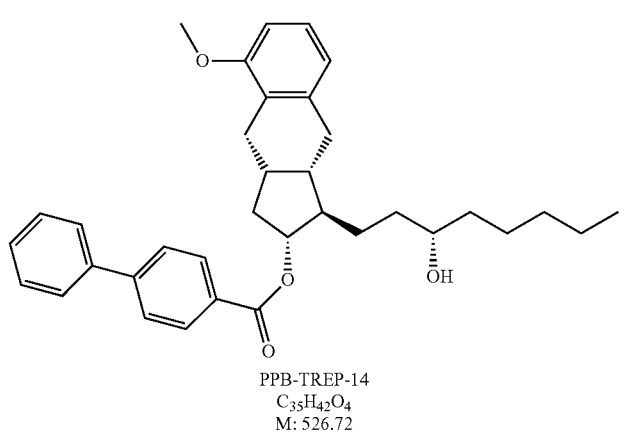
PPB-TREP-14
C₃₅H₄₂O₄
M: 526.72

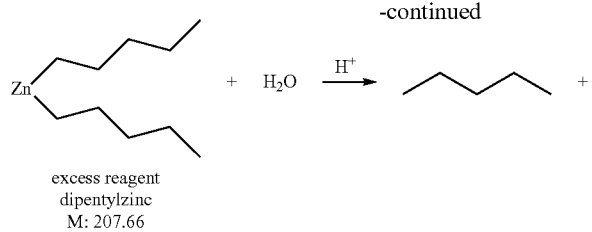

excess reagent
dipentylzinc
M: 207.66

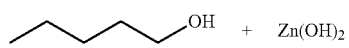

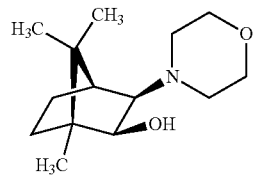

To 4.5 l of distilled toluene in an inert atmosphere 7.5 g of MIB* catalyst and then 1800 ml of dipentylzinc are added. The mixture is agitated at room temperature. After 1 hour of agitation the solution of 300 g of MPK-10 in 1.5 l of distilled toluene is added at room temperature and the mixture is stirred until the coupling reaction proceeds. Then, under intensive agitation, the reaction mixture is poured onto hydrochloric acid solution. Stirring is continued till complete decomposition of the zinc salts, then the product is extracted with ethyl acetate. The organic phase is washed with water and saturated sodium chloride solution and then evaporated. The crude product is purified by gradient chromatography on silica gel column using toluene:tert-butyl methyl ether mixtures as eluent.

Yield: 300 g (86%) of yellow oil.

NMR data:

(CDCl3), 1H NMR (500 MHz): 8.05 ppm (H-31 and H-31', 2), m (d), J=8.3 Hz; 7.68-7.53 ppm (H-32, H-32', H-35 and H-35', 4), m (in: 7.63 ppm (H-32 and H-32', 2), m (d), J=8.3 Hz; 7.605 ppm (H-35 and H-35', 2), m (d), J=7.5 Hz), 7.46 ppm (H-36 and H-36', 2), m (t), J=7.6 Hz, 7.39 ppm (H-37, 1), m (t), J=7.3 Hz, 7.14 ppm (H-22, 1), t, J=7.8 Hz, 6.82 ppm (H-23, 1), d, J=7.4 Hz; 6.78 ppm (H-21, 1), d, J=8.2 Hz, 5.05 ppm (H-11, 1), td, J=8.2 Hz and 6.4 Hz, 3.82 ppm (H-2, 3), s, 3.61 ppm (H-15, 1), m; 2.955-2.80 ppm (H-4a and H-7a, 2), m (in: 2.905 ppm (H-4a, 1), dd, J=14.9 Hz and 6.1 Hz; 2.85 ppm (H-7a, 1), dd, J=14.5 Hz and 6.3), 2.66-2.51 ppm (H-4b and H-7b, 2), m (in: 2.585 ppm (H-7b, 1), dd, J=14.5 Hz and 6.8 Hz; 2.54 ppm (H-4b, 1), dd, J=15.1 Hz and 7.0 Hz), 2.51-2.35 ppm (H-9 and H-10a, 2), m (in: 2.47 ppm (H-10a, 1), ddd, J=12.3 Hz, 7.6 Hz and 6.4 Hz; 2.41 ppm (H-9, 1), m), 2.03 ppm (H-8, 1), m (tt), J-=9.0 Hz and 6.8 Hz, 1.81 ppm (H-12, 1), m, 1.75-1.48 ppm (H-13 and H-14, 4), m (in: 1.675 ppm (H-13a, 1), m; 1.62 ppm (H-14a, 1), m; 1.59 ppm (H-13b, 1), m; 1.545 ppm (H-14b, 1), m); 1.48-1.33 ppm (H-10b, H-16, H-17a and OH-15, 5), m (in: 1.43 ppm (H-16a, 1), m; 1.41 ppm (H-17a, 1), m; 1.40 ppm (H-16b, 1), m; 1.39 ppm (H-10b, 1), m), 1.33-1.17 ppm (H-17b, H-18 and H-19, 5), m (in: 1.28 ppm (H-19, 2), m; 1.27 ppm (H-17b, 1), m; 1.26 ppm (H-18, 2), m), 0.86 ppm (H-20, 3), m (t). J=6.8 Hz, 13C NMR (125.8 MHz): 166.46 ppm (C-29), 156.67 ppm (C-3), 145.70 ppm (C-33), 140.21 ppm/140.14 ppm (C-6/C-34), 130.20 ppm (C-31 and C-31', 2), 129.39 ppm (C-30), 129.04 ppm (C-36 and C-36', 2), 128.24 ppm (C-37), 127.40 ppm (C-35 and C-35', 2), 127.13 ppm (C-32 and C-32', 2), 126.82 ppm (C-5), 126.36 ppm (C-22), 120.60 ppm (C-23), 108.45 ppm (C-21), 79.83 ppm (C-11), 73.13 ppm (C-15), 55.66 ppm (C-2), 49.41 ppm (C-12), 40.94 ppm (C-8), 38.03 ppm (C-10), 37.55 ppm (C-16), 35.11 ppm (C-14), 33.78 ppm (C-9), 33.67 ppm (C-7), 32.02 ppm (C-18), 28.53 ppm (C-13), 25.92 ppm (C-4), 25.43 ppm (C-17), 22.76 ppm (C-19), 14.16 ppm (C-20).

*MIB catalyst: (2S)-3-exo-(morpholino)isoborneol, M: 239.35, $C_{14}H_{25}NO_2$

Preparation of Dipentylzinc

To 550 g of vaseline 267 g of zinc-copper alloy (10% copper, 90% zinc) is added. In an inert atmosphere the mixture is heated to approx. 60° C., then agitation is started and the mixture is heated to 160° C. Under continuous reflux and intensive cooling the mixture of 188 ml of 1-pentyl iodide and 186 ml of 1-pentyl bromide is added. After the addition agitation is continued for 1 hour while keeping the temperature. The mixture is then cooled to approx. 60° C. The product is distilled off at an inner temperature of 110-150° C. under 0.5-1.5 mbar vacuum.

21.2) Preparation of [(1R,2R,9aS)-1-[(3S)-3-hydroxyoctyl]-5-methoxy-2,3,3a,4,9,9a-hexahydro-1H-cyclopenta[b]naphth-2-yl] 4-phenylbenzoate (PPB-TREP-14)

In 16 ml of dichloromethane 1.3 ml of Ti(OiPr)4 is dissolved and after cooling to (−70° C. 1.1 ml (2.2 mmol) of pentylmagnesium bromide (2M solution in diethyl ether) is added to the mixture. In 4 ml of dichloromethane 100 mg (0.22 mmol) of MPK-10, 10 mg of (R)-(+)-1,1'-Bi(2-naphthol) and 0.4 ml of Ti(OiPr)₄ are dissolved, the solution is cooled to 0/+5 OC and the pentylmagnesium bromide reagent solution is added to it. Stirring is continued at 0/+5° C. At the end of the reaction 2 ml of 1:1 hydrochloric acid-water mixture is added carefully. The phases are separated, the organic phase is washed with 5 ml of water, dried and evaporated. The crude product contains 0-20% 15-epi-PPB-TREP-14 isomer. The product is purified by chromatography on silica gel using hexane:ethyl acetate mixture as eluent.

Yield: 90 mg (77%) of yellow oil.

2m.) Preparation of (1R,2R,3aS,9aS)-1-[(3S)-3-hydroxyoctyl]-5-methoxy-2,3,3a,4,9,9a-hexahydro-1H-cyclopenta[b]naphth-2-ol (TREP-14)

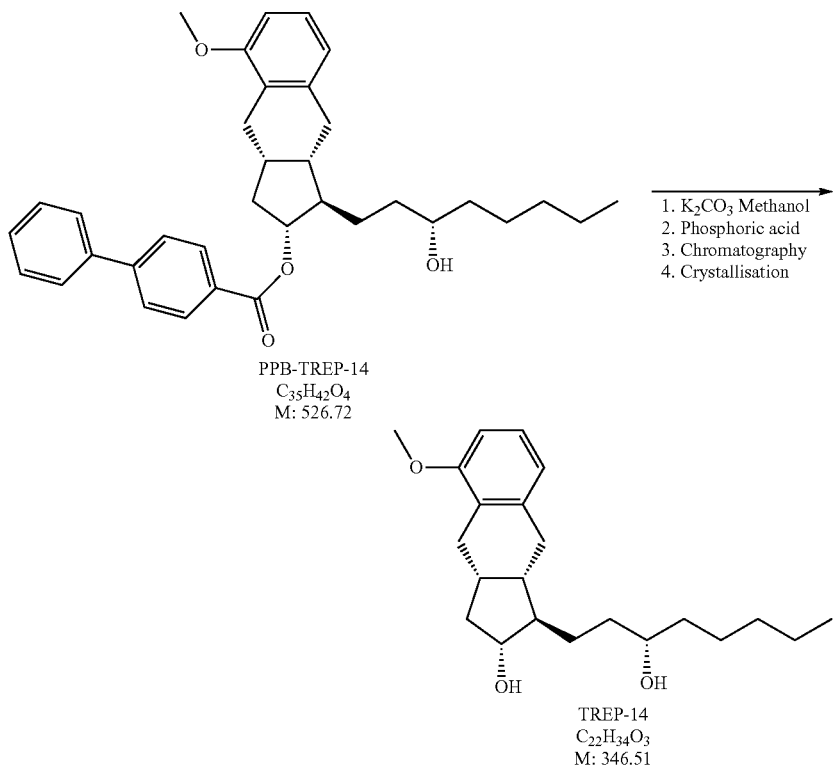

In 1 l of tetrahydrofuran 250 g of PPB-TREP-14 is dissolved, to the solution 2.5 l of methanol and 150 g of potassium carbonate are added and the mixture is stirred at 45° C. At the end of the reaction the pH of the mixture is set to 2-4 with diluted phosphoric acid, the precipitated crystals are filtered off and washed with methanol. The filtrate solution is concentrated, to the concentrated product solution ethyl acetate is added, the phases are separated, the aqueous phase is extracted with ethyl acetate, the united organic phase is washed with sodium chloride solution and evaporated. The crude product is purified by chromatography on silica gel column using hexane: ethyl acetate mixtures as eluent. The evaporated main fraction is crystallized in diisopropyl ether:hexane mixture.

Yield: 125 g (76%) of white crystals. Mp: 71-72° C.

The invention claimed is:

1. Sodium salt monohydrate of treprostinil of formula I

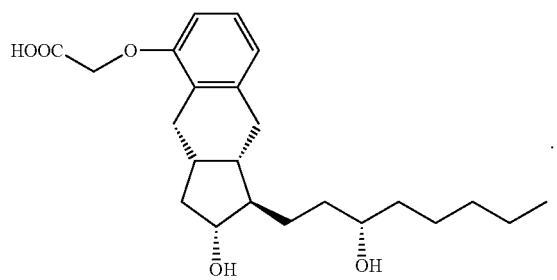

2. Sodium salt monohydrate of treprostinil of formula I

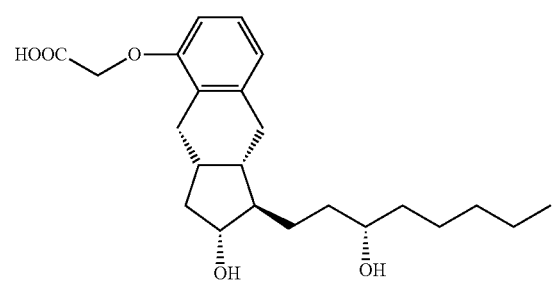

characterized by having: Mp: 95-99° C., DSC peak: 94-99° C., and water content: 4.3 to 4.4%.

* * * * *